US010426794B2

(12) United States Patent
Quintana et al.

(10) Patent No.: US 10,426,794 B2
(45) Date of Patent: Oct. 1, 2019

(54) METHODS AND COMPOSITIONS OF TREATING AUTOIMMUNE DISEASES

(71) Applicant: THE BRIGHAM AND WOMEN'S HOSPITAL, INC., Boston, MA (US)

(72) Inventors: Francisco J. Quintana, Brookline, MA (US); Ivan D. Mascanfroni, Brighton, MA (US)

(73) Assignee: THE BRIGHAM AND WOMEN'S HOSPITAL, INC., Boston, MA (US)

( * ) Notice: Subject to any disclaimer, the term of this patent is extended or adjusted under 35 U.S.C. 154(b) by 247 days.

(21) Appl. No.: 14/783,679

(22) PCT Filed: Apr. 11, 2014

(86) PCT No.: PCT/US2014/033872
§ 371 (c)(1),
(2) Date: Oct. 9, 2015

(87) PCT Pub. No.: WO2014/169255
PCT Pub. Date: Oct. 16, 2014

(65) Prior Publication Data
US 2016/0058792 A1    Mar. 3, 2016

Related U.S. Application Data

(60) Provisional application No. 61/853,745, filed on Apr. 11, 2013.

(51) Int. Cl.
A61K 35/15 (2015.01)
A61K 45/06 (2006.01)
A61K 39/00 (2006.01)
C07K 14/54 (2006.01)
C07K 16/28 (2006.01)
C12N 9/14 (2006.01)
A61K 47/69 (2017.01)
A61K 39/395 (2006.01)

(52) U.S. Cl.
CPC .............. A61K 35/15 (2013.01); A61K 39/00 (2013.01); A61K 39/0008 (2013.01); A61K 45/06 (2013.01); A61K 47/6929 (2017.08); C07K 14/54 (2013.01); C07K 16/2851 (2013.01); C12N 9/14 (2013.01); A61K 2039/5154 (2013.01); A61K 2039/577 (2013.01); C07K 2319/33 (2013.01); C12Y 306/01005 (2013.01)

(58) Field of Classification Search
None
See application file for complete search history.

(56) References Cited

U.S. PATENT DOCUMENTS 8,178,308 B2    5/2012  De Waal Malefyt et al.
2009/0110644 A1  4/2009  Margel et al.
2009/0124573 A1  5/2009  Mazmanian et al.
2010/0068174 A1  3/2010  Jacobson
2010/0150862 A1  6/2010  Devergne
2012/0082644 A1  4/2012  Mannie

FOREIGN PATENT DOCUMENTS

WO    2006/066088 A2    6/2006
WO    2010/072797 A1    7/2010
WO    2011160062 A2    12/2011

OTHER PUBLICATIONS

Karakhanova et al, Journal of Leukocyte Biology, Jun. 2011, vol. 89, pp. 837-845.*
Wells, 1990, Biochemistry 29:8509-8517.*
Bork, 2000, Genome Research 10:398-400.*
Skolnick et al., 2000, Trends in Biotech. 18(1):34-39.*
Doerks et al., 1998, Trends in Genetics 14:248-250.*
Tokuriki and Tawflik, Current Opinion in Structural Biology 2009, 19: 596-604.*
Karakhanova et al Journal of Leukocyte, 2011, vol. 89, pp. 837-845.*
Apetoh et al., "The aryl hydrocarbon receptor interacts with c-Maf to promote the differentiation of type 1 regulatory T cells induced by IL-27", Nature Immunolology 11(9):854-861 (2010).
Awasthi et al., "A dominant function for interleukin 27 in generating interleukin 10-producing anti-inflammatory T cells", Nature Immunology 8(12):1380-1389 (2007).
Bailey et al., "CNS myeloid DCs presenting endogenous myelin peptides 'preferentially' polarize CD4+ T(H)-17 cells in relapsing EAE", Nature Immunology 8(2):172-180 (2007).
Bailey-Bucktrout et al., "Cutting Edge: Central Nervous System Plasmacytoid Dendritic Cells Regulate the Severity of Relapsing Experimental Autoimmune Encephalomyelitis", The Journal of Immunology 180:6457-6461 (2008).
Banchereau et al., "Dendritic cells and the control of immunity", Nature 392:245-252 (1998).
Banchereau et al., "Immunobiology of Dendritic Cells", Annu. Rev. Immunol. 18:767-811 (2000).
Bar-On et al., "Defining dendritic cells by conditional and constitutive cell ablation", Immunological Reviews 234:76-89 (2010).
Batten et al., "Interleukin 27 limits autoimmune encephalomyelitis by suppressing the development of interleukin 17-producing T cells", Nature Immunology 7(9):929-936 (2006).

(Continued)

Primary Examiner — Bridget E Bunner
Assistant Examiner — Fozia Hamud
(74) Attorney, Agent, or Firm — Nixon Peabody LLP; David S. Resnick; Mark J. FitzGerald

(57) ABSTRACT

Embodiments of various aspects described herein are directed to methods and compositions for producing a tolerognic or immunosuppressive dendritic cell. In particular, an immunosuppressive dendritic cell can be produced by contacting a dendritic cell with an agent that stimulates the IL 27/ectonucleotidase CD39 axis signaling. In some embodiments, the methods and/or compositions described herein can be used for treating an autoimmune disease or disorder, e.g., but not limited to multiple sclerosis (MS) and type 1 diabetes.

4 Claims, 47 Drawing Sheets
Specification includes a Sequence Listing.

(56) References Cited

OTHER PUBLICATIONS

Bauquet et al., "The costimulatory molecule ICOS regulates the expression of c-Maf and IL-21 in the development of follicular T helper cells and TH-17 cells", Nature Immunology 10(2):167-175 (2009).
Bettelli et al., "IL-10 is Critical in the Regulation of Autoimmune Encephalomyelitis as Demonstrated by Studies of IL-10- and IL-4-Deficient and Transgenic Mice", The Journal of Immunology 161:3299-3306 (1998).
Bettelli et al., "Myelin Oligodendrocyte Glycoprotein-specific T Cell Receptor Transgenic Mice Develop Spontaneous Autoimmune Optic Neuritis", J. Exp. Med. 197(9):1073-1081 (2003).
Bettelli et al., "Reciprocal developmental pathways for the generation of pathogenic effector TH17 and regulatory T cells", Nature 441:235-238 (2006).
Bluestone et al., "What does the future hold for cell-based tolerogenic therapy?", Nat. Rev. Immunol. 7:650-654 (2007).
Chambers et al., "Costimulatory regulation of T cell function", Current Opinion in Cell Biology 11:203-210 (1999).
Comabella et al., "A type I interferon signature in monocytes is associated with poor response to interferon-beta in multiple sclerosis", Brain 132:3353-3365 (2009).
Comabella et al., "Targeting dendritic cells to treat multiple sclerosis", Nature Reviews Neurology 6:499-507 (2010).
Dhodapkar et al., "Antigen-specific Inhibition of Effector T Cell Function in Humans after Injection of Immature Dendritic Cells", J. Exp.Med. 193(2):233-238 (2001).
Fajardo-Moser et al., "Mechanisms of dendritic cell-based vaccination against infection", International Journal of Microbiology 298:11-20 (2008).
Fitzgerald et al., "Suppressive Effect of IL-27 on Encephalitogenic Th17 Cells and the Effector Phase of Experimental Autoimmune Encephalomyelitis", The Journal of Immunology 179:3268-3275 (2007).
Flamar et al., "P17-04. Targeting HIV peptides to human dendritic cells via CD40 elicits expansion of multi-epitope polyfunctional CD4+ and CD8+ T cells in HIV patients", Retrovirology 6(Suppl. 3):p. 286 (2009).
Gandhi et al., "Activation of the aryl hydrocarbon receptor induces human type 1 regulatory T cell-like and Foxp3+ regulatory T cells", Nat. Immunol. 11(9):846-853 (2010).
Gately et al., "The Interleukin-12/Interleukin-12-Receptor System: Role in Normal and Pathologic Immune Responses", Annu. Rev. Immunol. 16:495-521 (1998).
Giannoukakis et al., "Phase I (Safety) Study of Autologous Tolerogenic Dendritic Cells in Type 1 Diabetic Patients", Diabetes Care 34:2026-2032 (2011).
Gilboa, "DC-based cancer vaccines", The Journal of Clinical Investigation 117(5):1195-1203 (2007).
Glimcher et al., "Lineage commitment in the immune system: the T helper lymphocyte grows up", Genes and Development 14:1693-1711 (2000).
Greter et al., "Dendritic cells permit immune invasion of the CNS in an animal model of multiple sclerosis", Nature Medicine 11(3):328-334 (2005).
Gross et al., "Dendritic cell vaccination in autommune disease", Curr. Opin. Rheumatol. 25(2):268-274 (2013).
Groux et al., "A CD4+ T-cell subset inhibits antigen-specific T-cell responses and prevents colitis", Nature 389:737-742 (1997).
Guermonprez et al., "Antigen Presentation and T Cell Stimulation by Dendritic Cells", Annu. Rev. Immunol. 20:621-667 (2002).
Harris et al., "An In Vivo Requirement for STAT3 Signaling in TH17 Development and TH17-Dependent Autoimmunity", The Journal of Immunology 179:4313-4317 (2007).
Huh et al., "Digoxin and its derivatives suppress Th17 cell differentiation by antagonizing RORγt activity", Nature 472 (7344):486-490 (2011).
Ivanov et al., "The Orphan Nuclear Receptor RORgammat Directs the Differentiation Program of Proinflammatory IL-17+ T Helper Cells", Cell 126:1121-1133 (2006).
Jung et al., "In Vivo Depletion of CD11c+ Dendritic Cells Abrogates Priming of CD8+ T Cells by Exogenous Cell-Associated Antigens", Immunity 17:211-220 (2002).
Kastelein et al., "Discovery and Biology of IL-23 and IL-27: Related but Functionally Distinct Regulators of Inflammation", Annu. Rev. Immunol. 25:221-242 (2007).
Kimura et al., "Aryl hydrocarbon receptor regulates Stat1 activation and participates in the development of Th17 cells", PNAS 105(28):9721-9726 (2008).
Korn et al., "IL-17 and Th17 Cells", Annu. Rev. Immunol. 27:485-517 (2009).
Korn et al., "IL-21 initiates an alternative pathway to induce proinflammatory T(H)17 cells", Nature 448 (7152):484-487 (2007).
Kuchroo et al., "Experimental allergic encephalomyelitis mediated by cloned T cells specific for a synthetic peptide of myelin proteolipid protein. Fine specificity and T cell receptor V beta usage", J. Immunol. 148:3776-3782 (1992).
Kuchroo et al., "T Cell Response in Experimental Autoimmune Encephalomyelitis (EAE): Role of Self and Cross-Reactive Antigens in Shaping, Tuning, and Regulating the Autopathogenic T Cell Repertoire", Annu. Rev. Immunol. 20:101-123 (2002).
Luo et al., "ECDI-fixed allogeneic splenocytes induce donor-specific tolerance for long-term survival of islet transplants via two distinct mechanisms", PNAS 105(38):14527-14532 (2008).
McGeachy et al., "The interleukin 23 receptor is essential for the terminal differentiation of interleukin 17-producing effector T helper cells in vivo", Nat. Immunol. 10(3):314-324 (2009).
McMahon et al., "Epitope spreading initiates in the CNS in two mouse models of multiple sclerosis", Nature Medicine 11(3):5-9 (2005).
Menges et al., "Repetitive Injections of Dendritic Cells Matured with Tumor Necrosis Factor alpha Induce Antigen-specific Protection of Mice from Autoimmunity", J. Exp. Med. 195(1):15-21 (2002).
Mitsdoerffer et al., "New Pieces in the Puzzle: How Does Interferon-beta Really Work in Multiple Sclerosis?", Ann. Neurol. 65:87-88 (2009).
Molle et al., "Critical Role of the IFN-Stimulated Gene Factor 3 Complex in TLR-Mediated IL-27p28 Gene Expression Revealing a Two-Step Activation Process", The Journal of Immunology 184:1784-1792 (2010).
Molle et al. "IL-27 Synthesis Induced by TLR Ligation Critically Depends on IFN Regulatory Factor 3", The Journal of Immunology 178:7607-7615 (2007).
Moore et al., "Interleukin-10 and the Interleukin-10 Receptor", Annu. Rev. Immunol. 19:683-765 (2001).
Nurieva et al., "Essential autocrine regulation by IL-21 in the generation of inflammatory T cells", Nature 148:480-483 (2007).
Pflanz et al., "WSX-1 and Glycoprotein 130 Constitute a Signal-Transducing Receptor for IL-27", The Journal of Immunology 172:2225-2231 (2004).
Phillips et al., "Dendritic cell-based therapy in Type 1 diabetes mellitus", Expert Rev. Clin. Immunol. 5(3):325-339 (2009).
Pot et al., "Cutting Edge: IL-27 Induces the Transcription Factor c-Maf, Cytokine IL-21, and the Costimulatory Receptor ICOS that Coordinately Act Together to Promote Differentiation of IL-10-Producing Tr1 Cells", The Journal of Immunology 183:797-801 (2009).
Quah et al., "Maturation of function in dendritic cells for tolerance and immunity", J. Cell. Mol. Med. 9(3):643-654 (2005).
Quintana et al., "Aiolos promotes TH17 differentiation by directly silencing Il2 expression", Nat. Immunol. 13 (8):770-777 (2012).
Quintana et al., "Control of T(reg) and T(H)17 cell differentiation by the aryl hydrocarbon receptor", Nature 453:65-71 (2008).
Remoli et al., "IFN-beta modulates the response to TLR stimulation in human DC: Involvement of IFN regulatory factor-1 (IRF-1) in IL-27 gene expression", Eur. J. Immunol. 37:3499-3508 (2007).
Roncarolo et al., "Interleukin-10-secreting type 1 regulatory T cells in rodents and humans", Immunological Reviews 212:28-50 (2006).
Sakaguchi, "Naturally Arising CD4+ Regulatory T Cells for Immunologic Self-Tolerance and Negative Control of Immune Responses", Annu. Rev. Immunol. 22:531-562 (2004).

(56) References Cited

OTHER PUBLICATIONS

Saraiva et al., "Interleukin-10 Production by Th1 Cells Requires Interleukin-12-Induced STAT4 Transcription Factor and ERK MAP Kinase Activation by High Antigen Dose", Immunity 31:209-219 (2009).
Saraiva et al., "The regulation of IL-10 production by immune cells", Nat. Rev. Immunol. 10:170-181 (2010).
Shevach, "Regulatory T Cells in Autoimmmunity*", Annu. Rev. Immunol. 18:423-449 (2000).
Shinohara et al., "Engagement of the Type I Interferon Receptor on Dendritic Cells Inhibits T Helper 17 Cell Development: Role of Intracellular Osteopontin", Immunity 29:68-78 (2008).
Shinozaki et al., "Tumor-specific cytotoxic T cell generation and dendritic cell function are differentially regulated by interleukin 27 during development of anti-tumor immunity", Int. J. Cancer 124:1372-1378 (2009).
Solt et al., "Suppression of TH17 Differentiation and Autoimmunity by a Synthetic ROR Ligand", Nature 472 (7344):491-494 (2011).
Sospedra et al., "Immunology of Multiple Sclerosis", Annu. Rev. Immunol. 23:683-747 (2005).
Steinman et al., "Taking dendritic cells into medicine", Nature 449:419-426 (2007).
Strobl et al., "TGF-beta1 regulation of dendritic cells", Microbes and Infection 1:1283-1290 (1999).
Stumhofer et al., "Interleukins 27 and 6 induce STAT3-mediated T cell production of interleukin 10", Nature Immunology 8:1363-1371 (2007).
Stumhofer et al., "Interleukin 27 negatively regulates the development of interleukin 17-producing T helper cells during chronic inflammation of the central nervous system", Nature Immunology 7(9):937-945 (2006).
Tacken et al., "Dendritic-cell immunotherapy: from ex vivo loading to in vivo targeting", Nature Reviews Immunology 7:790-802 (2007).
Trinchieri, "Interleukin-12 and the Regulation of Innate Resistance and Adaptive Immunity", Nature Reviews Immunology 3:133-146 (2003).
Veldhoen et al., "TGFbeta in the Context of an Inflammatory Cytokine Milieu Supports De Novo Differentiation of IL-17-Producing T Cells", Immunity 24:179-189 (2006).
Veldhoen et al., "The aryl hydrocarbon receptor links TH17-cell-mediated autoimmunity to environmental toxins", Nature 453:106-109 (2008).
Wang et al., "Augmentation of Antigen-Presenting and Th1-Promoting Functions of Dendritic Cells by WSX-1(IL-27R) Deficiency", The Journal of Immunology 179:6421-6428 (2007).
Xu et al., "Regulation of Antitumor Immune Responses by the IL-12 Family Cytokines, IL-12, IL-23, and IL-27", Clinical and Developmental Immunology 2010:1-9 (2010).
Yang et al., "STAT3 Regulates Cytokine-Mediated Generation of Inflammatory Helper T Cells", Journal of Biological Chemistry 282(13):9358-9363 (2007).
Yang et al., "T Helper 17 Lineage Differentiation Is Programmed by Orphan Nuclear Receptors ROR alpha and ROR gamma", Immunity 28:29-39 (2008).
Yogev et al., "Dendritic Cells Ameliorate Autoimmunity in the CNS by Controlling the Homeostasis of PD-1 Receptor (+) Regulatory T Cells", Immunity 37:264-275 (2012).
Yoshimoto et al., "IL-27 Suppresses Th2 Cell Development and Th2 Cytokines Production from Polarized Th2 Cells: A Novel Therapeutic Way for Th2-Mediated Allergic Inflammation", The Journal of Immunology 179:4415-4423 (2007).
Zaft et al., "CD11chigh Dendritic Cell Ablation Impairs Lymphopenia-Driven Proliferation of Naive and Memory CD8+ T Cells", The Journal of Immunology 175:6428-6435 (2005).
Matta et al., "IL-27 Production and STAT3-Dependent Upregulation of B7-H1 Mediate Immune Regulatory Functions of Liver Plasmacytoid Dendritic Cells", The Journal of Immunology 188:5227-5237 (2012).
Berchtold et al., "Human monocyte derived dendritic cells express functional P2X and P2Y receptors as well as ecto-nucleotidases", FEBS Letters 458:424-428 (1999).
Dwyer et al., "CD39 and control of cellular immune responses", Purinergic Signalling 3:171-180 (2007).
Fulmer et al., "A gut feeling for CD39", SciBx, 2(40):1-2 (2009).
Mascanfroni et al., "Interleukin-27 acts on dendritic cells to suppress the T-cell response and autoimmunity by inducing the expression of ENTPD1 (CD39)", Nature Immunology 14(10):1054-1063 (2013).
Moreau et al., "Cell therapy using tolerogenic dendritic cells in transplantation", Transplantation Research, 1:13 (2012).
Pujol-Autonell et al., "Immunotherapy with Tolerogenic Dendritic Cells Alone or in Combination with Rapamycin Does Not Reverse Diabetes in NOD Mice", ISRN Endocrinology, Article ID 346987, 5 pgs. (2013).
Sioud et al., "A novel peptide carrier for efficient targeting of antigens and nucleic acids to dendritic cells", FASEB J. 27(8):3272-3283 (2013).
Subramanya et al., "Targeted Delivery of Small Interfering RNA to Human Dendritic Cells to Suppress Dengue Virus Infection and Associated Proinflammatory Cytokine Production", J. Virol. 84(5):2490-2501 (2010).
Torres-Aguilar et al., "Tolerogenic Dendritic Cells Generated with Different Immunosuppressive Cytokines Induce Antigen-Specific Anergy and Regulatory Properties in Memory CD4+ T Cells", J. Immunol., 184:1765-1775 (2010).
Weir et al., "Experimental autoimmune encephalomyelitis induction in naive mice by dendritic cells presenting a self-peptide", Immunol. Cell Biol. 80:14-20 (2002).
Yoshida et al., "Interleukin 27: a double-edged sword for offense and defense", J. Leukoc. Biol., 86:1295-1303 (2009).
Yeste et al., "Nanoparticle-mediated codelivery of myelin antigen and a tolerogenic small molecule suppresses experimental autoimmune encephalomyelitis", Proc. Natl. Acad. U.S.A. 109(28):11270-11275 (2012).
Mascanfroni, et al., "New pieces in the puzzle. How does interferon-β really work in multiple sclerosis?" Ann of Neurology 65(5) 487-488 (2009).

* cited by examiner

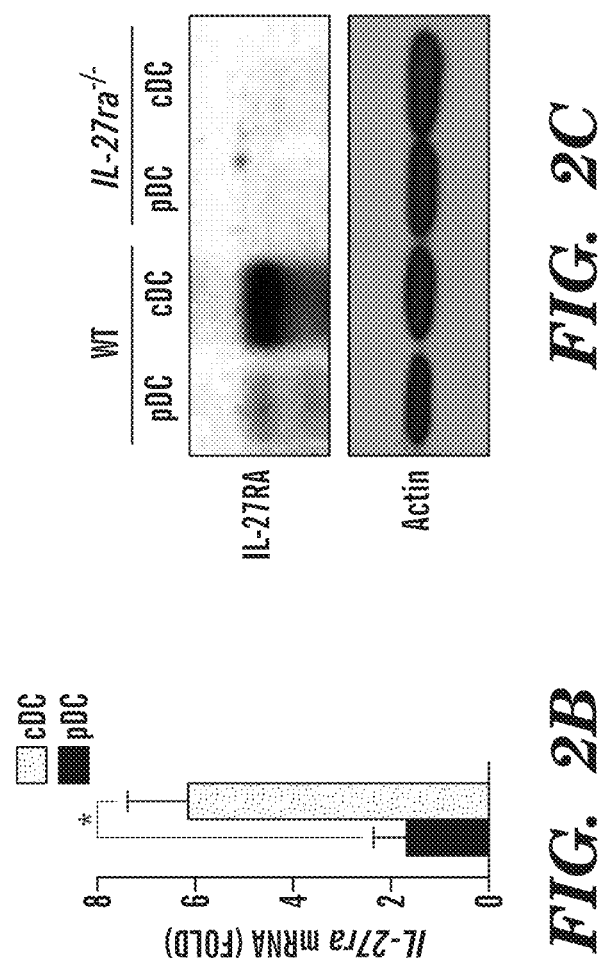
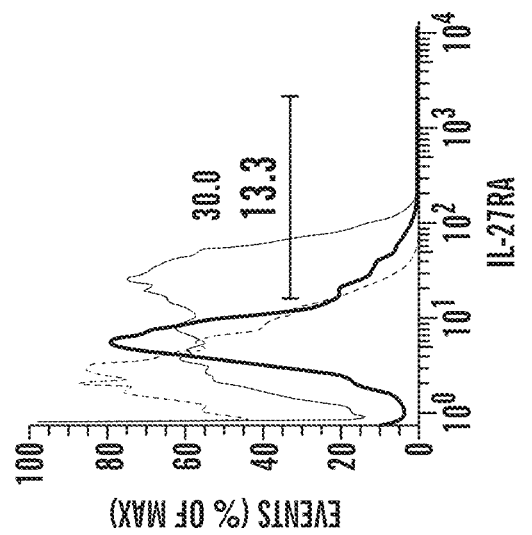
FIG. 2C
FIG. 2B
FIG. 2A

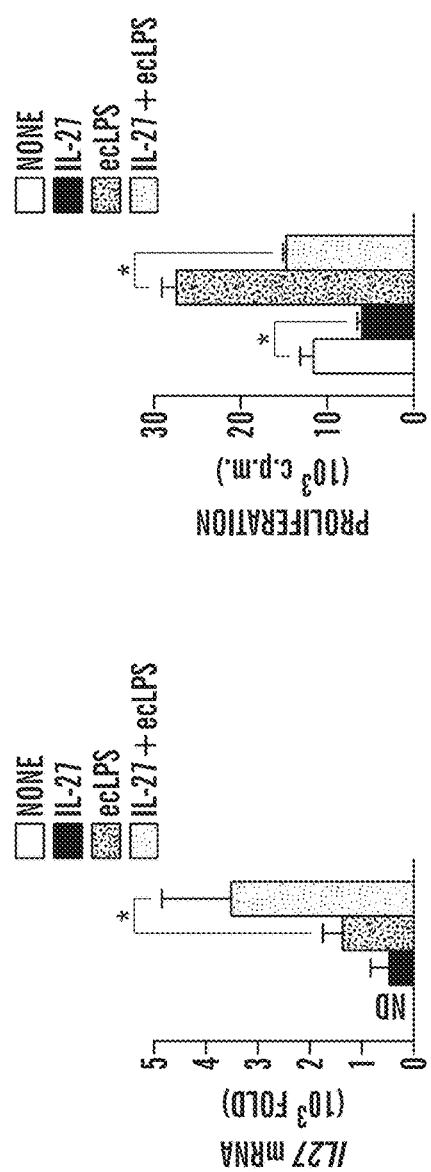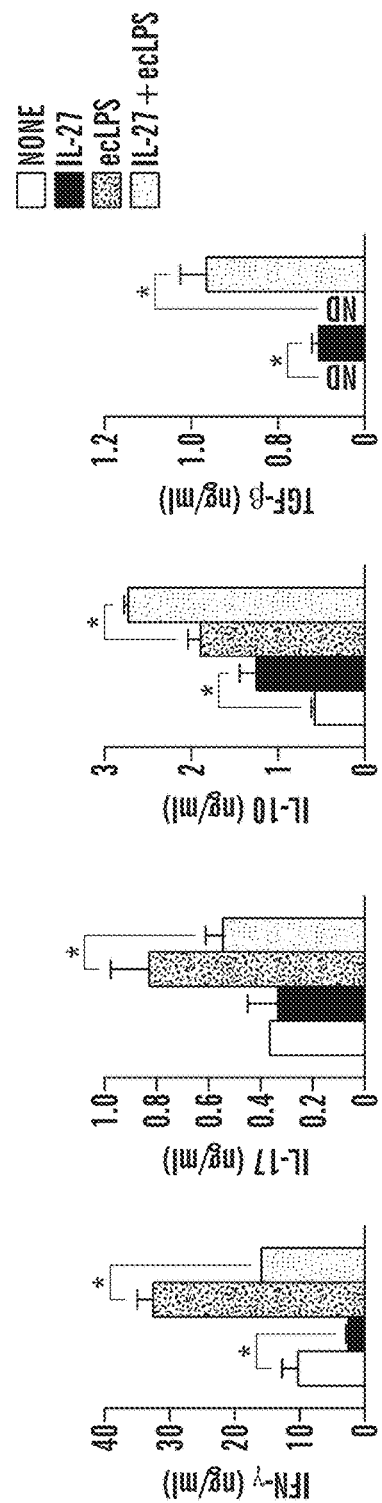
FIG. 3C
FIG. 3D
FIG. 3E

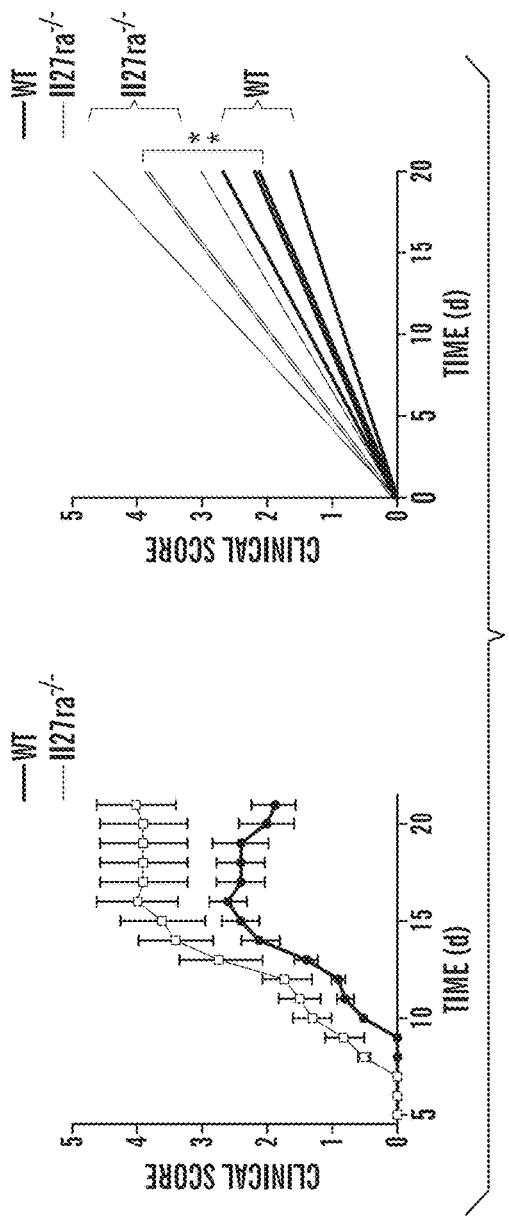
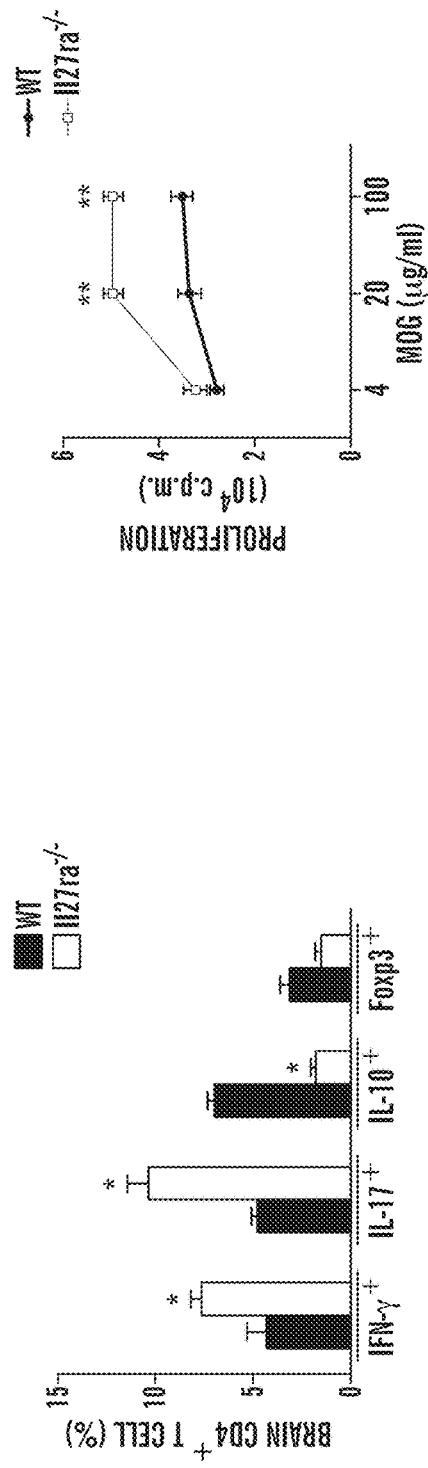
FIG. 4A
FIG. 4B
FIG. 4C

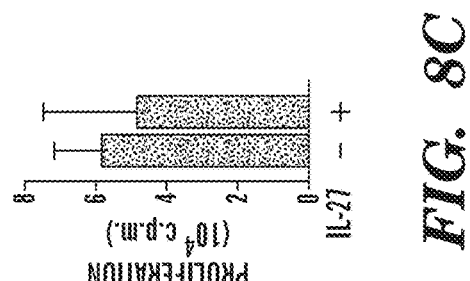
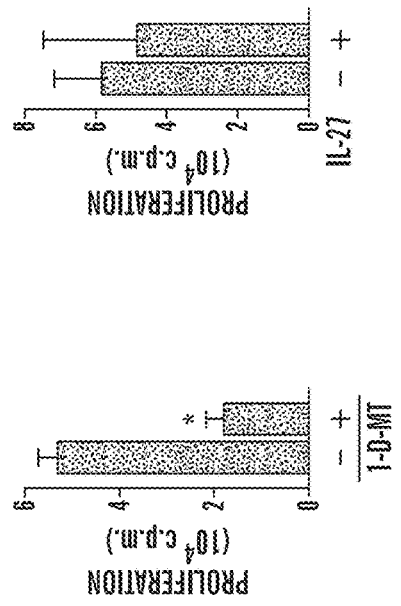
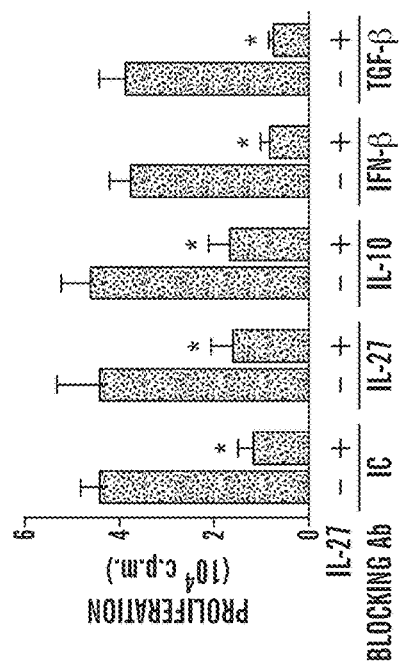
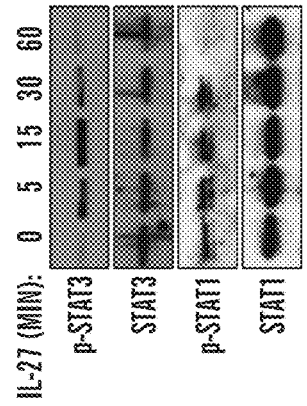
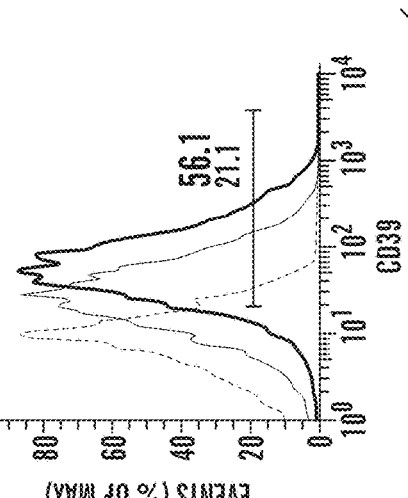
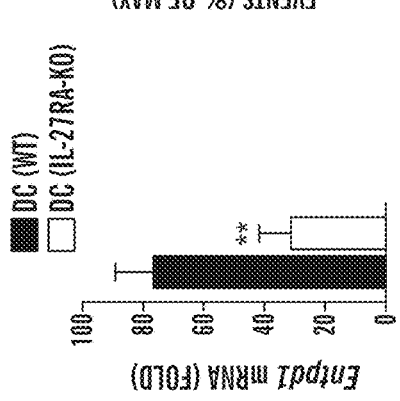

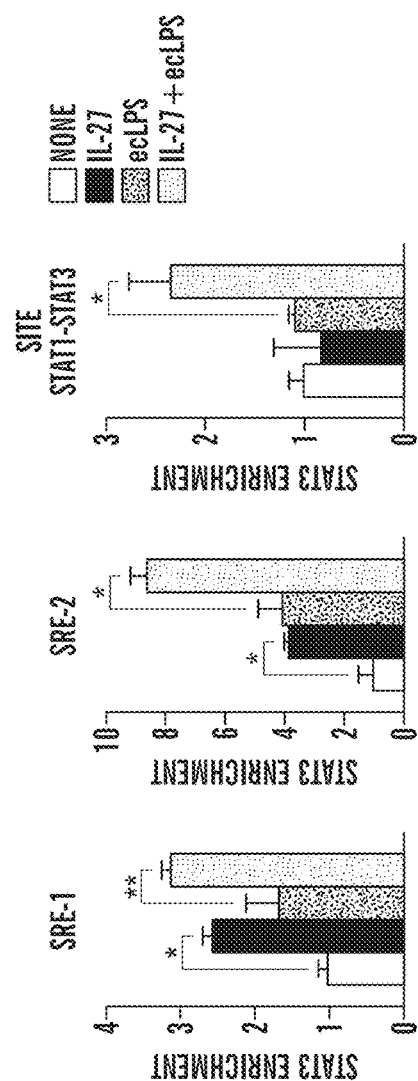
FIG. 8H
FIG. 8I
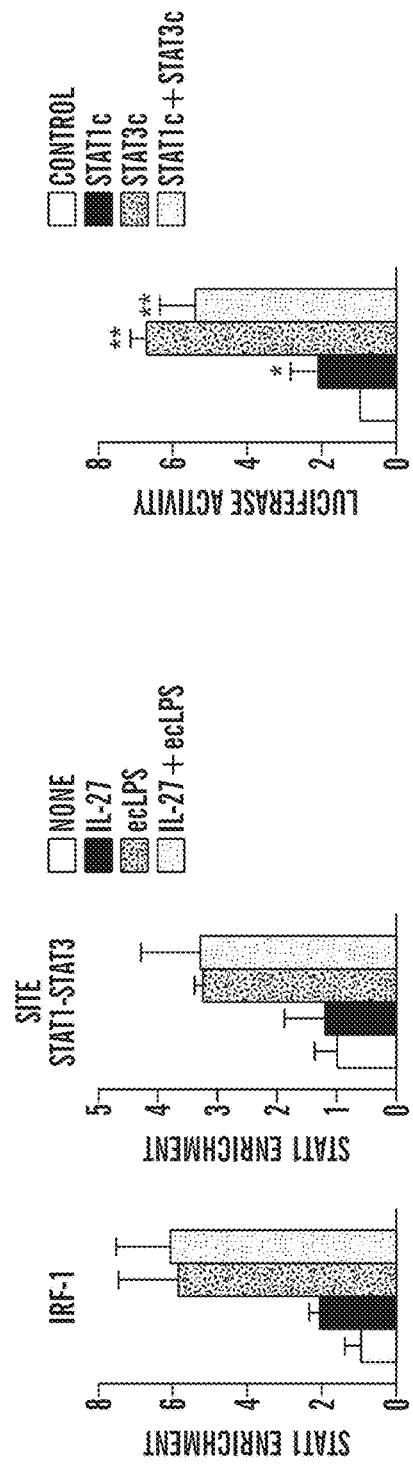
FIG. 8J

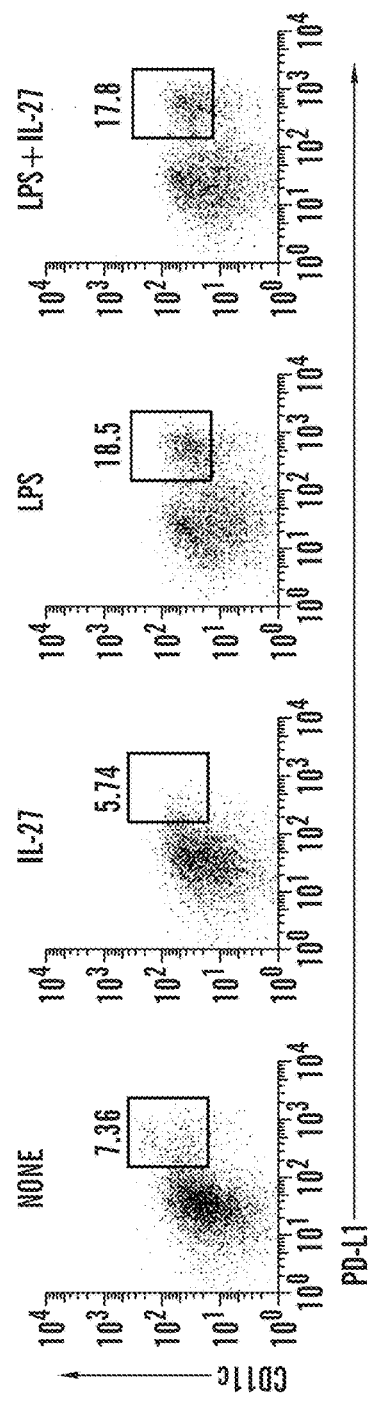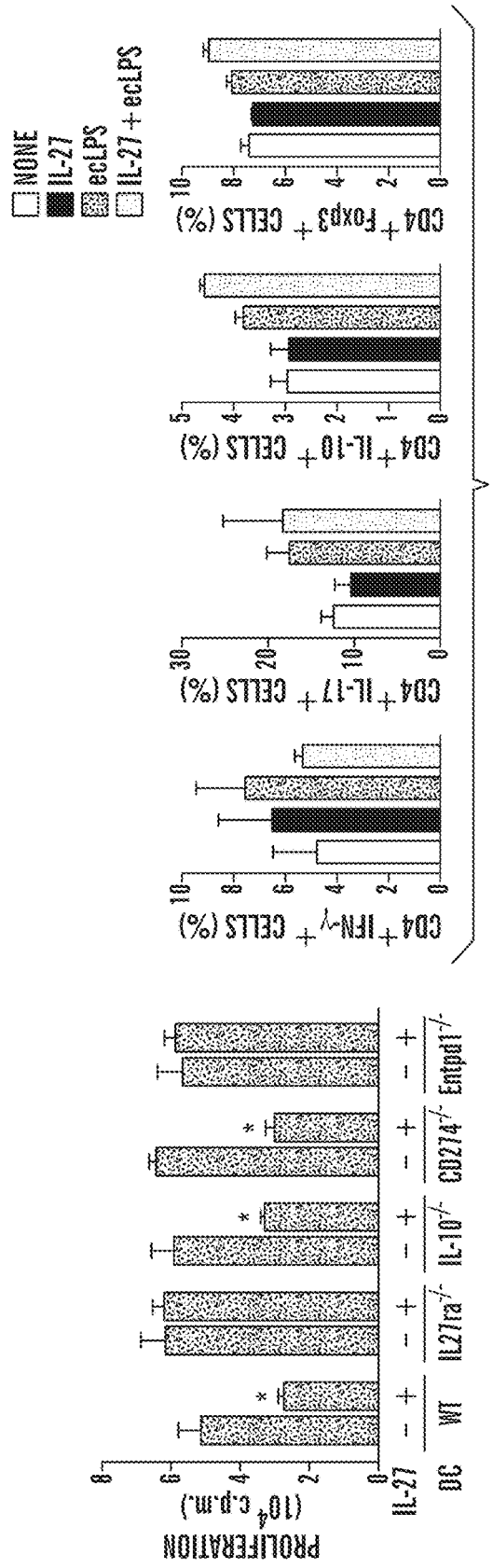
FIG. 9A
FIG. 9B
FIG. 9C

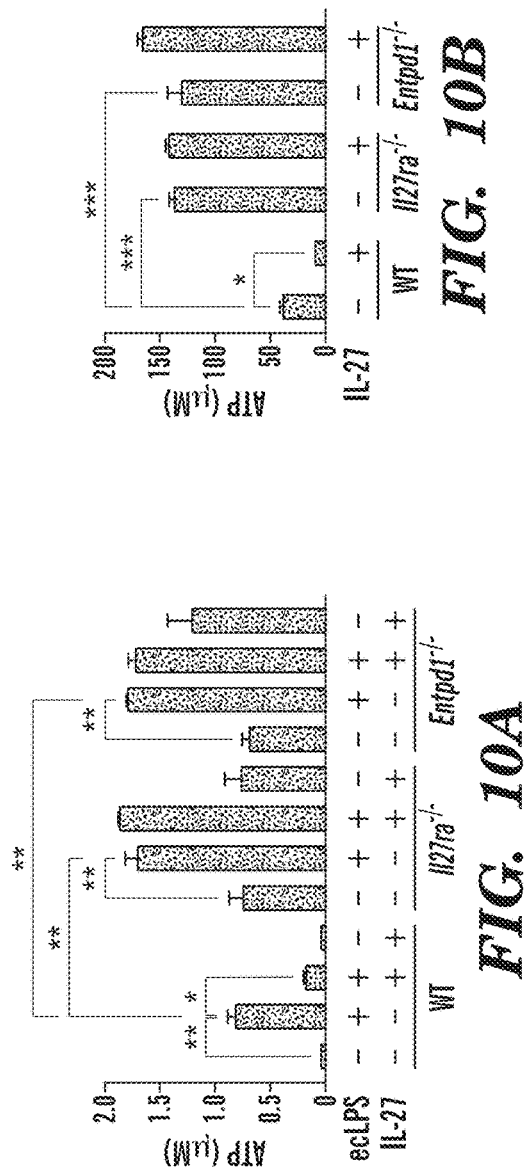
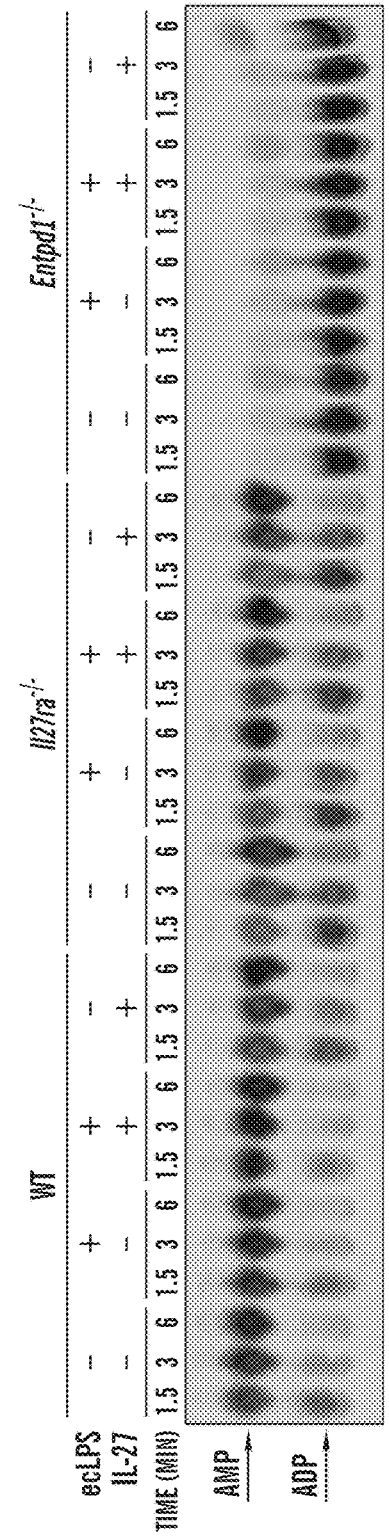
FIG. 10A
FIG. 10B
FIG. 10C

| TREATMENT | n | MAXIMUM SCORE | P VALUE |
|---|---|---|---|
| NONE | 5 | 3.125±0.24 | — |
| DC | 5 | 3.000±0.16 | NS |
| DC+MOG | 5 | 3.300±0.20 | NS |
| DC+IL-27 | 5 | 3.000±0.35 | NS |
| DC+IL-27+MOG | 5 | 1.200±0.34 | 0.05 |
| DC (IL-27RA-KO) +IL-27+MOG | 5 | 3.000±0.93 | NS |
| DC (CD39-KO) +IL-27+MOG | 5 | 3.000±0.74 | NS |
| DC (IL-10-KO) +IL-27+MOG | 5 | 1.100±0.29 | 0.01 |
| DC (PD-L1-KO) +IL-27+MOG | 5 | 1.400±0.37 | 0.05 |

SEQUENCE LISTING

<160> NUMBER OF SEQ ID NOS: 9

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 1

His His His His His His
1               5

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gctgggcttt agagacttgt gggc                                              24

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 3
acccatgcaa atggtttggg ca                                            22

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 4
tgagggccag cccacacttc a                                             21

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 5
gctcactggg tacctcttgc ca                                            22

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 6
ggaacaaaaa tatagagaga acttggga                                      28

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 7
gtagtttgac ctaagtggac atagg                                         25

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 8
aggctcttgt atccttgcca cctct                                         25

```
<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tgatggtgga gtgctgtgtg ctg                                          23
```

METHODS AND COMPOSITIONS OF TREATING AUTOIMMUNE DISEASES

CROSS-REFERENCE TO RELATED APPLICATIONS

This application is a 35 U.S.C. § 371 National Phase Entry Application of International Application No. PCT/US2014/033872 filed Apr. 11, 2014, which designates the U.S., and which claims benefit under 35 U.S.C. § 119(e) of the U.S. Provisional Application No. 61/853,745 filed Apr. 11, 2013, the contents of each of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Oct. 3, 2017, is named 043214-077852-US_SL.TXT, and is 2,353 bytes in size.

TECHNICAL FIELD

Described herein generally relates to methods and compositions for producing a tolerogenic or immunosuppressive dendritic cell. The methods and/or compositions described herein can be used for treating an autoimmune disease or disorder, e.g., but not limited to multiple sclerosis (MS), encephalomyelitis, and type 1 diabetes.

BACKGROUND

The dysregulated activity of effector cells of the TH1 and TH17 subsets of helper T cells results in the development of tissue inflammation and autoimmunity. Myelin-specific TH1 and TH17 cells, for example, contribute to disease pathogenesis in multiple sclerosis (MS) and its animal model, experimental autoimmune encephalomyelitis (EAE). Nylander and Hafler, J. Clin. Invest (2012) 122:1180-188; and Pierson et al. Immunol. Rev. (2012) 248: 205-215. During EAE, dendritic cells (DCs) control the activation and differentiation of myelin-specific effector T cells and regulatory T cells (Treg cells). Bailey et al. Nat. Immunol. (2007) 8:172-180; and Yogev et al. Immunity (2012)37: 264-275. Moreover, DCs isolated from patients with MS generally produce large amounts of TH1- and TH17-polarizing cytokines. Comabella et al. Nat. Rev. Nephrol. (2010) 6: 499-507. DCs control several pathogenic mechanisms associated with the development of central nervous system (CNS) autoimmunity. DCs promote the entry of T cells into the CNS, the activation and differentiation of pathogenic T cells in the CNS, and the spreading of the autoimmune response to new CNS epitopes. Greter et al. Nat. Med. (2005) 11: 328-334; Bailey et al. Nat. Immunol. (2007) 8:172-180; and McMahon et al. Nat. Med. (2005) 11:335-339. Accordingly, there is a need to identify pathways that regulate DC activity during the course of autoimmunity, to identify mechanisms of disease pathogenesis and also to develop new approaches for therapeutic intervention to treat an autoimmune disease.

SUMMARY

Embodiments of various aspects described herein are, in part, based on the discovery that interleukin 27 (IL-27) acts on dendritic cells (DCs) to expand regulatory T cells (Tregs) and/or suppress T cell response (including, e.g., by limiting the generation of effector cells of the Th1 and/or Th17 subsets of helper T cells), which in turn inhibits development of an autoimmune response. The inventors have also discovered that the immunosuppressive effects of IL-27 on DCs are mediated at least in part through induction of the immunoregulatory molecule ectonucleotidase CD39 expression in DCs. Further, the inventors have discovered that CD39 expressed by conventional DCs (cDCs) reduced the extracellular concentration of ATP (eATP) and decreased ATP-triggered activation of the NLRP3 inflammasome. The inventors have also discovered that therapeutic vaccination with IL-27-conditioned DCs can suppress established relapsing-remitting experimental autoimmune encephalomyelitis (EAE). Thus, not only can agents that modulate the activity and/or expression/level of IL-27, IL-27RA, CD39 (or ectonucleotidase CD39), and/or pro-inflammatory eATP be targeted to DCs for treatment of immune-related diseases or disorders such as autoimmune diseases, but IL-27-conditioned DCs can also be administered to a subject for treatment of immune-related diseases or disorders. Accordingly, various aspects described herein provide for methods for generating an immunosuppressive dendritic cell, as well as methods and compositions for treating an immune-related disease or disorder, including, e.g., autoimmune disease.

One aspect provided herein relates to a method of generating an immunosuppressive dendritic cell. The method comprises contacting a dendritic cell with a composition comprising an effective amount of an agent that stimulates or activates an IL-27/ectonucleotidase CD39 axis signaling. The dendritic cell can be obtained or derived from any source. For example, the dendritic cell can be derived from a spleen, lymph node, blood, monocyte, and/or hematopoietic progenitor cell.

The IL-27/ectonucleotidase CD39 axis or IL-27/CD39 axis suppresses proinflammatory immune responses, e.g., via limiting the generation of effector cells of the Th1 and Th17 subsets of helper T cells. As defined herein and throughout the specification, the terms "IL-27/ectonucleotidase CD39 axis" and "IL-27/CD39 axis," as used interchangeably herein, refer to an immunosuppressive pathway of DCs to regulate their antigen presenting function. The immunosuppressive pathway includes IL-27 and ectonucleotidase CD39 (where the terms "ectonucleotidase CD39" and "CD39" are used interchangeably herein), where the immunosuppressive effects of IL-27 on DCs are mediated at least in part through induction of the immunoregulatory molecule ectonucleotidase CD39 expression in DCs. As noted above, the inventors have discovered that CD39 expressed by DCs decreases the extracellular concentration of ATP (eATP) and thus reduces ATP-triggered activation of the NLRP3 inflammasome. Accordingly, in some embodiments, the IL-27/ectonucleotidase CD39 axis can further include an ATP-degrading enzyme, and thus the "IL-27/ectonucleotidase CD39 axis" can refer to an immunosuppressive pathway including IL-27, CD39, and an ATP-degrading enzyme, including, e.g., apyrase.

In some embodiments, the agent that stimulates or activates the IL-27/ectonucleotidase CD39 axis signaling (referred to as "IL-27/CD39 agonistic agent" herein) is an IL-27 agonist. For example, an IL-27 agonist can comprise a recombinant IL-27 protein or peptide. In some embodiments, the IL-27/CD39 agonistic agent is a CD39 agonist. In some embodiments, the IL-27/CD39 agonistic agent is an ATP-degrading enzyme, including, e.g., apyrase.

An IL-27/CD39 agonistic agent can be present in any amount sufficient to generate an immunosuppressive dendritic cell. For example, the effective amount of an IL-27/

CD39 agonistic agent can be sufficient to upregulate the expression of CD39, phosphorylate STAT3, and/or express one or more anti-inflammatory genes (including, e.g., IDO1, IDO2, IL-10, IL-27, A20, TGFβ1, IL-10, and/or IFN-β) in DCs. Methods for detecting and/or measuring these biological molecules or cytokines are known in the art. For example, CD39 or anti-inflammatory gene and/or protein expressions in DCs can be analyzed by quantitative PCR and/or FACS; while phosphorylated STAT3 can be determined by FACS and/or western blot. In some embodiments, the effective amount of the IL-27/CD39 agonistic agent can range from about 1 ng/mL to about 100 ng/mL.

In some embodiments, the method can further comprise contacting the dendritic cell with an autoimmune antigen. The dendritic cell can be contacted with an amount of an autoimmune antigen sufficient to establish tolerance to a specific antigen. In some embodiments, the autoimmune antigen to be contacted with a dendritic cell can have a concentration of about 1 μg/mL to about 100 μg/mL. Non-limiting examples of an autoimmune antigen include myelin basic protein (MBP); proteolipid protein (PLP); myelin oligodendrocyte glycoprotein (MOG), myelin-associated oligodendrocytic basic protein cardiac myosin; outer surface protein (OSP); myelin associated glycoprotein (MAG); neurofilaments; interferon omega; transglutaminase; aromatic acid carboxylase; 17-hydroxylase; 21-hydroxylase, cardiolipin; pyruvate dehydrogenase; β2 glycoprotein I; phosphatidylserine; apoH; Annexin A5; LKM-1; soluble liver antigen; carbonic anhydrase; gpIIb-IIIa or 1b-IX; type XVII collagen; tissue transglutaminase; gliadin; GD1a; GQ1b; BP-1; BP-2; epidermal transglutaminase; histidine-tRNA; signal recognition peptide; Mi-2; Jo1; Glutamic acid decarboxylase, HSP60; HSP70; HSP90; IGRP; insulin; carboxypeptidase H; insulinoma antigen-2; IA-2beta; ICA69; ZnT8; chromogranin A; IAPP; scl70; topoisomerase; histones; Basement Membrane Collagen Type IV; enolase; thyroid peroxidase; thyroglobulin; complement component 3; voltage-gated calcium channels; Q-type calcium channel, synaptogagmin, muscarinic acetylcholine receptor M1; SMA; LKM-1; LKM-2; LKM-3; soluble liver antigen; SLA; LP; major peripheral myelin protein P0; myeloperoxidase; GQ1b; U1-RNP; Kir4.1; nicotinic acetylcholine receptor; MuSK protein; hypocretin; orexin; keratin; AQP4; Yo; Hu; glutamate receptor; Desmoglein 3; p62; sp100; Ro; LA; glycoproteins IIb-IIIa or Ib-IX; ADAMTS13; cardiolipin; $β_2$ glycoprotein I; HPA-1a; HPA-5b; IFN-gamma, IL-1, TNF-alpha; GMCSF, portions thereof, and combinations thereof.

The methods of generating an immunosuppressive dendritic cell as described herein can be performed in a subject, ex vivo or in vitro. Accordingly, in some embodiments, a dendritic cell can be contacted ex vivo or in vitro with a composition comprising an IL-27/CD39 agonistic agent. In alternative embodiments, a dendritic cell can be contacted in vivo with a composition comprising an IL-27/CD39 agonistic agent.

The immunosuppressive dendritic cells generated by the methods described herein are distinct and can be identified from non-treated dendritic cells or other tolerogenic dendritic cells. In some embodiments, the immunosuppressive dendritic cells described herein can comprise an increased expression of IL-27, as compared to dendritic cells not contacted with an IL-27/CD39 agonistic agent (including, e.g., an IL-27 agonist). In some embodiments, the immunosuppressive dendritic cells described herein can comprise an increased expression of CD39, as compared to dendritic cells not contacted with an IL-27/CD39 agonistic agent (including, e.g., an IL-27 agonist). In some embodiments, the immunosuppressive dendritic cells can comprise a reduced production of an effector polarizing cytokine and/or an increased production of an anti-inflammatory cytokine, as compared to dendritic cells not contacted with an IL-27/CD39 agonistic agent (including, e.g., an IL-27 agonist). Exemplary effector polarizing cytokines include, but are not limited to IL-12 and/or IL-6. Exemplary anti-inflammatory cytokine include, but are not limited to TGFβ1, IL-10, IFN-β, or any combinations thereof.

Accordingly, in another aspect, immunosuppressive dendritic cell produced by the methods described herein involving an IL-27/CD39 agonistic agent are also provided herein.

As noted earlier, the inventors have discovered, among other things that, IL-27 acts on DCs to expand Tregs, limit Teffs and suppress autoimmune diseases, e.g., but not limited to type 1 diabetes, multiple sclerosis (MS) and encephalomyelitis in animal models. The anti-inflammatory effects of IL-27 on DCs are mediated at least in part by the up-regulation of the ectonucleotidase CD39 (encoded by ENTPD1) and the consequent decrease in the levels of pro-inflammatory extracellular ATP (eATP). In some immune-related diseases or disorders, e.g., but not limited to autoimmune diseases, it can be desirable to suppress pro-inflammatory responses, e.g., via Th1 and/or Th17 responses for a therapeutic effect. Accordingly, these immune-related diseases or disorders can be treated by targeting the IL-27/CD39 axis in DCs to generate tolerogenic or immunosuppressive DCs.

In some aspects, provided herein are methods of treating an autoimmune disease or disorder. In some embodiments, the methods can be adapted to treat multiple sclerosis. In some embodiments, the methods can be adapted to treat encephalomyelitis. In some embodiments, the methods can be adapted to treat type 1 diabetes. The method of treatment comprises administering to a patient in need thereof a dendritic cell (DC)-targeting composition comprising (i) an agent that stimulates or activates IL-27/ectonucleotidase CD39 axis signaling, and (ii) a DC-binding agent.

In some embodiments, the agent that stimulates or activates the IL-27/ectonucleotidase CD39 axis signaling (referred to as "IL-27/CD39 agonistic agent" herein) is an IL-27 agonist. For example, an IL-27 agonist can comprise a recombinant IL-27 protein or peptide. In some embodiments, the IL-27/CD39 agonistic agent is a CD39 agonist. In some embodiments, the IL-27/CD39 agonistic agent is an ATP-degrading enzyme, including, e.g., apyrase.

An IL-27/CD39 agonistic agent can be present in any amount sufficient to generate an immunosuppressive dendritic cell. For example, the effective amount of an IL-27/CD39 agonistic agent can be sufficient to upregulate the expression of CD39, phosphorylate STAT3, and/or express one or more anti-inflammatory genes (including, e.g., IDO1, IDO2, IL-10, IL-27, A20, TGFβ1, IL-10, and/or IFN-β) in DCs. In some embodiments, the effective amount of the IL-27/CD39 agonistic agent can range from about 1 ng/mL to about 100 ng/mL. In some embodiments, the effective amount of the IL-27/CD39 agonistic agent can range from about 1 ng/kg to about 100 mg/kg, or from about 0.1 mg/kg to about 50 mg/kg.

A DC-binding agent can be any agent or moiety that can target or bind to DCs. In some embodiments, a DC-binding agent is an agent or moiety that specifically targets or binds to DCs. DC-binding agents are known in the art, including, e.g., agents that bind to a DC surface protein or receptor. An exemplary DC-binding agent includes, but is not limited to an antibody against Clec9A and/or DEC205.

In some embodiments, the DC-targeting composition can further comprise at least one or more autoimmune antigens. The amount of an autoimmune antigen present in the DC-targeting composition can be sufficient to establish immune tolerance to a specific antigen in a subject in need thereof. For example, the amount of an autoimmune antigen in the DC-targeting composition can range from about 1 µg/mL to about 100 µg/mL. In some embodiments, the amount of an autoimmune antigen in the DC-targeting composition can range from about 0.1 µg/kg to about 500 mg/kg, or from about 0.5 mg/kg to about 250 mg/kg. Non-limiting examples of an autoimmune antigen include myelin basic protein (MBP); proteolipid protein (PLP); myelin oligodendrocyte glycoprotein (MOG), myelin-associated oligodendrocytic basic protein cardiac myosin; outer surface protein (OSP); myelin associated glycoprotein (MAG); neurofilaments; interferon omega; transglutaminase; aromatic acid carboxylase; 17-hydroxylase; 21-hydroxylase, cardiolipin; pyruvate dehydrogenase; β2 glycoprotein I; phosphatidylserine; apoH; Annexin A5; LKM-1; soluble liver antigen; carbonic anhydrase; gpIIb-IIIa or 1b-IX; type XVII collagen; tissue transglutaminase; gliadin; GD1a; GQ1b; BP-1; BP-2; epidermal transglutaminase; histidine-tRNA; signal recognition peptide; Mi-2; Jo1; Glutamic acid decarboxylase, HSP60; HSP70; HSP90; IGRP; insulin; carboxypeptidase H; insulinoma antigen-2; IA-2beta; ICA69; ZnT8; chromogranin A; IAPP; scl70; topoisomerase; histones; Basement Membrane Collagen Type IV; enolase; thyroid peroxidase; thyroglobulin; complement component 3; voltage-gated calcium channels; Q-type calcium channel, synaptogagmin, muscarinic acetylcholine receptor M1; SMA; LKM-1; LKM-2; LKM-3; soluble liver antigen; SLA; LP; major peripheral myelin protein P0; myeloperoxidase; GQ1b; U1-RNP; Kir4.1; nicotinic acetylcholine receptor; MuSK protein; hypocretin; orexin; keratin; AQP4; Yo; Hu; glutamate receptor; Desmoglein 3; p62; sp100; Ro; LA; glycoproteins IIb-IIIa or Ib-IX; ADAMTS13; cardiolipin; $\beta_2$ glycoprotein I; HPA-1a; HPA-5b; IFN-gamma, IL-1, TNF-alpha; GMCSF, portions thereof, and combinations thereof.

The DC-targeting composition acts as an immunomodulator that preferentially or specifically targets or binds DCs, and can be present in any appropriate format. For example, a DC-targeting composition can be a fusion protein comprising a DC-binding agent and at least one or more IL-27/CD39 agonistic agents described herein.

Additionally or alternatively, the DC-targeting composition can be formulated in the form of nanoparticle(s). The IL-27/CD39 agonistic agent, DC-binding agent, and/or optional autoimmune antigen can distribute on a surface of the nanoparticle(s) or be encapsulated in the nanoparticle(s). In some embodiments, the DC-binding agent can form on the surface of the nanoparticle(s) while one or more IL-27/CD39 agonistic agents and optional autoimmune antigen(s) can be encapsulated in the nanoparticle(s), which can be released therefrom to DCs.

In some embodiments, the nanoparticle(s) can further comprise on its surface a biocompatible layer. The biocompatible layer can prolong the half-time of the nanoparticles in a subject. In one embodiment, the nanoparticle(s) can further comprise on its surface a PEG layer.

Generally, nanoparticles administered to a subject can be made of any biocompatible material. In one embodiment, the nanoparticles are gold nanoparticles.

In another aspect, dendritic cells can be pre-treated with one or more IL-27/CD39 agonistic agents as described herein (including, e.g., IL-27 agonists) to generate immunosuppressive dendritic cells, which can then be administered or transplanted to a subject in need thereof, e.g., a subject diagnosed with an autoimmune disease or disorder. Accordingly, also provided herein is a method of treating an autoimmune disease or disorder comprising administering to or placing in a subject in need thereof a composition comprising a population of immunosuppressive dendritic cells that are generated by contacting dendritic cells with at least one or more IL-27/CD39 agonistic agents (including, e.g., IL-27 agonists).

In some embodiments, the population of immunosuppressive dendritic cells are autologous dendritic cells. Thus, in some embodiments, the method can further comprise obtaining dendritic cells from a sample of a subject. The sample can be a tissue biopsy from a spleen or lymph node, or a blood sample. The autologous dendritic cells can then be pre-treated ex vivo with at least one or more IL-27/CD39 agonistic agents (including, e.g., IL-27 agonists), followed by transplantation into the subject.

In some embodiments, the composition comprising immunosuppressive dendritic cells can further comprise an autoimmune antigen as described herein. The autoimmune antigen can be administered prior to, concurrently with, or after the administration or placement of the composition comprising immunosuppressive dendritic cells at a target tissue or organ site of a subject.

It is contemplated that in other immune-related diseases or disorder, including, e.g., cancer, it can be desirable to induce proinflammatory responses, e.g., Th1/Th17 responses, at a target site (e.g., a tumor) for a therapeutic effect. Accordingly, these immune-related diseases or disorders, e.g., but not limited to cancer, where upregulation of immune response is desirable, can be treated by suppressing the IL-27/CD39 axis signaling. For example, in some embodiments, a subject who is diagnosed with cancer can be administered with a DC-targeting composition comprising a DC-binding agent and an agent that suppresses IL-27/CD39 axis signaling (also referred to as "IL-27/CD39 antagonistic agent").

It is also contemplated that other inflammatory diseases or disorders, including, e.g., allergy and asthma, where a dampening Th2 response is desirable could be treated by downregulating or suppressing the IL-27/CD39 axis signaling.

BRIEF DESCRIPTION OF THE DRAWINGS

FIGS. 2A-2C show IL-27RA expression in DCs. Flow cytometry (FIG. 2A), quantitative PCR (FIG. 2B) and immunoblot analysis (FIG. 2C) of IL-27RA expression in sorted cDCs and pDCs. Numbers above bracketed line (FIG. 2A) indicate percent IL-27RA+ cDCs (red) and pDCs (blue); dotted line, isotype-matched control antibody. Actin serves as a loading control throughout. WT, wild-type. *P<0.05 (Student's t-test). Data are representative of more than three independent experiments with similar results (error bars (FIG. 2B), s.e.m.).

FIGS. 3A-3I show that IL-27 modulates the antigen-presenting function of cDCs. (FIG. 3A) Flow cytometry of wild-type cDCs left untreated (None) or treated with IL-27 (20 ng/ml) or ecLPS (100 ng/ml) alone or sequentially, presented as mean fluorescence intensity (MFI). MHCII, MHC class II. (FIG. 3B) Enzyme-linked immunosorbent assay of cytokines in culture supernatants of cDCs treated as in a. (FIG. 3C) Quantitative PCR analysis of Il27 mRNA in cDCs treated as in a, presented relative to that of the control gene Gapdh. ND, not detected. (FIGS. 3D-3F) Proliferation (FIG. 3D), cytokines in culture supernatants (FIG. 3E) and frequency of CD4+ IFN-γ+, IL-17+, IL-10+ and Foxp3+ cells (FIG. 3F) among naive 2D2 CD4+ T cells stimulated with MOG(35-55) plus cDCs treated as in FIG. 3A. (FIGS. 3G-3H) Cytokine secretion (FIG. 3G) and frequency of Foxp3+ CD4+ T cells (FIG. 3H) among naive 2D2 CD4+ T cells stimulated with MOG(35-55) plus cDCs treated as in FIG. 3A, in the presence of exogenous cytokines to promote the differentiation of TH1, TH17 and Tr1 cells (FIG. 3G) or Foxp3+ T cells (FIG. 3H). Numbers in outlined areas (FIG. 3H, left) indicate percent Foxp3+ CD4+ T cells. *P<0.05 and **P<0.01 (one-way analysis of variance (ANOVA)). Data are from three independent experiments (FIG. 3A-3H, right; mean and s.e.m.) or are representative of three independent experiments (FIG. 3H, left). (FIG. 3I) IL-27 signaling in DCs modulates MHC-II and co-stimulatory molecule expression in DCs. Flow cytometry analysis of ecLPS-treated cDC in the presence or absence of IL-27. Representative histograms of three independent experiments, the staining obtained with isotype control antibodies is shown in gray.

FIGS. 4A-4E show that IL-27 limits effector T-cell differentiation and EAE development. (FIG. 4A) Development of EAE in WT and Il-27ra$^{-/-}$ mice, clinical score (left panel) and linear-regression curves of disease for each group (dashed lines indicate 95% confidence intervals). (FIG. 4B) CNS-infiltrating CD4+ T cells analyzed for the expression of IFN-γ, IL-17, IL-10 and Foxp3 by flow cytometry. (FIG. 4C) Recall response to MOG (35-55) in splenocytes from WT and Il-27ra$^{-/-}$ mice isolated 21 days after EAE induction. (FIG. 4D) Frequency of CD4+CD44+CD40L$^{hi}$ splenic IFN-γ+, IL-17+, IFN-γ+IL-17+ (DP), IL-10+ and Foxp3+CD4+ T cells in WT and Il-27ra$^{-/-}$ mice 21 days after EAE induction. (FIG. 4E) Naive CFSE labeled 2D2+ CD4+ T cells were stimulated with MOG (35-55) and cDCs sorted from WT and Il-27ra$^{-/-}$ mice 21 days after immunization, and T-cell proliferation was analyzed. The frequency of proliferated cells is shown in the histogram and the proliferation index is shown in the right (FIG. 4E). Numbers within histograms show the percentage of positive cells. Shown is a representative experiment (of three) with n≥5 mice/group. *P<0.05 and **P<0.01 (Student's t-test).

(FIG. 5A) Lethally irradiated WT mice were reconstituted with bone marrow (BM) from mice expressing the diphtheria toxin receptor (DTR) under the control of the CD11c (itgax) promoter (CD11c-DTR mice). Following reconstitution, DCs were depleted by the administration of diphtheria toxin (DTx) and DCs compartment was reconstituted with DC precursors from WT (Cx3Cr1$^-$GFP$^{+/-}$WT) or Il-27ra$^{-/-}$ (Cx3Cr1$^-$GFP$^{+/-}$Il-27ra$^{-/-}$) mice. (FIG. 5B) Representative flow cytometry analysis of DCs precursors (CDPs). (FIG. 5C) Antibodies against Diphtheria toxin (DT) in serum from DC (WT) and DC (IL-27RA-KO) mice. (FIG. 5D) Expression of IL27ra in cDCs, Ly6C$^{lo}$ and Ly6C$^{hi}$ monocytes sorted from naive DC (WT) and DC (IL-27RA-KO) mice, analyzed by qPCR. (FIG. 5E) Frequency (left panel) and absolute numbers of cDCs and pDCs in spleens from DC (WT) and DC (IL-27RA-KO) mice. (FIGS. 5F-5H) Passive transfer EAE in DC (WT) and DC (IL-27RA-KO) recipients. 2D2 mice were immunized with MOG (35-55) and 7 d after immunization T cells were cultured with MOG (35-55) in the presence of IL-12 or IL-23 and 48 h after re-stimulation IL-17 and IFN-γ secreted into the cell culture medium were determined by ELISA (FIG. 5F). Following transfer of TH1 or TH17 polarized T cells into in DC (WT) and DC (IL-27RA-KO) mice, the development of EAE was monitored in the recipient mice. Clinical score (left panel) and linear-regression curves of disease for each group (dashed lines indicate 95% confidence intervals) (FIG. 5G). CNS-infiltrating CD4+ T cells analyzed for the expression of IFN-γ and IL-17, IL-10 by flow cytometry (FIG. 5H). **P<0.01 (One-way ANOVA and student's t-test) versus DC (WT). Data are representative of at least three independent experiments.

(FIG. 6A) Flow cytometry of IL-27RA in splenic cDCs sorted from naive DC(WT) or DC(IL-27RA-KO) mice. Numbers above bracketed line indicate percent IL-27RA+ DC(WT) cDCs (black) or DC(IL-27RA-KO) cDCs (red); dotted line, isotype-matched control antibody. (FIG. 6B) Development of EAE in DC(WT) and DC(IL-27RA-KO) mice, presented as clinical score (left) and linear-regression curves (right; thinner lines indicate 95% confidence interval). (FIG. 6C) Frequency of IFN-γ+, IL-17+, IL-10+ and Foxp3+ cells among CNS-infiltrating CD4+ T cells, analyzed by flow cytometry. (FIG. 6D) Recall response to MOG(35-55) (MOG) by splenocytes isolated from DC(WT) and DC(IL-27RA-KO) mice 21 d after EAE induction. (FIG. 6E) Frequency of CD4+ CD44+ CD40L$^{hi}$ splenic IFN-γ+, IL-17+, IFN-γ+ IL-17+ (DP), IL-10+ and Foxp3+ CD4+ T cells in DC(WT) and DC(IL-27RA-KO) mice 21 d after EAE induction. Numbers in quadrants or adjacent to outlined areas indicate percent cells in each throughout. (FIG. 6F) Expression of Il27ra, Il6, Il12a, Il23a, Il27, Ifnb1, Il10 and Tgfb1 mRNA in cDCs sorted from DC(WT) and DC(IL-27RA-KO) mice 21 d after EAE induction, presented relative to that of Gapdh. (FIG. 6G) Quantitative expression profiling of cDCs isolated from DC(WT) and DC(IL-27RA-KO) mice 21 d after EAE induction, presented relative to that of endogenous control genes. (FIGS. 6H-6I) Proliferation (FIG. 6H) and cytokine secretion (FIG. 6I) of naive 2D2 CD4+ T cells labeled with the division-tracking dye CFSE and stimulated with MOG(35-55) plus cDCs sorted from DC(WT) and DC(IL-27RA-KO) mice 21 d after EAE induction. Numbers above plots (FIG. 6H, left) indicate percent CFSE+ (proliferated) cells; green line (FIG. 6H), unproliferated cells. *P<0.05, P<0.01 and *P<0.001, compared with DC(WT) (Student's t-test). Data are from one experiment representative of three experiments with five or more mice per group (error bars (FIG. 6B-6I), s.e.m.).

(FIGS. 7A-7B) Ingenuity Pathway Analysis (IPA) of the transcriptional effects of IL-27 in DCs identified significant effects of IL-27 on NF-kB (FIG. 7A) and Toll-like Receptor (FIG. 7B) signaling pathways. In NF-kB and Toll-like Receptor Signaling pathways, green shaded regions indicate down-regulation and red shaded regions indicate up-regulation of genes. (FIG. 7C) Time course of Ido1 and Ido2, Entpd1, Il27, Il10, Tnip3, Tnfaip3, Ramp3 and Esr1 expression measured by quantitative real-time PCR in cDCs treated with IL-27 for 0, 2, 6, and 24 h. Results are shown relative to the expression of mRNA encoding Gapdh. (FIG. 7D) Computational model of the effects of IL-27 on DCs generated with NetGenerator. Integrated interactions in splenic IL-27-treated cDCs compared with untreated cDCs are shown. Black edges denote inferred connections without prior knowledge, green edges present an agreement, and grey dashed edges stand for prior knowledge not reproduced in the inferred network. *P<0.05 and **P<0.01 (One-way ANOVA) compared with untreated cDCs (Time 0).

FIGS. 8A-8J show that CD39 is required for the inhibitory effects of IL-27 on DCs. (FIGS. 8A-8B) Proliferation of naive CD4+ T cells stimulated with anti-CD3 plus wild-type cDCs treated with ecLPS alone (−) or pretreated with IL-27 and treated with ecLPS (+), in the presence of isotype-matched control antibody (IC) or blocking antibody (Ab) to IL-27, IL-10, IFN-γ or TGF-β (FIG. 8A) or in the presence (+) or absence (−) of 1-D-MT (FIG. 8B). (FIG. 8C) Proliferation of T cells stimulated with anti-CD3 plus DC(CD39-KO) cDCs treated with ecLPS alone or pretreated with IL-27 and treated with ecLPS. (FIG. 8D) Quantitative PCR analysis of Entpd1 mRNA (left) and flow cytometry of CD39 (right) in cDCs sorted from naive DC(WT) and DC(IL-27RA-KO) mice; mRNA results are relative to that of Gapdh. Numbers above bracketed lines (right) indicate percent CD39+ cells; dotted line, isotype-matched control antibody. (FIGS. 8E-8F) Immunoblot analysis (FIG. 8E) and flow cytometry (FIG. 8F) of phosphorylated (p-) and total STAT1 and STAT3 in splenic cDCs exposed for various times to IL-27 (20 ng/ml). (FIG. 8G) STAT1-binding site (green; IRF-1), STAT3-binding sites (blue; SRE-1 and SRE-2) and STAT1-STAT3-binding site (green-blue) in the Entpd1 promoter. (FIGS. 8H-8I) Chromatin-immunoprecipitation analysis of the interaction of STAT3 (FIG. 8H) or STAT1 (FIG. 8I) with various binding sites of the Entpd1 promoter as in g (above graphs) in cDCs left untreated (None) or treated with IL-27 or ecLPS alone or sequentially. (FIG. 8J) Luciferase activity in HEK293 cells transfected with a CD39 luciferase reporter alone (Control) or together with a construct encoding constitutively activated STAT1 (STAT1c) or STAT3 (STAT3c) separately or together (STAT1c+STAT3c). *P<0.05 and **P<0.01 (one-way ANOVA). Data are representative of more than three independent experiments with similar results (error bars (FIGS. 8A-8D, 8F, and 8H-8J), s.e.m.).

FIGS. 9A-9E show that ENTPD1 is required for the effects of IL-27 on DCs. (FIG. 9A) PD-L1 expression in IL-27-treated cDC in the presence or absence of ecLPS. Numbers adjacent to outlined areas indicate percentage of CD11c PD-L1 positive cells. (FIG. 9B) Naive CD4+ T cells were stimulated with anti-CD3 and ecLPS− or ecLPS+ IL-27-treated WT, Il27ra−, Il10−, CD274 (PD-L1)− or Entpd1 (CD39)-deficient cDCs and proliferation was analyzed. (FIG. 9C) Naive CD4+ T cells were stimulated with anti-CD3 and ecLPS− or ecLPS+IL-27-treated Entpd1-deficient cDCs and the differentiation of IFNγ+, IL-17+, IL-10+ and Foxp3+ T cells was analyzed by flow cytometry. (FIG. 9D) Entpd1 expression in cDCs, Ly6C$^{lo}$ and Ly6C$^{hi}$ monocytes sorted from naive DC (WT) and DC (CD39-KO) mice, analyzed by qPCR. (FIG. 9E) Frequency (left panel) and absolute numbers of cDCs and pDCs in spleens from DC (WT) and DC (CD39-KO) mice. *P<0.05; **P<0.01 (One-way ANOVA). Data are representative of at least three independent experiments FIGS. 10A-10F show that IL-27-induced CD39 controls extracellular ATP and activation of the NLRP3 inflammasome. (FIG. 10A) Extracellular ATP concentration in culture supernatants of wild-type (WT), IL-27RA-deficient (Il27ra$^{-/-}$) or CD39-deficient (Entpd1$^{-/-}$) cDCs treated with IL-27 or ecLPS alone or sequentially. (FIG. 10B) Residual extracellular ATP in culture supernatants of cDCs treated with ecLPS in the presence (+) or absence (−) of LPS after incubation with 500 μM exogenous ATP. (FIG. 10C) Thin-layer chromatography assay of the enzymatic activity of CD39 in cDCs as in FIG. 10A. (FIG. 10D) Quantification of AMP band intensity, presented in arbitrary units (AU) relative to that of ADP in CD39-deficient cDCs treated as in FIG. 10A. (FIG. 10E) Immunoblot analysis (left) and densitometry (right) of caspase-1 and IL-1β in cDCs as in FIG. 10A. (FIG. 10F) Quantification of IL-1β in culture supernatants of cDCs as in FIG. 10A. *P<0.05, P<0.01 and *P<0.001 (one-way ANOVA). Data are representative of two independent experiments with similar results (error bars (FIGS. 10A-10B, and 10D-10F), s.e.m.).

(FIG. 11A) Flow cytometry of CD39 in splenic DC sorted from naive DC(WT) or DC(CD39-KO) mice. Numbers above bracketed line (FIG. 11A) indicate percent CD39+ DC(WT) cDCs (black) or DC(CD39-KO) cDCs (red); dotted line, isotype-matched control antibody. (FIG. 11B) Development of EAE in DC(WT) and DC(CD39-KO) mice (presented as in FIG. 6B). (FIG. 11C) Frequency of IFN-γ+, IL-17+, IL-10+ and Foxp3+ cells among CNS-infiltrating CD4+ T cells, analyzed by flow cytometry. (FIG. 11D) Recall response to MOG(35-55) in splenocytes isolated from DC(WT) and DC(CD39-KO) mice 21 d after EAE induction. (FIG. 11E) Frequency of CD4+ CD44+ CD40L$^{hi}$ splenic IFN-γ+, IL-17+, IFN-γ+ IL-17+ (DP), IL-10+ and Foxp3+ CD4+ T cells in DC(WT) and DC(CD39-KO) mice 21 d after EAE induction. (FIG. 11F) Expression of Entpd1, Il6, Il12a, Il23a, Il27, Ifnb1, Il10 and Tgfb1 in cDCs sorted from DC(WT) and DC(CD39-KO) mice 21 d after EAE induction, presented relative to that of Gapdh. (FIGS. 11G-11H) Proliferation (FIG. 11G) and cytokine secretion (FIG. 11H) of naive CFSE-labeled 2D2 CD4+ T cells stimulated with MOG(35-55) plus cDCs sorted from DC(WT) and DC(CD39-KO) mice 21 d after immunization (results in g presented as in FIG. 6H). *P<0.05 and **P<0.01, compared with DC(WT) (Student's t-test). Data are from one experiment representative of three experiments with five or more mice per group (error bars (FIGS. 11B-11H), s.e.m.).

(FIG. 12A) The course of EAE is shown as the mean EAE score ±SEM (n=5 mice per group) for the whole observation period (left panel), and also as the linear regression curves of the disease for each group from day 20 until the termination of the experiment. Arrows indicate DC vaccine administration. (FIG. 12B-12D) EAE was induced by immunization of naive B6 mice with MOG (35-55), and DCs were administered i.v. 4 times, once every 4 days, starting at day 10 after EAE induction. (FIGS. 12B & 12C) The course of EAE is shown as the mean EAE score ±SEM (n=5 mice per group) for the whole observation period (left panel), and also as the linear regression curves of the disease for each group. Arrows indicate DC vaccine administration. (FIG. 12D) Effects of therapeutic DC vaccination on B6 EAE. (FIGS. 12E & 12F) Recall proliferative and cytokine response to MOG (35-55) in splenocytes taken from DCs-treated mice 21 days after EAE induction. Data are representative of at least three independent experiments. NS, not significant. *P<0.05, P<0.01 and P<0.001 (One-way ANOVA) versus control mice.

(FIG. 13A) Course of EAE induced by no treatment (None) or immunization of naive SJL mice with PLP(131-151) alone (DC+PLP) or IL-17 alone (DC+IL-27) or both (DC+IL-27+PLP), followed by intravenous administration of DCs (downward arrows) four times once every 4 d starting at day 20, presented as clinical scores for the entire observation period (left) and as linear-regression curves from day 20 until the termination of the experiment (right). (FIGS. 13B-13E) Recall proliferative response (FIGS. 13B and 13D) and cytokine response (FIGS. 13C and 13E) to PLP(131-151) (FIGS. 13B-13C) or PLP(178-191) (FIGS. 13D-13E) in splenocytes obtained from DC-treated mice 55 d after EAE induction as in FIG. 13A. (FIG. 13F) Heat map of the antibody response to myelin antigens (right margin) on day 55 after EAE induction as in FIG. 13A (assessed by antigen microarray); each column represents the mean serum reactivity of immunoglobulin G (IgG) to each treatment condition (key, below). *P<0.05, P<0.01 and *P<0.001, versus untreated control mice (one-way ANOVA). Data are representative of at least three independent experiments (mean and s.e.m. of five mice per group in FIG. 13A; error bars (FIGS. 13B-13E), s.e.m.)

(FIG. 14A) eATP activates the NLRP3 inflammasome in DCs and promotes Teff differentiation. (FIG. 14B) ENTPD1 (CD39) induced by IL-27 degrades eATP, limits Teff differentiation and promotes Treg generation. (FIG. 14C) Biotherapeutics of DC-targeting antibodies fused to IL-27 or apyrase promote Treg generation and limit Teff differentiation.

DETAILED DESCRIPTION OF THE INVENTION

Figure 1:
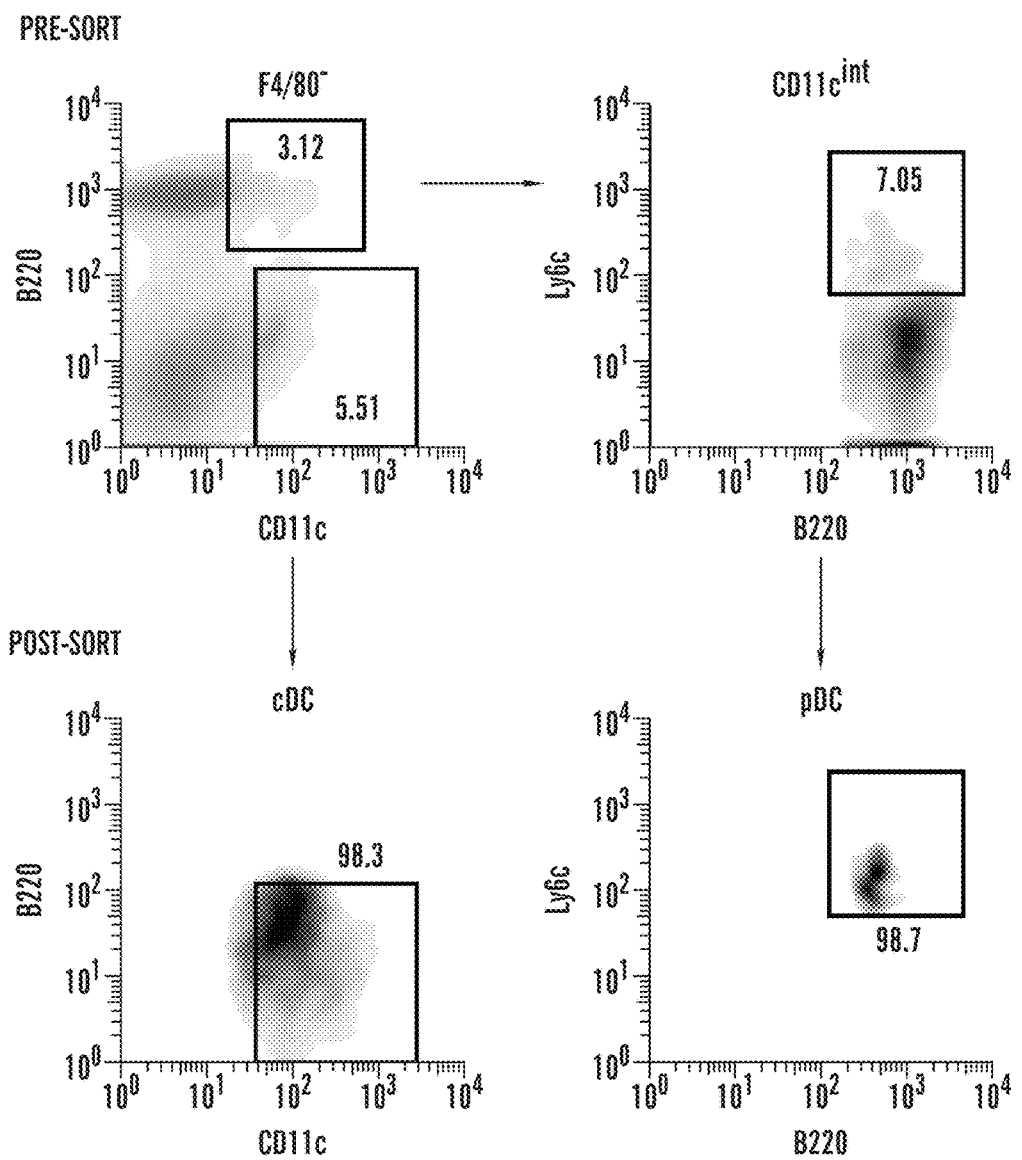
FIG. 1 shows fluorescence-activated cell sorting of DCs. Splenic DCs were stained for F4/80, CD11b, CD11c, B220, MHCII and Ly6c and sorted by flow cytometry into F4/80$^-$ CD11b$^-$ CD11c$^{low}$ B220$^+$ MHC-II$^-$ Ly6c$^+$ pDCs and F4/80$^-$ CD11b$^+$ CD11c$^+$ B220$^-$ MHC-II$^+$ Ly6c$^-$ cDCs. Numbers adjacent to outlined areas indicate percentage of positive cells. Data are from one of more than 3 independent experiments with similar results.

Embodiments of various aspects described herein are, in part, based on the discovery that interleukin 27 (IL-27) acts on dendritic cells (DCs) to expand regulatory T cells (Tregs) and/or suppress T cell response (including, e.g., by limiting the generation of effector cells of the Th1 and/or Th17 subsets of helper T cells), which in turn inhibits development of an autoimmune response. The inventors have also discovered that the immunosuppressive effects of IL-27 on DCs are mediated at least in part through induction of the immunoregulatory molecule ectonucleotidase CD39 expression in DCs. Further, the inventors have discovered that CD39 expressed by conventional DCs (cDCs) reduced the extracellular concentration of ATP (eATP) and decreased ATP-triggered activation of the NLRP3 inflammasome. The inventors have also discovered that therapeutic vaccination with IL-27-conditioned or IL-27-treated DCs can suppress established relapsing-remitting experimental autoimmune encephalomyelitis (EAE). Thus, not only can agents that modulate the activity and/or expression/level of IL-27, IL-27RA, CD39 (or ectonucleotidase CD39), and/or pro-inflammatory eATP be targeted to DCs for treatment of immune-related diseases or disorders such as autoimmune diseases, but IL-27-conditioned or IL-27-treated DCs can also be administered to a subject for treatment of immune-related diseases or disorders such as autoimmune diseases or disorders. Accordingly, various aspects described herein provide for methods for generating an immunosuppressive dendritic cell, as well as methods and compositions for treating an immune-related disease or disorder, including, e.g., autoimmune disease.

Immunosuppressive Dendritic Cells and Methods of Generating the Same

One aspect provided herein relates to a method of generating an immunosuppressive dendritic cell. The method comprises contacting a dendritic cell with a composition comprising an effective amount of an agent that stimulates or activates an IL-27/ectonucleotidase CD39 axis signaling. The dendritic cell can be obtained or derived from any source. For example, the dendritic cell can be derived from a spleen, lymph node, blood, monocyte, and/or hematopoietic progenitor cell.

DCs are antigen presenting cells (APC) that control the activation and/or polarization of T cells into specific lineages. The interplay between T cell lineages regulates the development of an autoimmune disease or disorder, e.g., but not limited to multiple sclerosis, autoimmune encephalomyelitis, and diabetes. DCs express a functional IL-27 receptor (18); however, the physiological relevance of IL-27 signaling in DCs and its effects on the control of the T cell response and autoimmunity are unknown. In accordance with various aspects described herein, an agent that stimulates or activates an IL-27/CD39 axis signaling can act on DCs to suppress the T cell response and autoimmunity.

As used herein and throughout the specification, the phrase "agent that stimulates or activates an IL-27/ectonucleotidase CD39 axis signaling" or "IL-27/CD39 agonistic agent," as used interchangeably herein, refers to an agent that induces immunosuppression mediated by the IL-27/CD39 axis signaling as defined earlier. The IL-27/CD39 axis suppresses proinflammatory immune responses or induces immunosuppression, e.g., via limiting generation of effector cells of the Th1 and Th17 subsets of helper T cells. As noted above, the inventors have discovered that CD39 expressed by DCs decreases the extracellular concentration of ATP (eATP) and thus reduces ATP-triggered activation of the NLRP3 inflammasome, as well as promoting Treg (regulatory T cell) generation and/or limiting Teff (effector T cell) differentiation.

In some embodiments, the IL-27/CD39 agonistic agent to be contacted with a dendritic cell can be an IL-27 agonist. For example, an IL-27 agonist can comprise a recombinant IL-27 protein or peptide. In some embodiments, the IL-27/CD39 agonistic agent can be a CD39 agonist. In some embodiments, the IL-27/CD39 agonistic agent can be an ATP-degrading enzyme, including, e.g., apyrase.

An IL-27/CD39 agonistic agent can be present in any amount sufficient to generate an immunosuppressive dendritic cell. For example, the effective amount of an IL-27/CD39 agonistic agent can be sufficient to upregulate the expression of CD39, phosphorylate STAT3, and/or express one or more anti-inflammatory genes (including, e.g., IDO1, IDO2, IL-10, IL-27, A20, TGFβ1, IL-10, and/or IFN-β) in DCs. For example, the effective amount of an IL-27/CD39 agonistic agent can be sufficient to upregulate the expression of CD39, phosphorylation of STAT3, and/or expression of one or more anti-inflammatory genes (including, e.g., IDO1, IDO2, IL-10, IL-27, A20, TGFβ1, IL-10, and/or IFN-β) in DCs by at least about 10% or more (including, e.g., at least about 20%, at least about 30%, at least about 40%, at least about 50%, at least about 60%, at least about 70%, at least about 80%, at least about 90%, at least about 95%, at least about 97% or more, as compared to DCs without the IL-27/CD39 agonistic agent. In some embodiments, the effective amount of an IL-27/CD39 agonistic agent can be sufficient to upregulate the expression of CD39, phosphorylation of STAT3, and/or expression of one or more anti-inflammatory genes (including, e.g., IDO1, IDO2, IL-10, IL-27, A20, TGFβ1, IL-10, and/or IFN-β) in DCs by at least about 1.1-fold or more (including, e.g., at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold or more, as compared to DCs without the IL-27/CD39 agonistic agent. Methods for detecting and/or measuring these biological molecules or cytokines are known in the art. For example, CD39 or anti-inflammatory gene and/or protein expressions in DCs can be analyzed by quantitative PCR, immunoassay, and/or FACS; while phosphorylated STAT3 can be determined by FACS, immunoassay, and/or western blot.

In some embodiments, the effective amount of the IL-27/CD39 agonistic agent can range from about 1 ng/mL to about 100 ng/mL. In some embodiments, the effective amount of the IL-27/CD39 agonistic agent can range from about 5 ng/mL to about 50 ng/mL, from about 10 ng/mL to about 40 ng/mL. In some embodiments, the effective amount of the IL-27/CD39 agonistic agent can be about 10 ng/mL to about 30 ng/mL, or about 15 ng/mL to about 25 ng/mL.

In some embodiments, the effective amount of the IL-27/CD39 agonistic agent can be at least about 1 ng/mL, at least about 5 ng/mL, at least about 10 ng/mL, at least about 15 ng/mL, at least about 20 ng/mL, at least about 25 ng/mL, at least about 30 ng/mL, at least about 40 ng/mL, at least about 50 ng/mL, at least about 60 ng/mL, at least about 70 ng/mL, at least about 80 ng/mL, at least about 90 ng/mL, or at least about 100 ng/mL.

In some embodiments, the effective amount of an IL-27 agonist can range from about 1 ng/mL to about 100 ng/mL. In some embodiments, the effective amount of the IL-27 agonist can range from about 5 ng/mL to about 50 ng/mL, from about 10 ng/mL to about 40 ng/mL. In some embodiments, the effective amount of the IL-27 agonist can be about 10 ng/mL to about 30 ng/mL, or about 15 ng/mL to about 25 ng/mL. In some embodiments, the effective amount of an IL-27 agonist can be at least about 1 ng/mL, at least about 5 ng/mL, at least about 10 ng/mL, at least about 15 ng/mL, at least about 20 ng/mL, at least about 25 ng/mL, at least about 30 ng/mL, at least about 40 ng/mL, at least about 50 ng/mL, at least about 60 ng/mL, at least about 70 ng/mL, at least about 80 ng/mL, at least about 90 ng/mL, or at least about 100 ng/mL.

In some embodiments, the method can further comprise contacting the dendritic cell with an autoimmune antigen. The contact of dendritic cells with at least one or more autoimmune antigens can occur prior to, concurrently with, or after the contact of dendritic cells with a composition comprising an IL-27/CD39 agonistic agent.

The term "antigen" as used herein means a substance, molecule, or compound that stimulates an immune response. Although usually a protein or polysaccharide, antigens may be any type of molecule or microorganism (e.g., cells and/or virus), which can include small molecules (haptens) that are optionally coupled to a carrier-protein.

As used herein, an "immune response" being modulated refers to a response by a cell of the immune system, such as a B cell, T cell (CD4 or CD8), regulatory T cell, antigen-presenting cell, dendritic cell, monocyte, macrophage, NKT cell, NK cell, basophil, eosinophil, or neutrophil, to a stimulus. In some embodiments, the response is specific for a particular antigen (an "antigen-specific response"), and refers to a response by a CD4 T cell, CD8 T cell, or B cell via their antigen-specific receptor. In some embodiments, an immune response is a T cell response, such as a CD4+ response or a CD8+ response. Such responses by these cells can include, for example, cytotoxicity, proliferation, cytokine or chemokine production, trafficking, or phagocytosis, and can be dependent on the nature of the immune cell undergoing the response.

As used herein, the term "autoimmune antigen" refers to any self protein or self component that serves either as a target or cause of an autoimmune disease. Examples of autoimmune antigens include, but are not limited to, myelin basic protein (MBP); proteolipid protein (PLP); myelin oligodendrocyte glycoprotein (MOG), myelin-associated oligodendrocytic basic protein cardiac myosin; outer surface protein (OSP); myelin associated glycoprotein (MAG); neurofilaments; interferon omega; transglutaminase; aromatic acid carboxylase; 17-hydroxylase; 21-hydroxylase, cardiolipin; pyruvate dehydrogenase; β2 glycoprotein I; phosphatidylserine; apoH; Annexin A5; LKM-1; soluble liver antigen; carbonic anhydrase; gpIIb-IIIa or 1b-IX; type XVII collagen; tissue transglutaminase; gliadin; GD1a; GQ1b; BP-1; BP-2; epidermal transglutaminase; histidine-tRNA; signal recognition peptide; Mi-2; Jo1; Glutamic acid decarboxylase, HSP60; HSP70; HSP90; IGRP; insulin; carboxypeptidase H; insulinoma antigen-2; IA-2beta; ICA69; ZnT8; chromogranin A; IAPP; scl70; topoisomerase; histones; Basement Membrane Collagen Type IV; enolase; thyroid peroxidase; thyroglobulin; complement component 3; voltage-gated calcium channels; Q-type calcium channel, synaptogagmin, muscarinic acetylcholine receptor M1; SMA; LKM-1; LKM-2; LKM-3; soluble liver antigen; SLA; LP; major peripheral myelin protein P0; myeloperoxidase; GQ1b; U1-RNP; Kir4.1; nicotinic acetylcholine receptor; MuSK protein; hypocretin; orexin; keratin; AQP4; Yo; Hu; glutamate receptor; Desmoglein 3; p62; sp100; Ro; LA; glycoproteins IIb-IIIa or Ib-IX; ADAMTS13; cardiolipin; β2 glycoprotein I; HPA-1a; HPA-5b; IFN-gamma, IL-1, TNF-alpha; GMCSF, portions thereof, and combinations thereof. Additional examples of autoimmune antigens include, but are not limited to, peripheral myelin proteins P0 and P2 (Guillain-Barre syndrome); acetylcholine receptor (myasthenia gravis); cardiac myosin (rheumatic fever/myocarditis); proteins of the beta cells in the Isles of Langerhans—GAD (glutamic acid decarboxylase), insulin (Type I autoimmune diabetes mellitus), the thyroid-stimulating hormone receptor (Grave's disease), platelets (thrombocytopenic purpura), neuromuscular junction (myasthenia gravis), red blood cells (autoimmune hemolytic anemia and intracellular antigens (spliceosomes, ribosomes, nucleic acid, etc in systemic lupus erythematosus), portions thereof, and combinations thereof.

In some embodiments, the autoimmune antigen can encompass a neuroantigen. As used herein, the term "neuroantigen" (NAg) refers to a type of autoimmune antigen that is a nervous system protein (central or peripheral) including an auto-reactive epitope. The neuroantigen can be a myelin basic protein (MBP), a proteolipid protein (PLP), myelin oligodendrocyte glycoprotein (MOG), myelin-associated oligodendrocytic basic protein (MOG), or other nervous system-derived proteins or a portion thereof and further including those derived from any species, including, e.g., human, rat and mouse.

The dendritic cell can be contacted with an amount of an autoimmune antigen sufficient to establish tolerance to a specific antigen. The term "tolerance" as used herein refers to a decreased level of an immune response, a delay in the onset or progression of an immune response and/or a reduced risk of the onset or progression of an immune response. "Specific" immunological tolerance occurs when immunological tolerance is preferentially invoked against certain antigens in comparison with others. "Active" immunological tolerance refers to a state in which the tolerance effect(s) are the result of an ongoing biological process: for example, down-regulation of specific effector cells by suppressor cells. "Sustained tolerance" is tolerance that measurably persists for an extended period of time.

In some embodiments, the autoimmune antigen to be contacted with a dendritic cell can be in a concentration of about 0.01 µg/mL to about 100 µg/mL, about 0.1 µg/mL to about 100 µg/mL, about 1 µg/mL to about 100 µg/mL, about 5 µg/mL to about 90 µg/mL, about 10 µg/mL to about 80 µg/mL, about 20 µg/mL to about 70 µg/mL, about 30 µg/mL to about 60 µg/mL. In some embodiments, the autoimmune antigen can have a concentration of about 0.1 µg/mL to about 10 µg/mL.

The methods of generating an immunosuppressive dendritic cell as described herein can be performed in a subject, ex vivo or in vitro. Accordingly, in some embodiments, a dendritic cell can be contacted ex vivo or in vitro with a composition comprising an IL-27/CD39 agonistic agent. In alternative embodiments, a dendritic cell can be contacted in vivo with a composition comprising an IL-27/CD39 agonistic agent.

As used herein, the term "contacting" refers to any suitable means for delivering, or exposing, an agent (e.g., an IL-27/CD39 agonistic agent and/or autoimmune antigen) to cells, e.g., dendritic cells. Exemplary delivery methods include, but are not limited to, direct delivery to cell culture medium, delivery to a cell culture, e.g., via perfusion, administration to a subject (e.g., by injection, and/or implantation), or other delivery method well known to one skilled in the art. In one embodiment, an IL-27/CD39 agonistic agent and the optional autoimmune antigen can be added to the cell culture medium in which the dendritic cells are cultured. In another embodiment, an IL-27/CD39 agonistic agent and optional autoimmune antigen can be coated on a solid support on which the dendritic cells are cultured. In still another embodiment, an IL-27/CD39 agonistic agent and optional autoimmune antigen can be injected into a biocompatible gel or matrix (e.g., peptide gel, hydrogel) in which the dendritic cells are encapsulated. In one embodiment, dendritic cells are contacted with an IL-27/CD39 agonistic agent and optional autoimmune antigen added to the cell culture medium. In another embodiment, an IL-27/CD39 agonistic agent and optional autoimmune antigen can be introduced or targeted to dendritic cells in a subject. The term "conditioned" or "treated" as used herein, with respect to exposing cells to an agent, e.g., treatment of dendritic cells with an IL-27/CD39 agonistic agent and optional autoimmune antigen, is used herein interchangeably with the term "contacting".

Dendritic cells can be contacted, treated or conditioned with a composition comprising an IL-27/CD39 agonistic agent and optional autoimmune antigen for any period of time, e.g., minutes, hours, days, or weeks. In some embodiments, the dendritic cells can be contacted with a composition comprising an IL-27/CD39 agonistic agent and optional autoimmune antigen for at least about 5 minutes, at least about 10 minutes, at least about 15 minutes, at least about 30 minutes, at least about 1 hour, at least about 2 hours, at least about 3 hours, at least about 4 hours, at least about 5 hours, at least about 6 hours, at least about 9 hours, at least about 12 hours, at least about 18 hours, at least about 24 hours or longer. In some embodiments, the dendritic cells can be contacted with a composition comprising an IL-27/CD39 agonistic agent and optional autoimmune antigen for at least about 1 day, at least about 2 days, at least about 3 days, at least about 4 days, at least about 5 days, at least about 6 days, at least about 7 days or longer. In some embodiments, the dendritic cells can be in contact with a composition comprising an IL-27/CD39 agonistic agent and optional autoimmune antigen until they are ready for administration to a subject in need thereof, e.g., diagnosed with an autoimmune disease.

The dendritic cell can be obtained or derived from any source. For example, the dendritic cell can be derived from a spleen, lymph node, blood, monocyte, and/or hematopoietic progenitor cell. In some embodiments, the dendritic cells comprise conventional (myeloid) DCs. In some embodiments, the dendritic cells comprise plasmacytoid DCs. Methods for isolation of dendritic cells are known in the art. See, e.g., Current Protocols in Immunology (1998) supplement 25: 3.7.1-3.7.15; Inaba et al. Curr Protoc Immunol (2001) Chapter 3: Unit 3.7, and the Examples described herein. Kits for isolation of dendritic cells are commercially available (e.g., from STEMCELL™ Technologies, and/or Life Technologies) and can be used to isolated dendritic cells.

Immunosuppressive Dendritic Cells:

In another aspect, immunosuppressive dendritic cell produced by the methods described herein involving an IL-27/CD39 agonistic agent are also provided herein. The immunosuppressive dendritic cells generated by various embodiments of the methods described herein are distinct and can be identified from non-treated dendritic cells using methods known in the art, including, but not limited to, FACS, western blot, qPCR, and/or immunoassay. In some embodiments, the immunosuppressive dendritic cells generated by the methods described herein can be identified and isolated from non-treated dendritic cells by FACS sorting based on expression of IL-27 and/or CD39, and/or phosphorylation of STAT3, and/or expression of anti-inflammatory genes, including, e.g., IDO1, IDO2, IL-10, IL-27, A20 and any other anti-inflammatory genes discussed in the Examples herein.

In some embodiments, the immunosuppressive dendritic cells described herein can comprise an increased expression of IL-27 by at least about 10% or more (including, e.g., at least about 20%, at least about 30%, at least about 40%, at least about 50%, at least about 60%, at least about 70%, at least about 80%, at least about 90%, at least about 95%, at least about 97%, or more, as compared to dendritic cells not contacted with an IL-27/CD39 agonistic agent (including, e.g., an IL-27 agonist). In some embodiments, the immunosuppressive dendritic cells described herein can comprise an increased expression of IL-27 by at least about 1.1-fold or more (including, e.g., at least about 1.5-fold, at least about 2-fold, at least about 3-fold, at least about 4-fold, at least about 5-fold, or more, as compared to dendritic cells not contacted with an IL-27/CD39 agonistic agent (including, e.g., an IL-27 agonist).

In some embodiments, the immunosuppressive dendritic cells described herein can comprise an increased expression of CD39 by at least about 10% or more (including, e.g., at least about 20%, at least about 30%, at least about 40%, at least about 50%, at least about 60%, at least about 70%, at least about 80%, at least about 90%, at least about 95%, at least about 97%, or more, as compared to dendritic cells not contacted with an IL-27/CD39 agonistic agent (including, e.g., an IL-27 agonist). In some embodiments, the immunosuppressive dendritic cells described herein can comprise an increased expression of CD39 by at least about 1.1-fold or more (including, e.g., at least about 1.5-fold, at least about 2-fold, at least about 3-fold, at least about 4-fold, at least about 5-fold, or more, as compared to dendritic cells not contacted with a composition comprising an IL-27/CD39 agonistic agent (including, e.g., an IL-27 agonist).

In some embodiments, the immunosuppressive dendritic cells described herein can comprise an increased phosphorylation of STAT3 by at least about 10% or more (including, e.g., at least about 20%, at least about 30%, at least about 40%, at least about 50%, at least about 60%, at least about 70%, at least about 80%, at least about 90%, at least about 95%, at least about 97%, or more, as compared to dendritic cells not contacted with an IL-27/CD39 agonistic agent (including, e.g., an IL-27 agonist). In some embodiments, the immunosuppressive dendritic cells described herein can comprise an increased phosphorylation of STAT3 by at least about 1.1-fold or more (including, e.g., at least about 1.5-fold, at least about 2-fold, at least about 3-fold, at least about 4-fold, at least about 5-fold, or more, as compared to dendritic cells not contacted with a composition comprising an IL-27/CD39 agonistic agent (including, e.g., an IL-27 agonist).

In some embodiments, the immunosuppressive dendritic cells can comprise a reduced production of an effector polarizing cytokine by at least about 10% or more (including, e.g., at least about 20%, at least about 30%, at least about 40%, at least about 50%, at least about 60%, at least about 70%, at least about 80%, at least about 90%, at least about 95%, at least about 97%, or up to 100%), as compared to dendritic cells not contacted with an IL-27/CD39 agonistic agent (including, e.g., an IL-27 agonist). Exemplary effector polarizing cytokines include, but are not limited to IL-12 and/or IL-6.

In some embodiments, the immunosuppressive dendritic cells can comprise an increased production of an anti-inflammatory cytokine and/or expression of an anti-inflammatory gene by at least about 10% or more (including, e.g., at least about 20%, at least about 30%, at least about 40%, at least about 50%, at least about 60%, at least about 70%, at least about 80%, at least about 90%, at least about 95%, at least about 97%, or more), as compared to dendritic cells not contacted with an IL-27/CD39 agonistic agent (including, e.g., an IL-27 agonist). Exemplary anti-inflammatory cytokine include, but are not limited to TGFβ1, IL-10, IFN-β, or any combinations thereof. Exemplary anti-inflammatory genes include, but are not limited to, IDO1, IDO2, IL-10, IL-27, A20 and any other anti-inflammatory genes discussed in the Examples herein.

In some embodiments, the immunosuppressive dendritic cells can be tolerogenic. By the term "tolerogenic" as used herein, it is meant that a response of immunological tolerance is induced by an antigen or antigenic substance or an activity that results in the induction of immunological tolerance toward an antigen or antigenic substance.

It is also contemplated that immunoactive dendritic cells can be produced by suppressing the IL-27/CD39 axis signaling. For example, dendritic cells can be contacted with an agent that suppresses one or more components of the IL-27/CD39 axis signaling. In some embodiments, such an agent can be an IL-27 antagonist. In some embodiments, such an agent can be a CD39 antagonist.

In some embodiments, dendritic cells can be obtained from a subject and made to become immunosuppressive dendritic cells using the methods described herein. The resultant, autologous immunosuppressive cells can then be administered to the subject for use in a therapeutic treatment, e.g., of an autoimmune disease.

Methods of Treating an Immune-Related Disease or Disorder, e.g., but not Limited to Autoimmune Diseases or Disorders As noted earlier, the inventors have discovered, among other things that, IL-27 acts on DCs to expand Tregs, limit Teffs and suppress autoimmune diseases, e.g., but not limited to type 1 diabetes, multiple sclerosis (MS) and encephalomyelitis in animal models. The anti-inflammatory effects of IL-27 on DCs are mediated at least in part by the up-regulation of the ectonucleotidase CD39 (encoded by ENTPD1) and the consequent decrease in the levels of pro-inflammatory extracellular ATP (eATP). In some immune-related diseases or disorders, e.g., but not limited to autoimmune diseases, it can be desirable to suppress pro-inflammatory responses, e.g., via Th1 and/or Th17 responses, or promote anti-inflammatory responses, e.g., via expression and/or production of anti-flammatory cytokines for a therapeutic effect. Accordingly, these immune-related diseases or disorders can be treated by inducing the IL-27/CD39 axis signaling in DCs to generate immunosuppressive DCs.

In some aspects, provided herein are methods of treating an autoimmune disease or disorder. "Autoimmune disease or disorder" refers to a class of diseases or disorders in which a subject's own antibodies react with host tissue or in which immune effector T cells are autoreactive to endogenous self-peptides and cause destruction of tissue. Thus an immune response is mounted against a subject's own antigens, referred to as self-antigens. A "self-antigen" as used herein refers to an antigen of a normal host tissue. Normal host tissue does not include cancer cells.

Accordingly, in some embodiments, the autoimmune diseases to be treated or prevented using the methods described herein, include, but are not limited to: rheumatoid arthritis, Crohn's disease, multiple sclerosis, systemic lupus erythematosus (SLE), autoimmune encephalomyelitis, myasthenia gravis (MG), Hashimoto's thyroiditis, Goodpasture's syndrome, pemphigus (e.g., pemphigus vulgaris), Grave's disease, autoimmune hemolytic anemia, autoimmune thrombocytopenic purpura, scleroderma with anti-collagen antibodies, mixed connective tissue disease, polymyositis, pernicious anemia, idiopathic Addison's disease, autoimmune-associated infertility, glomerulonephritis (e.g., crescentic glomerulonephritis, proliferative glomerulonephritis), bullous pemphigoid, Sjogren's syndrome, insulin resistance, and autoimmune diabetes mellitus (type 1 diabetes mellitus; insulin-dependent diabetes mellitus). Autoimmune disease has been recognized also to encompass atherosclerosis and Alzheimer's disease. In one embodiment of the aspects described herein, the autoimmune disease is selected from the group consisting of multiple sclerosis, type-I diabetes, Hashinoto's thyroiditis, Crohn's disease, rheumatoid arthritis, systemic lupus erythematosus, gastritis, autoimmune hepatitis, hemolytic anemia, autoimmune hemophilia, autoimmune lymphoproliferative syndrome (ALPS), autoimmune uveoretinitis, glomerulonephritis, Guillain-Barre syndrome, psoriasis and myasthenia gravis.

The method of treatment comprises administering to a patient in need thereof a dendritic cell (DC)-targeting composition comprising (i) an agent that stimulates or activates IL-27/ectonucleotidase CD39 axis signaling (or an IL-27/CD39 agonistic agent), and (ii) a DC-binding agent.

In some embodiments, the methods can be adapted to treat type 1 diabetes.

In some embodiments, the methods can be adapted to treat multiple sclerosis.

In some embodiments, the methods can be adapted to treat encephalomyelitis.

DC-Targeting Compositions:

A DC-targeting composition comprises at least one or more (e.g., at least two, at least three or more) IL-27/CD39 agonistic agents. In some embodiments, the IL-27/CD39 agonistic agent(s) can be an IL-27 agonist. For example, an IL-27 agonist can comprise a recombinant IL-27 protein or peptide. In some embodiments, the IL-27/CD39 agonistic agent(s) can be a CD39 agonist. In some embodiments, the IL-27/CD39 agonistic agent(s) can be an ATP-degrading enzyme, including, e.g., apyrase.

An IL-27/CD39 agonistic agent can be administered to in any amount sufficient to generate an immunosuppressive dendritic cell. For example, the effective amount of an IL-27/CD39 agonistic agent can be sufficient to upregulate the expression of CD39, phosphorylation of STAT3, and/or expression of one or more anti-inflammatory genes (including, e.g., IDO1, IDO2, IL-10, IL-27, A20, TGFβ1, IL-10, and/or IFN-β) in DCs, as compared to DCs not contacted with the IL-27/CD39 agonistic agent.

In some embodiments, the effective amount of an IL-27/CD39 agonistic agent present in a DC-targeting composition can be sufficient to upregulate expression of IL-27 in DCs by at least about 10% or more (including, e.g., at least about 20%, at least about 30%, at least about 40%, at least about 50%, at least about 60%, at least about 70%, at least about 80%, at least about 90%, at least about 95%, at least about 97%, or more, as compared to dendritic cells not contacted with an IL-27/CD39 agonistic agent (including, e.g., an IL-27 agonist). In some embodiments, the effective amount of an IL-27/CD39 agonistic agent can be sufficient to upregulate expression of IL-27 in DCs by at least about 1.1-fold or more (including, e.g., at least about 1.5-fold, at least about 2-fold, at least about 3-fold, at least about 4-fold, at least about 5-fold, or more, as compared to dendritic cells not contacted with an IL-27/CD39 agonistic agent (including, e.g., an IL-27 agonist).

In some embodiments, the effective amount of an IL-27/CD39 agonistic agent can be sufficient to upregulate expression of CD39 in DCs by at least about 10% or more (including, e.g., at least about 20%, at least about 30%, at least about 40%, at least about 50%, at least about 60%, at least about 70%, at least about 80%, at least about 90%, at least about 95%, at least about 97%, or more, as compared to dendritic cells not contacted with an IL-27/CD39 agonistic agent (including, e.g., an IL-27 agonist). In some embodiments, the effective amount of an IL-27/CD39 agonistic agent can be sufficient to upregulate expression of CD39 in DCs by at least about 1.1-fold or more (including, e.g., at least about 1.5-fold, at least about 2-fold, at least about 3-fold, at least about 4-fold, at least about 5-fold, or more, as compared to dendritic cells not contacted with a composition comprising an IL-27/CD39 agonistic agent (including, e.g., an IL-27 agonist).

In some embodiments, the effective amount of an IL-27/CD39 agonistic agent can be sufficient to upregulate phosphorylation of STAT3 in DCs by at least about 10% or more (including, e.g., at least about 20%, at least about 30%, at least about 40%, at least about 50%, at least about 60%, at least about 70%, at least about 80%, at least about 90%, at least about 95%, at least about 97%, or more, as compared to dendritic cells not contacted with an IL-27/CD39 agonistic agent (including, e.g., an IL-27 agonist). In some embodiments, the effective amount of an IL-27/CD39 agonistic agent can be sufficient to upregulate phosphorylation of STAT3 in DCs by at least about 1.1-fold or more (including, e.g., at least about 1.5-fold, at least about 2-fold, at least about 3-fold, at least about 4-fold, at least about 5-fold, or more, as compared to dendritic cells not contacted with a composition comprising an IL-27/CD39 agonistic agent (including, e.g., an IL-27 agonist).

In some embodiments, the effective amount of an IL-27/CD39 agonistic agent can be sufficient to reduce DCs' production of an effector polarizing cytokine by at least about 10% or more (including, e.g., at least about 20%, at least about 30%, at least about 40%, at least about 50%, at least about 60%, at least about 70%, at least about 80%, at least about 90%, at least about 95%, at least about 97%, or up to 100%), as compared to dendritic cells not contacted with an IL-27/CD39 agonistic agent (including, e.g., an IL-27 agonist). Exemplary effector polarizing cytokines include, but are not limited to IL-12 and/or IL-6.

In some embodiments, the effective amount of an IL-27/CD39 agonistic agent can be sufficient to increase DCs' production of at least one or more anti-inflammatory cytokine and/or expression of one or more anti-inflammatory gene by at least about 10% or more (including, e.g., at least about 20%, at least about 30%, at least about 40%, at least about 50%, at least about 60%, at least about 70%, at least about 80%, at least about 90%, at least about 95%, at least about 97%, or more), as compared to dendritic cells not contacted with an IL-27/CD39 agonistic agent (including, e.g., an IL-27 agonist). Exemplary anti-inflammatory cytokine include, but are not limited to TGFβ1, IL-10, IFN-β, or any combinations thereof. Exemplary anti-inflammatory genes include, but are not limited to, IDO1, IDO2, IL-10, IL-27, A20 and any other anti-inflammatory genes discussed in the Examples herein.

In some embodiments, the effective amount of the IL-27/CD39 agonistic agent can range from about 1 ng/mL to about 100 ng/mL. In some embodiments, the effective amount of the IL-27/CD39 agonistic agent can range from about 5 ng/mL to about 50 ng/mL, from about 10 ng/mL to about 40 ng/mL. In some embodiments, the effective amount of the IL-27/CD39 agonistic agent can be about 10 ng/mL to about 30 ng/mL, or about 15 ng/mL to about 25 ng/mL.

In some embodiments, the effective amount of the IL-27/CD39 agonistic agent can be at least about 1 ng/mL, at least about 5 ng/mL, at least about 10 ng/mL, at least about 15 ng/mL, at least about 20 ng/mL, at least about 25 ng/mL, at least about 30 ng/mL, at least about 40 ng/mL, at least about 50 ng/mL, at least about 60 ng/mL, at least about 70 ng/mL, at least about 80 ng/mL, at least about 90 ng/mL, or at least about 100 ng/mL.

In some embodiments, the effective amount of an IL-27 agonist can range from about 1 ng/mL to about 100 ng/mL. In some embodiments, the effective amount of the IL-27 agonist can range from about 5 ng/mL to about 50 ng/mL, from about 10 ng/mL to about 40 ng/mL. In some embodiments, the effective amount of the IL-27 agonist can be about 10 ng/mL to about 30 ng/mL, or about 15 ng/mL to about 25 ng/mL. In some embodiments, the effective amount of an IL-27 agonist can be at least about 1 ng/mL, at least about 5 ng/mL, at least about 10 ng/mL, at least about 15 ng/mL, at least about 20 ng/mL, at least about 25 ng/mL, at least about 30 ng/mL, at least about 40 ng/mL, at least about 50 ng/mL, at least about 60 ng/mL, at least about 70 ng/mL, at least about 80 ng/mL, at least about 90 ng/mL, or at least about 100 ng/mL.

The effective dosage of an IL-27/CD39 agonistic agent will vary from composition to composition, patient to patient, and will depend up on the physical and/or medical condition of a patient, and/or the route of delivery. In some embodiments, the effective amount of the IL-27/CD39 agonistic agent can vary with body weight of a subject, e.g., ranging from about 1 ng/kg to about 200 mg/kg, or from about 0.01 mg/kg to about 150 mg/kg, or from about 0.1 mg/kg to about 100 mg/kg, or from about 1 mg/kg to about 50 mg/kg. The effective dosage can be administered to a subject in a single dose or divided doses.

DC-Binding Agents:

DC-targeting compositions comprising an IL-27/CD39 agonistic agent described herein are adapted to preferentially or specifically target DCs. Accordingly, the DC-targeting compositions administered to a subject comprise one or more DC-binding agents. As used herein, the term "DC-binding agent" refers to any material, substance, agent or moiety which can promote targeting of a composition comprising an IL-27/CD39 agonistic agent to dendritic cells in vivo and/or in vitro. The DC-binding agent can be synthetic, semi-synthetic, or naturally-occurring. Materials or substances which can serve as DC-binding agents include, for example, proteins, including antibodies, antibody fragments, hormones, hormone analogues, glycoproteins, peptides, polypeptides, amino acids, sugars, saccharides, including monosaccharides and polysaccharides, carbohydrates, vitamins, steroids, steroid analogs, hormones, cofactors, and genetic material, including nucleosides, nucleotides, nucleotide acid constructs, peptide nucleic acids (PNA), aptamers, and polynucleotides. Other DC-binding agents in the present invention include cell adhesion molecules (CAM), among which are, for example, cytokines, integrins, cadherins, immunoglobulins and selectin. The DC-targeting compositions can also encompass at least one or more precursor DC-binding agent. A precursor to a DC-binding agent refers to any material or substance which can be converted to a DC-binding agent. Such conversion can involve, for example, anchoring a precursor to a DC-binding agent. Exemplary targeting precursor moieties include maleimide groups, disulfide groups, such as ortho-pyridyl disulfide, vinylsulfone groups, and azide groups. The DC-binding agent(s) can be covalently (e.g., cross-linked) or non-covalently linked to the DC-targeting composition and/or IL-27/CD39 agonistic agent.

In some embodiments, a DC-binding agent is an agent or moiety that specifically or preferentially targets or binds to DCs such that a substantial amount of an IL-27/CD30 agonistic agent can be delivered to DCs. In some embodiments, the DC-binding agent specifically targets or binds DCs only. In some embodiments, the DC-binding agent preferentially targets or binds DC and does not target any T cells. As used herein, the term "preferentially" refers to a greater amount of an IL-27/CD39 agonistic agent present in a DC-targeting composition being delivered to dendritic cells than any other cells. In some embodiments, at least 50% or more (including, e.g., at least about 60%, at least about 70%, at least about 80%, at least about 90%, at least about 95%, at least about 97%, or more, and up to 100%) of an IL-27/CD39 agonistic agent present in a DC-targeting composition is delivered to dendritic cells.

Any DC-binding agents known in the art can be used in the DC-targeting compositions. Examples of DC-binding agents include, but are not limited to agents that bind to a DC surface protein or receptor. An exemplary DC-binding agent includes, but is not limited to an antibody against Clec9A and/or DEC205. Additional examples of DC-binding agents such as anti-DC receptor antibodies and DC-binding peptides that can be used in the DC-targeting compositions described herein include, but not limited to the ones described in Flamar et al. Retrovirology (2009) 6 (Suppl 3): p286; Sioud et al. FASEB J. (2013) 27: 3272-83; and Subramanya et al. J. Virol (2010) 84: 2490-2501.

The term "antibody" as used herein generally refers to a full length antibody or immunoglobulin, IgG, IgM, IgA, IgD or IgE molecules, or a protein portion thereof that comprises only a portion of an intact antibody, generally including an antigen binding site of the intact antibody and thus retaining the ability to bind a target, such as an epitope or antigen. Examples of portions of antibodies or epitope-binding proteins encompassed by the present definition include: (i) the Fab fragment, having VL, CL, VH and CH1 domains; (ii) the Fab' fragment, which is a Fab fragment having one or more cysteine residues at the C-terminus of the CH1 domain; (iii) the Fd fragment having VH and CH1 domains; (iv) the Fd' fragment having VH and CH1 domains and one or more cysteine residues at the C terminus of the CH1 domain; (v) the Fv fragment having the VL and VH domains of a single arm of an antibody; (vi) the dAb fragment (Ward et al., 341 Nature 544 (1989)) which consists of a VH domain or a VL domain that binds antigen; (vii) isolated CDR regions or isolated CDR regions presented in a functional framework; (viii) F(ab')2 fragments which are bivalent fragments including two Fab' fragments linked by a disulphide bridge at the hinge region; (ix) single chain antibody molecules (e.g., single chain Fv; scFv) (Bird et al., 242 Science 423 (1988); and Huston et al., 85 PNAS 5879 (1988)); (x) "diabodies" with two antigen binding sites, comprising a heavy chain variable domain (VH) connected to a light chain variable domain (VL) in the same polypeptide chain (see, e.g., EP 404,097; WO 93/11161; Hollinger et al., 90 PNAS 6444 (1993)); (xi) "linear antibodies" comprising a pair of tandem Fd segments (VH-CH1-VH-CH1) which, together with complementary light chain polypeptides, form a pair of antigen binding regions (Zapata et al., 8 Protein Eng. 1057 (1995); and U.S. Pat. No. 5,641,870).

"Antibodies" include antigen-binding portions of antibodies such as epitope- or antigen-binding peptides, paratopes, functional CDRs; recombinant antibodies; chimeric antibodies; tribodies; midibodies; or antigen-binding derivatives, analogs, variants, portions, or fragments thereof.

In some embodiments, a DC-binding agent can comprise a single chain antibody against a dendritic cell surface protein or receptor, including, but not limited to, Clec9A and/or DEC205.

DC-Targeting Fusion Proteins:

The DC-targeting composition acting as an immunomodulator can be present in any appropriate format to specifically or preferentially target or bind DCs. For example, a DC-targeting composition can be a fusion protein comprising a DC-binding agent described herein and at least one or more IL-27/CD39 agonistic agents described herein. As used herein, the term "fusion protein" refers to a fusion polypeptide comprising a target polypeptide (e.g., an IL-27/CD39 agonistic agent) and at least a second, heterologous fusion partner polypeptide. The fusion partner can, for example, increase the in vivo stability of the fusion polypeptide, modulate its biological activity or localization, or facilitate purification of the fusion polypeptide.

In some embodiments, the fusion partner can facilitate targeting of the compositions described herein comprising at least one or more (including, e.g., at least two or more) IL-27/CD39 agonistic agents to dendritic cells. In some embodiments, the fusion partner can comprise or be a DC-binding agent described herein.

Additional examples of heterologous fusion partner polypeptides that can be further included to generate such fusion polypeptides for use in the compositions and methods described herein include, but are not limited to, polyhistidine (His or 6His tag (SEQ ID NO: 1)), Glu-Glu tag, glutathione S transferase (GST), thioredoxin, polypeptide A, polypeptide G, an immunoglobulin heavy chain constant region (Fc), and maltose binding polypeptide (MBP), which are particularly useful for isolation of the fusion polypeptides by affinity chromatography. For the purpose of affinity purification, relevant matrices for affinity chromatography, such as glutathione-, amylase-, and nickel- or cobalt-conjugated resins are used. In some embodiments, the fusion polypeptides can have a protease cleavage site, such as for Factor Xa or Thrombin, which allows the relevant protease to partially digest the fusion polypeptides and thereby liberate the recombinant polypeptides therefrom. The liberated polypeptides can then be isolated from the fusion polypeptides by subsequent chromatographic separation.

DC-Targeting Nanoparticles:

In some embodiments, the DC-targeting composition comprising at least one or more (including, e.g., at least two, at least three or more) IL-27/CD39 agonistic agents can be formulated in the form of nanoparticle(s). The IL-27/CD39 agonistic agent, DC-binding agent, and/or optional autoimmune antigen can distribute on a surface of the nanoparticle(s) or be encapsulated in the nanoparticle(s). In some embodiments, the DC-binding agent can form on the surface of the nanoparticle(s) while one or more IL-27/CD39 agonistic agents and optional autoimmune antigen(s) can be encapsulated in the nanoparticle(s), which can be released therefrom to DCs.

In some embodiments, the nanoparticle(s) can comprise on its surface a biocompatible layer or material. As used herein, the term "biocompatible layer or material" refers to any material or layer that does not deteriorate appreciably and does not induce a significant adverse effect, e.g., toxic reaction, over time when placed adjacent to the biological tissue of a subject, or induce blood clotting or coagulation when it comes in contact with blood. Suitable biocompatible materials can include, but are not limited to, polymers comprising an amino group (e.g., carbohydrate-based amino-polymers, protein-based amino-polymers, or molecules comprising at least one amino group), silk fibroin, derivatives and copolymers of polyimides, polyvinyl alcohol, polyethyleneimine, polyvinylamine, polyacrylates, polyamides, polyesters, polycarbonates, polydimethylsiloxane, polyimide, polyethylene terephthalate, polymethylmethacrylate, polyurethane, polyvinylchloride, polystyrene, polysulfone, polycarbonate, polymethylpentene, polypropylene, a polyvinylidine fluoride, polysilicon, polytetrafluoroethylene, polysulfone, acrylonitrile butadiene styrene, polyacrylonitrile, polybutadiene, poly(butylene terephthalate), poly(ether sulfone), poly(ether ether ketones), poly(ethylene glycol), styrene-acrylonitrile resin, poly(trimethylene terephthalate), polyvinyl butyral, polyvinylidenedifluoride, poly(vinyl pyrrolidone), polyethylene glycol, and any combinations thereof. In some embodiments, the nanoparticles can comprise on its surface a layer of polyethylene glycol (PEG). In some embodiments, the biocompatible layer can be selected to prolong the circulation time of the nanoparticles in a subject. In some embodiments, the biocompatible layer can be selected to induce antigen-specific immunity in a subject. In some embodiments, the biocompatible layer can be selected to reduce or minimize the exposure of the nanoparticle material to surrounding tissue in a subject. In one embodiment, the nanoparticle(s) can further comprise on its surface a PEG layer.

Generally, nanoparticles administered to a subject can be made of any biocompatible material as described herein and/or inert metals, e.g., but not limited to gold. As used herein, the term "nanoparticle" refers to particle having a particle size of about 0.1 nm to about 1000 nm. Further, the nanoparticle can be of any shape or form, e.g., spherical, rod, elliptical, cylindrical, capsule, or disc. The term "nanoparticle" includes nanospheres, nanorods, nanoshells, and nanoprisms and these nanoparticles can be part of a nanonetwork. Without limitations, the nanoparticles used herein can be any nanoparticle available in the art or available to one of skill in the art. In some embodiments, the nanoparticle is of size from about 10 nm to about 750 nm, from about 20 nm to about 500 nm, from about 25 nm to about 250 nm, or from about 50 nm to about 150 nm. In some embodiments, the nanoparticle is of size from about 5 nm to about 75 nm, from about 10 nm to about 50 nm, from about 15 nm to about 25 nm. The nanoparticles can be, e.g., monodisperse or polydisperse and the variation in diameter of the particles of a given dispersion can vary. The nanoparticles can be hollow or solid. In one embodiment, the nanoparticles are gold nanoparticles.

In one embodiment, a DC-targeting composition described herein comprises pegylated gold nanoparticles, wherein at least one or more (including, e.g., at least two or more) IL-27/CD39 agonistic agents form on the surface of the gold nanoparticles. The pegylated nanoparticles described in Yeste et al. PNAS (2012) 109: 1270-5 can be modified to deliver a composition comprising at least one or more (including, e.g., at least two or more) IL-27/CD39 agonistic agents to dendritic cells.

In some embodiments, the DC-targeting composition described herein can further comprise at least one or more (including, e.g., at least two, at least three or more) autoimmune antigens as described herein. In some embodiments, the autoimmune antigen(s) can be linked to a DC-targeting fusion protein described herein. In some embodiments, the autoimmune antigen(s) can be coupled to a DC-targeting nanoparticle described herein. The amount of an autoimmune antigen present in the DC-targeting composition can be sufficient to establish immune tolerance to a specific antigen in a subject in need thereof. For example, the amount of an autoimmune antigen in the DC-targeting composition can range from about 0.01 µg/mL to about 100 µg/mL, about 0.1 µg/mL to about 100 µg/mL, about 1 µg/mL to about 100 µg/mL, about 5 µg/mL to about 90 µg/mL, about 10 µg/mL to about 80 µg/mL, about 20 µg/mL to about 70 µg/mL, about 30 µg/mL to about 60 µg/mL. In some embodiments, the autoimmune antigen can have a concentration of about 0.1 µg/mL to about 10 µg/mL.

In some embodiments, the amount of an autoimmune antigen in the DC-targeting composition can range from about 0.01 µg/kg to about 1000 µg/kg, or from about 0.1 µg/kg to about 500 µg/kg, or from about 0.5 µg/kg to about 250 µg/kg, or from about 1 µg/kg to about 100 µg/kg. In some embodiments, the amount of an autoimmune antigen in the DC-targeting composition can range from about 1 mg/kg to about 500 mg/kg, or from about 5 mg/kg to about 250 mg/kg, or from about 10 mg/kg to about 100 mg/kg, or from about 20 mg/kg to about 50 mg/kg.

In another aspect, dendritic cells can be pre-treated with one or more IL-27/CD39 agonistic agents as described herein (including, e.g., IL-27 agonists) to generate immunosuppressive dendritic cells, which can then be administered or implanted to a subject in need thereof, e.g., a subject diagnosed with an autoimmune disease or disorder. Accordingly, also provided herein is a method of treating an autoimmune disease or disorder comprising administering to or placing in a subject in need thereof a composition comprising a population of immunosuppressive dendritic cells that are generated by contacting dendritic cells with at least one or more IL-27/CD39 agonistic agents (including, e.g., IL-27 agonists).

In some embodiments, the population of immunosuppressive dendritic cells comprise autologous dendritic cells. Thus, in some embodiments, the method can further comprise obtaining dendritic cells from a sample of a subject. For example, the sample can be a tissue biopsy from a spleen or lymph node, or a blood sample. The autologous dendritic cells can then be pre-treated ex vivo with at least one or more IL-27/CD39 agonistic agents (including, e.g., IL-27 agonists), followed by implantation into the subject.

In some embodiments, the composition comprising immunosuppressive dendritic cells can further comprise an autoimmune antigen as described herein. The autoimmune antigen can be administered prior to, concurrently with, or after the administration or placement of the composition comprising immunosuppressive dendritic cells at a target tissue or organ site of a subject.

Vaccines:

In some embodiments, the DC-targeting compositions described herein and/or composition comprising immunosuppressive dendritic cells described herein can be considered as therapeutic vaccines for treatment of an autoimmune disease or disorder.

The term "vaccine" as used herein generally refers to an immunological composition given to an animal to elicit an immune response against an agent. As used herein, the term "vaccine" includes both therapeutic and prophylactic vaccines. The term "vaccine" is defined herein in its broad sense to mean a biological agent used to produce active immunity. Vaccines generally employ one of four categories of antigens: live microorganisms administered via an unnatural route, live attenuated microorganisms, killed microorganisms and fractions or even a single antigen or product of a microorganism. In all situations, the goal is to present antigens without giving the disease. In some embodiments, the antigens comprise autoimmune antigens described herein.

In some embodiments, the vaccine described herein can further comprise an adjuvant. As used herein, the term "adjuvant" refers to a substance distinct from target antigen that is capable of enhancing or potentiating immune effector cell activation. Some adjuvants are believed to enhance the immune response by slowly releasing the antigen, while other adjuvants are strongly immunogenic and are believed to function synergistically. Known vaccine adjuvants include, but are not limited to, oil and water emulsions (for example, complete Freund's adjuvant and incomplete Freund's adjuvant, and adjuvants disclosed in U.S. Pat. No. 7,371,395 to Merial Limited, which are herein incorporated by reference in their entirety), *Corynebacterium parvum*, *Bacillus* Calmette Guerin, aluminum hydroxide, glucan, dextran sulfate, iron oxide, sodium alginate, Bacto-Adjuvant, certain synthetic polymers such as poly amino acids and co-polymers of amino acids, saponin, "REGRESSIN" (Vetrepharm, Athens, Ga.), "AVRIDINE" (N, N-dioctadecyl-N',N'-bis(2-hydroxyethyl)-propanediamine), paraffin oil, muramyl dipeptide and the like.

Accordingly, in another aspect, methods of treating an autoimmune disease or disorder comprising vaccinating a subject with a vaccine comprising a DC-targeting composition described herein and/or a composition comprising a population of immunosuppressive cells. The term "vaccinating" or "vaccination" is well-understood in the art. For example, the term "vaccination" can be understood to be a process that increases a subject's immune reaction to antigen and therefore the ability to resist or overcome infection. In the case of the present invention, vaccination or immunization may decrease the recipient's immune response against self antigens thereby decreasing the likelihood of an autoimmune response.

It is contemplated that in other immune-related diseases or disorder, including, e.g., cancer, it can be desirable to induce proinflammatory responses, e.g., Th1/Th17 responses, at a target site (e.g., a tumor) for a therapeutic effect. Accordingly, these immune-related diseases or disorders, e.g., but not limited to cancer, where upregulation of immune response is desirable, can be treated by suppressing the IL-27/CD39 axis signaling. For example, in some embodiments, a subject who is diagnosed with cancer can be administered with a DC-targeting composition comprising a DC-binding agent and an agent that suppresses IL-27/CD39 axis signaling (also referred to as "IL-27/CD39 antagonistic agent").

It is also contemplated that other inflammatory diseases or disorders, including, e.g., allergy and asthma, where a dampening Th2 response is desirable could be treated by down-regulating or suppressing the IL-27/CD39 axis signaling.

Agents that Stimulates or Activates the IL-27/CD39 Axis Signaling ("IL-27/CD39 Agonistic Agents") (I) IL-27 and Agonists Thereof IL-27 is a cytokine structurally related to IL-12 and is composed of a p28 subunit and the product of Epstein-Barr virus-induced gene 3 (Ebi3) (8). IL-27 signals through a receptor composed of the common IL-6 receptor chain gp130 (which is used by several other members of the IL-6 and IL-12 families) and a unique IL-27 receptor α-chain (IL-27RA) that is homologous to the IL-12Rβ2 chain of the IL-12 receptor (8). Previous report shows that IL-27 can be produced by DCs in response to activation via Toll-like receptors through a mechanism that involves the autocrine effects of interferon-β (IFN-β) (9). However, it is not known that IL-27 can act on DCs to suppress a T cell response and autoimmunity.

On the basis of its structural homology to IL-12 and its ability to trigger IFN-γ production, IL-27 was initially believed to be a proinflammatory cytokine (11). However, it was subsequently reported that IL-27 suppresses TH1, TH2 and TH17 responses and limits CNS inflammation in several experimental models (8). In the EAE model, the administration of IL-27 inhibits disease development (12). Conversely, the lack of a functional IL-27 receptor results in exacerbated TH17 responses and the worsening of EAE (12, 13). It is previously reported that IL-27 acts directly on T cells to inhibit the development of pathogenic TH17 cells and to promote the differentiation of IL-10-producing type 1 Treg cells (Tr1 cells) (12-17). Thus, the arrest of EAE by IL-27 is generally believed to reflect its direct effects on T cells until the inventors discovered that IL-27 can act on dendritic cells to suppress the T cell response and autoimmunity by inducing expression of the immunoregulatory molecule CD39 as shown herein in the Examples.

As used herein, the term "IL-27" generally refers to an IL-27 polypeptide or an IL-27 polynucleotide that is similar or identical to the sequence of a wild-type IL-27.

In some embodiments, the term "IL-27" refers to an IL-27 polypeptide having an amino acid sequence that is at least 70% or more (including at least 75%, at least 80%, at least 85%, at least 90%, at least 95%, at least 97%, at least 99%, or 100%) identical to that of a wild-type IL-27, and is capable of acting on DCs and suppressing T cell response. In some embodiments, the IL-27 polypeptide can also increase expression and/or activity of CD39 to mediate the immunosuppression.

In some embodiments, the term "IL-27" refers to an IL-27 polynucleotide having a nucleotide sequence that is at least 70% or more (including at least 75%, at least 80%, at least 85%, at least 90%, at least 95%, at least 97%, at least 99%, or 100%) identical to that of a wild-type IL-27 or a portion thereof, and encodes an IL-27 polypeptide as described herein.

The wild-type IL-27 sequences of various species are available on the world wide web from the NCBI, including human, mouse, pig, rat, dog, and cattle. For example, the nucleotide sequence encoding human IL-27 is available at NCBI under Accession No. NM_145659 and its corresponding amino acid sequence is under Accession No. NP_663634.

Where the term "IL-27" refers to an IL-27 polypeptide, the term "IL-27 polypeptide" also encompasses a portion or fragment of such an IL-27 polypeptide that retains at least about 70% or more (including at least 75%, at least 80%, at least 85%, at least 90%, at least 95%, at least 97%, at least 99%, or 100%) of the activity of the wild-type IL-27 polypeptide to act on DCs to suppress T cell response. The term "IL-27 polypeptide" as used herein also encompasses conservative substitution variants of an IL-27 polypeptide that retain at least about 70% or more (including at least 75%, at least 80%, at least 85%, at least 90%, at least 95%, at least 97%, at least 99%, or 100%) of the activity of the wild-type IL-27 polypeptide to act on DCs to suppress T cell response. Accordingly, an IL-27 polypeptide refers to any immunosuppressive form of IL-27, including functional variants of IL-27. For example, in some embodiments, an IL-27 polypeptide can be a full-length IL-27. In some embodiments, an IL-27 polypeptide refers to a functional domain or domains of IL-27 that acts on DCs and induces immunosuppression and expression and/or activity of CD39.

The amino acid identity between two polypeptides can be determined, for example, by first aligning the two polypeptide sequences using an alignment algorithm, such as BLAST® or by other methods well-known in the art.

In a similar manner, the term "agonist" is used in the broadest sense and includes any molecule that mimics a biological activity of a native polypeptide disclosed herein. Suitable agonist molecules specifically include agonistic antibodies or antibody fragments, fragments or amino acid sequence variants of native polypeptides, peptides, antisense oligonucleotides, small organic molecules, recombinant proteins or peptides, etc. Methods for identifying agonists of a polypeptide can comprise contacting a polypeptide with a candidate agonist molecule and measuring a detectable change in one or more biological activities normally associated with the polypeptide.

As used herein, the term "IL-27 agonist" refers to an agent that enhances or stimulates the normal functioning of IL-27, by increasing transcription or translation of IL-27-encoding nucleic acid, and/or by inhibiting or blocking activity of a molecule that inhibits IL-27 expression or IL-27 activity, and/or by enhancing normal IL-27 activity (including, but not limited to, enhancing the stability of IL-27 or enhancing binding of IL-27 to one or more target receptor such as IL-27RA). For example, the IL-27 agonist can be selected from an antibody, an antigen-binding fragment, an aptamer, an interfering RNA, a small molecule, a peptide, an antisense molecule, and another binding polypeptide. In another example, the IL-27 agonist can be a polynucleotide selected from an aptamer, interfering RNA, or antisense molecule that interferes with the transcription and/or translation of an IL-27-inhibitory molecule. It will be understood by one of ordinary skill in the art that in some instances, an IL-27 agonist can agonize one IL-27 activity without affecting another IL-27 activity. For example, a desirable IL-27 agonist for use in certain of the methods herein is an IL-27 agonist that agonizes IL-27 activity to act on DCs to induce immunosuppression, e.g., without affecting or minimally affecting any of the other IL-27 interactions.

In some embodiments, an IL-27 agonist is an agent that directly or indirectly enhances or stimulates the IL-27-mediated signaling in DCs to induce immunosuppression. Accordingly, an IL-27 agonist can target the IL-27 receptor or its corresponding ligand, or any of IL-27's upstream molecules. Examples of IL-27 agonists include, without limitations, IL-27 recombinant peptides or proteins and/or IL-27 receptor agonists (e.g., IL-27RA agonists). The IL-27 agonists can be a protein, a peptide, peptidomimetic, an aptamer, a nucleic acid, an antibody, a small molecule, a vaccine, a fusion protein, a recombinant molecule, or any combinations thereof.

In some embodiments, an IL-27 agonist is a recombinant IL-27 protein (e.g., a recombinant human IL-27 protein). Recombinant IL-27 proteins are commercially available (e.g., from Biolegend (Cat. No. 589202); Affymetrix eBioscience (Cat. No. 34-8279-82); and R&D Systems (Cat. No. 2526-IL-010/CF)).

IL-27 agonists can be obtained from known sources or prepared using known techniques such as recombinant or synthetic technology. The nucleic acid and protein sequences of IL-27 and its receptors of different species (e.g., but not limited to, human, mouse, rat, dog, chimpanzee) are known in the art, e.g., accessible at world wide web from NCBI. Thus, one of skill in the art can generate IL-27 agonists based on these sequences using art-recognized molecular technologies such as cloning and expression technologies. For example, a human IL-27 agonist (e.g., an IL-27 recombinant protein) can be generated based on the nucleic acid sequence of human IL-27 accessible at NCBI under Accession No. NM_145659 and/or its corresponding amino acid sequence under Accession No. NP_663634, or fragments thereof.

(II) CD39 and Agonists Thereof

CD39 is a cell surface-located prototypic member of the ecto-nucleoside triphosphate diphosphohydrolase (E-NTPDase) family, and is also known as ENTPD1, ATPDase, or NTPDase-1. CD39 is an ectonucleotidase that catalyzes the degradation of extracellular ATP and ADP. Extracellular ATP triggers activation of the NLRP3 inflammasome, a process shown to control the differentiation of encephalitogenic Th1 and Th17 cells during EAE.

As used herein, the term "CD39" generally refers to a CD39 polypeptide or a CD39 polynucleotide that is similar or identical to the sequence of a wild-type CD39.

In some embodiments, the term "CD39" refers to a CD39 polypeptide having an amino acid sequence that is at least 70% or more (including at least 75%, at least 80%, at least 85%, at least 90%, at least 95%, at least 97%, at least 99%, or 100%) identical to that of a wild-type CD39, and is capable of catalyzing the degradation of extracellular ATP (eATP).

In some embodiments, the term "CD39" refers to a CD39 polynucleotide having a nucleotide sequence that is at least 70% or more (including at least 75%, at least 80%, at least 85%, at least 90%, at least 95%, at least 97%, at least 99%, or 100%) identical to that of a wild-type CD39 or a portion thereof, and encodes a CD39 polypeptide as described herein.

The wild-type CD39 sequences of various species are available on the world wide web from the NCBI, including human, mouse, pig, and rat. For example, the nucleotide sequence encoding human CD39 is available at NCBI under Accession No. NM_001098175, NM_001164178, NM_001164179, NM_001164181, NM_001164182, NM_001164183, or NM_001776, and its corresponding amino acid sequence is under Accession No. NP_001091645, NP_001157650, NP_001157651, NP_001157653, NP_001157654, NP_001157655, or NP_001767.

Where the term "CD39" refers to a CD39 polypeptide, the term "CD39 polypeptide" also encompasses a portion or fragment of such a CD39 polypeptide that retains at least about 70% or more (including at least 75%, at least 80%, at least 85%, at least 90%, at least 95%, at least 97%, at least 99%, or 100%) of the activity of the wild-type CD39 polypeptide to catalyze the degradation of eATP. The term "CD39 polypeptide" as used herein also encompasses conservative substitution variants of a CD39 polypeptide that retain at least about 70% or more (including at least 75%, at least 80%, at least 85%, at least 90%, at least 95%, at least 97%, at least 99%, or 100%) of the activity of the wild-type CD39 polypeptide to catalyze degradation of eATP. Accordingly, a CD39 polypeptide refers to any form of CD39 that can catalyze degradation of eATP, including functional variants of CD39. For example, in some embodiments, a CD39 polypeptide can be a full-length CD39. In some embodiments, a CD39 polypeptide refers to a functional domain or domains of CD39 that catalyze degradation of eATP.

As used herein, the term "CD39 agonist" refers to an agent that enhances or stimulates the normal functioning of CD39, by increasing transcription or translation of CD39-encoding nucleic acid, and/or by inhibiting or blocking activity of a molecule that inhibits CD39 expression or CD39 activity, and/or by enhancing normal CD39 activity (including, but not limited to, enhancing the stability of CD39 or enhancing IL-27 signaling that induces CD39 expression. For example, the CD39 agonist can be selected from an antibody, an antigen-binding fragment, an aptamer, an interfering RNA, a small molecule, a peptide, an antisense molecule, and another binding polypeptide. In another example, the CD39 agonist can be a polynucleotide selected from an aptamer, interfering RNA, or antisense molecule that interferes with the transcription and/or translation of a CD39-inhibitory molecule. It will be understood by one of ordinary skill in the art that in some instances, a CD39 agonist can agonize one CD39 activity without affecting another CD39 activity. For example, a desirable CD39 agonist for use in certain of the methods herein is a CD39 agonist that agonizes CD39 activity to catalyze degradation of eATP, e.g., without affecting or minimally affecting any of the other CD39 interactions.

In some embodiments, a CD39 agonist is an agent that directly or indirectly enhances or stimulates the CD39-mediated degradation of eATP, which in turn down-regulate activation of the NLRP3 inflammasome. Accordingly, a CD39 agonist can target the CD39 itself, CD39 ligands, or any of CD39's upstream molecules. Examples of CD39 agonists include, without limitations, CD39 recombinant peptides or proteins, and/or IL-27 agonists. The CD39 agonists can be a protein, a peptide, peptidomimetic, an aptamer, a nucleic acid, an antibody, a small molecule, a vaccine, a fusion protein, a recombinant molecule, or any combinations thereof.

In some embodiments, a CD39 agonist is a recombinant CD39 protein (e.g., a recombinant human CD39 protein). Recombinant CD39 proteins are commercially available (e.g., from R&D Systems (Cat. No. 4397-EN-010)).

CD39 agonists can be obtained from known sources or prepared using known techniques such as recombinant or synthetic technology. The nucleic acid and protein sequences of CD39 and its receptors of different species (e.g., but not limited to, human, mouse, and rat) are known in the art, e.g., accessible at world wide web from NCBI. Thus, one of skill in the art can generate CD39 agonists based on these sequences using art-recognized molecular technologies such as cloning and expression technologies. For example, a human CD39 agonist (e.g., a CD39 recombinant protein) can be generated based on the nucleic acid sequence of human CD39 accessible at NCBI under Accession No. NM_001098175, NM_001164178, NM_001164179, NM_001164181, NM_001164182, NM_001164183, or NM_001776, and its corresponding amino acid sequence under Accession No. NP_001091645, NP_001157650, NP_001157651, NP_001157653, NP_001157654, NP_001157655, or NP_001767, or fragments thereof.

(III) ATP-Degrading Agents (e.g., Apyrase and Agonists Thereof)

ATP-degrading agents are molecules or compounds that can degrade and/or catalyze the degradation/hydrolysis of eATP. In some embodiments, an ATP-degrading agent comprises apyrase. Apyrase, also known as ATP-diphosphatase, adenosine diphosphatase, ADPase, ATP diphosphohydrolase is a calcium-activated plasma membrane-bound enzyme that catalyzes the hydrolysis of ATP to yield AMP and inorganic phosphate. Two isoenzymes are found in commercial preparations from *S. tuberosum*.

As used herein, the term "apyrase" generally refers to an apyrase polypeptide or an apyrase polynucleotide that is similar or identical to the sequence of a wild-type apyrase.

In some embodiments, the term "apyrase" refers to an apyrase polypeptide having an amino acid sequence that is at least 70% or more (including at least 75%, at least 80%, at least 85%, at least 90%, at least 95%, at least 97%, at least 99%, or 100%) identical to that of a wild-type apyrase, and is capable of catalyzing the degradation/hydrolysis of extracellular ATP (eATP).

In some embodiments, the term "apyrase" refers to an apyrase polynucleotide having a nucleotide sequence that is at least 70% or more (including at least 75%, at least 80%, at least 85%, at least 90%, at least 95%, at least 97%, at least 99%, or 100%) identical to that of a wild-type apyrase polynucleotide or a portion thereof, and encodes an apyrase polypeptide as described herein.

The wild-type apyrase sequences of various species are available on the world wide web from the NCBI, including human, mouse, pig, rat, and potatoes. For example, the nucleotide sequence encoding human apyrase is available at NCBI under Accession No. NM_001159772, NM_001159773, or NM_138793, and its corresponding amino acid sequence is under Accession No. NP_001153244, NP_001153245, or NP_620148.

Where the term "apyrase" refers to an apyrase polypeptide, the term "apyrase polypeptide" also encompasses a portion or fragment of such an apyrase polypeptide that retains at least about 70% or more (including at least 75%, at least 80%, at least 85%, at least 90%, at least 95%, at least 97%, at least 99%, or 100%) of the activity of the wild-type apyrase polypeptide to catalyze the degradation/hydrolysis of eATP. The term "apyrase polypeptide" as used herein also encompasses conservative substitution variants of a apyrase polypeptide that retain at least about 70% or more (including at least 75%, at least 80%, at least 85%, at least 90%, at least 95%, at least 97%, at least 99%, or 100%) of the activity of the wild-type apyrase polypeptide to catalyze degradation/hydrolysis of eATP. Accordingly, an apyrase polypeptide refers to any form of apyrase that can catalyze degradation/hydrolysis of eATP, including functional variants of apyrase. For example, in some embodiments, an apyrase polypeptide can be a full-length apyrase. In some embodiments, an apyrase polypeptide refers to a functional domain or domains of apyrase that catalyze degradation/hydrolysis of eATP.

As used herein, the term "apyrase agonist" refers to an agent that enhances or stimulates the normal functioning of apyrase, by increasing transcription or translation of apyrase-encoding nucleic acid, and/or by inhibiting or blocking activity of a molecule that inhibits apyrase expression or apyrase activity, and/or by enhancing normal apyrase activity (including, but not limited to, enhancing the stability of apyrase. For example, the apyrase agonist can be selected from an antibody, an antigen-binding fragment, an aptamer, an interfering RNA, a small molecule, a peptide, an antisense molecule, and another binding polypeptide. In another example, the apyrase agonist can be a polynucleotide selected from an aptamer, interfering RNA, or antisense molecule that interferes with the transcription and/or translation of an apyrase-inhibitory molecule. It will be understood by one of ordinary skill in the art that in some instances, an apyrase agonist can agonize one apyrase activity without affecting another apyrase activity. For example, a desirable apyrase agonist for use in certain of the methods herein is an apyrase agonist that agonizes apyrase activity to catalyze degradation/hydrolysis of eATP, e.g., without affecting or minimally affecting any of the other apyrase interactions.

In some embodiments, an apyrase agonist is an agent that directly or indirectly enhances or stimulates the apyrase-mediated degradation/hydrolysis of eATP, which in turn down-regulate activation of the NLRP3 inflammasome. Accordingly, an apyrase agonist can target the apyrase itself, or any of apyrase's upstream molecules. Examples of apyrase agonists include, without limitations, recombinant apyrase, CD39 agonists, and/or IL-27 agonists. The apyrase agonists can be a protein, a peptide, peptidomimetic, an aptamer, a nucleic acid, an antibody, a small molecule, a vaccine, a fusion protein, a recombinant molecule, or any combinations thereof.

In some embodiments, an apyrase agonist is a recombinant apyrase protein (e.g., a recombinant human apyrase protein). Recombinant apyrase proteins are commercially available (e.g., from Sigma-Aldrich (Cat. No. A6535) or New England Biolabs (Cat. No. M0393). In some embodiments, apyrase from potatoes is used in the methods and/or compositions described herein.

Apyrase agonists can be obtained from known sources or prepared using known techniques such as recombinant or synthetic technology. The nucleic acid and protein sequences of apyrase and its receptors of different species (e.g., but not limited to, human, mouse, pig, rat, and potatoes) are known in the art, e.g., accessible at world wide web from NCBI. Thus, one of skill in the art can generate apyrase agonists based on these sequences using art-recognized molecular technologies such as cloning and expression technologies. For example, a human apyrase agonist (e.g., a recombinant apyrase) can be generated based on the nucleic acid sequence of human apyrase accessible at NCBI under Accession No. NM_001159772, NM_001159773, or NM_138793, and its corresponding amino acid sequence under Accession No. NP_001153244, NP_001153245, or NP_620148, or fragments thereof. In some embodiments, an apyrase agonist can be generated based on the nucleic acid sequence of potato apyrase accessible at NCBI under XM_006349845 or its corresponding amino acid sequence under Accession No. XP_006349907.

Pharmaceutical Compositions

Pharmaceutical compositions for treatment of an immune-related disease or disorder, including, e.g., autoimmune diseases or disorders are also provided herein. More specifically, the pharmaceutical composition comprises (i) a pharmaceutically-acceptable excipient; and (ii) a DC-targeting composition comprising at least one or more (including, e.g., at least two or more) IL-27/CD39 agonistic agents, and/or an immunosuppressive dendritic cell described herein.

In some embodiments, the pharmaceutical composition can further comprise an agent for treatment of an autoimmune disease or disorder. For example, the agent can comprise an agent that increases an anti-inflammatory T cell response and/or an agent that suppresses a proinflammatory T cell response.

The phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier" as used herein means a pharmaceutically acceptable material, composition or vehicle, such as a liquid or solid filler, diluent, excipient, solvent, media, encapsulating material, manufacturing aid (e.g., lubricant, talc magnesium, calcium or zinc stearate, or steric acid), or solvent encapsulating material, involved in maintaining the stability, solubility, or activity of, an IL-27/CD39 agonistic agent or an immunosuppressive dendritic cell described herein. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) excipients, such as cocoa butter and suppository waxes; (8) oils, such as peanut oil, cottonseed oil, safflower oil, sesame oil, olive oil, corn oil and soybean oil; (9) glycols, such as propylene glycol; (10) polyols, such as glycerin, sorbitol, mannitol and polyethylene glycol (PEG); (11) esters, such as ethyl oleate and ethyl laurate; (12) agar; (13) buffering agents, such as magnesium hydroxide and aluminum hydroxide; (14) alginic acid; (15) pyrogen-free water; (16) isotonic saline; (17) Ringer's solution; (19) pH buffered solutions; (20) polyesters, polycarbonates and/or polyanhydrides; (21) bulking agents, such as polypeptides and amino acids (22) serum components, such as serum albumin, HDL and LDL; (23) C2-C12 alcohols, such as ethanol; and (24) other non-toxic compatible substances employed in pharmaceutical formulations. Release agents, coating agents, preservatives, and antioxidants can also be present in the formulation. The terms such as "excipient", "carrier", "pharmaceutically acceptable carrier" or the like are used interchangeably herein.

The pharmaceutical compositions described herein can be specially formulated for administration of a DC-targeting composition or an immunosuppressive dendritic cell described herein to a subject in solid, liquid or gel form, including those adapted for the following: (1) parenteral administration, for example, by subcutaneous, intramuscular, intravenous or epidural injection as, for example, a sterile solution or suspension, or sustained-release formulation; (2) topical application, for example, as a cream, ointment, or a controlled-release patch or spray applied to the skin; (3) intravaginally or intrarectally, for example, as a pessary, cream or foam; (4) ocularly; (5) transdermally; (6) transmucosally; or (79) nasally. Additionally, a bispecific or multispecific polypeptide agent can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 3,270,960.

Further embodiments of the formulations and modes of administration of the pharmaceutical compositions described herein that can be used in the methods described herein are illustrated below.

Parenteral Dosage Forms.

Parenteral dosage forms of a DC-targeting composition comprising at least one or more (including, e.g., at least two or more) IL-27/CD39 agonistic agents, and/or an immunosuppressive dendritic cell described herein can also be administered to a subject by various routes, including, but not limited to, subcutaneous, intravenous (including bolus injection), intramuscular, and intraarterial. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, controlled-release parenteral dosage forms, and emulsions.

Suitable vehicles that can be used to provide parenteral dosage forms of the disclosure are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate.

Controlled and Delayed Release Dosage Forms.

In some embodiments of the methods described herein, a DC-targeting composition comprising at least one or more (including, e.g., at least two or more) IL-27/CD39 agonistic agents, and/or an immunosuppressive dendritic cell described herein can be administered to a subject by controlled- or delayed-release means. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. (Kim, Cherng-ju, Controlled Release Dosage Form Design, 2 (Technomic Publishing, Lancaster, Pa.: 2000)). Controlled-release formulations can be used to control a compound of formula (I)'s onset of action, duration of action, plasma levels within the therapeutic window, and peak blood levels. In particular, controlled- or extended-release dosage forms or formulations can be used to ensure that the maximum effectiveness of a compound of formula (I) is achieved while minimizing potential adverse effects and safety concerns, which can occur both from under-dosing a drug (i.e., going below the minimum therapeutic levels) as well as exceeding the toxicity level for the drug.

A variety of known controlled- or extended-release dosage forms, formulations, and devices can be adapted for use with a DC-targeting composition comprising at least one or more (including, e.g., at least two or more) IL-27/CD39 agonistic agents, and/or an immunosuppressive dendritic cell described herein. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1, each of which is incorporated herein by reference in their entireties. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), multilayer coatings, microparticles, liposomes, or microspheres or a combination thereof to provide the desired release profile in varying proportions. Additionally, ion exchange materials can be used to prepare immobilized, adsorbed salt forms of the disclosed compounds and thus effect controlled delivery of the drug. Examples of specific anion exchangers include, but are not limited to, Duolite® A568 and Duolite® AP143 (Rohm&Haas, Spring House, Pa. USA).

In some embodiments, a DC-targeting composition comprising at least one or more (including, e.g., at least two or more) IL-27/CD39 agonistic agents, and/or an immunosuppressive dendritic cell described herein for use in the methods described herein is administered to a subject by sustained release or in pulses. Pulse therapy is not a form of discontinuous administration of the same amount of a composition over time, but comprises administration of the same dose of the composition at a reduced frequency or administration of reduced doses. Sustained release or pulse administrations are particularly preferred when the disorder occurs continuously in the subject, for example where the subject has continuous or chronic symptoms of a viral infection. Each pulse dose can be reduced and the total amount of a DC-targeting composition comprising at least one or more (including, e.g., at least two or more) IL-27/CD39 agonistic agents, and/or an immunosuppressive dendritic cell described herein administered over the course of treatment to the patient is minimized.

The interval between pulses, when necessary, can be determined by one of ordinary skill in the art. Often, the interval between pulses can be calculated by administering another dose of the composition when the composition or the active component of the composition is no longer detectable in the subject prior to delivery of the next pulse. Intervals can also be calculated from the in vivo half-life of the composition. Intervals can be calculated as greater than the in vivo half-life, or 2, 3, 4, 5 and even 10 times greater the composition half-life. Various methods and apparatus for pulsing compositions by infusion or other forms of delivery to the patient are disclosed in U.S. Pat. Nos. 4,747,825; 4,723,958; 4,948,592; 4,965,251 and 5,403,590.

Embodiments of various aspects described herein can be defined in any of the following numbered paragraphs:

1. A method of generating an immunosuppressive dendritic cell comprising contacting a dendritic cell with a composition comprising an effective amount of an IL-27 agonist.
2. The method of paragraph 1, wherein the effective amount of the IL-27 agonist ranges from about 1 ng/mL to about 100 ng/mL.
3. The method of paragraph 1 or 2, further comprising contacting the dendritic cell with an autoimmune antigen.
4. The method of paragraph 3, wherein the autoimmune antigen has a concentration of about 1 µg/mL to about 100 µg/mL.
5. The method of paragraph 3 or 4, wherein the autoimmune antigen is selected from the group consisting of myelin basic protein (MBP); proteolipid protein (PLP); myelin oligodendrocyte glycoprotein (MOG), myelin-associated oligodendrocytic basic protein cardiac myosin; outer surface protein (OSP); myelin associated glycoprotein (MAG); neurofilaments; interferon omega; transglutaminase; aromatic acid carboxylase; 17-hydroxylase; 21-hydroxylase, cardiolipin; pyruvate dehydrogenase; β2 glycoprotein I; phosphatidylserine; apoH; Annexin A5; LKM-1; soluble liver antigen; carbonic anhydrase; gpIIb-IIIa or 1b-IX; type XVII collagen; tissue transglutaminase; gliadin; GD1a; GQ1b; BP-1; BP-2; epidermal transglutaminase; histidine-tRNA; signal recognition peptide; Mi-2; Jo1; Glutamic acid decarboxylase, HSP60; HSP70; HSP90; IGRP; insulin; carboxypeptidase H; insulinoma antigen-2; IA-2beta; ICA69; ZnT8; chromogranin A; IAPP; scl70; topoisomerase; histones; Basement Membrane Collagen Type IV; enolase; thyroid peroxidase; thyroglobulin; complement component 3; voltage-gated calcium channels; Q-type calcium channel, synaptogagmin, muscarinic acetylcholine receptor M1; SMA; LKM-1; LKM-2; LKM-3; soluble liver antigen; SLA; LP; major peripheral myelin protein P0; myeloperoxidase; GQ1b; U1-RNP; Kir4.1; nicotinic acetylcholine receptor; MuSK protein; hypocretin; orexin; keratin; AQP4; Yo; Hu; glutamate receptor; Desmoglein 3; p62; sp100; Ro; LA; glycoproteins IIb-IIIa or Ib-IX; ADAMTS13; cardiolipin; β2 glycoprotein I; HPA-1a; HPA-5b; IFN-gamma, IL-1, TNF-alpha; GMCSF, portions thereof, and combinations thereof.
6. The method of any of paragraphs 1-5, wherein the contacting is performed ex vivo or in vitro.
7. The method of any of paragraphs 1-5, wherein the contacting is performed in vivo.
8. The method of any of paragraphs 1-7, wherein the immunosuppressive dendritic cell comprises an increased expression of IL-27, as compared to a dendritic cell not contacted with the IL-27 agonist.
9. The method of any of paragraphs 1-8, wherein the immunosuppressive dendritic cell comprises an increased expression of CD39, as compared to a dendritic cell not contacted with the IL-27 agonist.
10. The method of any of paragraphs 1-9, wherein the immunosuppressive dendritic cell comprises a reduced production of an effector polarizing cytokine and/or an increased production of an anti-inflammatory cytokine, as compared to a dendritic cell not contacted with the IL-27 agonist.
11. The method of paragraph 10, wherein the effector polarizing cytokine comprises IL-12 and/or IL-6.
12. The method of paragraph 10 or 11, wherein the anti-inflammatory cytokine comprises TGFβ1, IL-10, IFN-β, or any combinations thereof.
13. The method of any of paragraphs 1-12, wherein the IL-27 agonist comprises a recombinant IL-27 protein or peptide.
14. The method of any of paragraphs 1-13, wherein the dendritic cell is derived from a spleen, lymph node, blood, monocyte, and/or hematopoietic progenitor cell.
15. An immunosuppressive dendritic cell produced by the method of any of paragraphs 1-14.
16. A method of treating an autoimmune disease or disorder comprising administering to a patient in need thereof a dendritic cell (DC)-targeting composition comprising (a) an agent that stimulates IL-27/ectonucleotidase CD39 axis signaling, and (b) a DC-binding agent.
17. The method of paragraph 16, wherein the agent comprises an IL-27 agonist.
18. The method of paragraph 16 or 17, wherein the agent comprises a CD39 agonist.
19. The method of any of paragraphs 16-18, wherein the agent comprises an ATP degrading agonist.
20. The method of paragraph 19, wherein the ATP degrading agonist comprises apyrase.
21. The method of any of paragraphs 16-20, wherein the DC-binding agent comprises an antibody against Clec9A and/or DEC205.
22. The method of any of paragraphs 16-21, wherein the DC-targeting composition further comprise an autoimmune antigen.
23. The method of paragraph 22, wherein the autoimmune antigen is selected from the group consisting of myelin basic protein (MBP); proteolipid protein (PLP); myelin oligodendrocyte glycoprotein (MOG), myelin-associated oligodendrocytic basic protein cardiac myosin; outer surface protein (OSP); myelin associated glycoprotein (MAG); neurofilaments; interferon omega; transglutaminase; aromatic acid carboxylase; 17-hydroxylase; 21-hydroxylase, cardiolipin; pyruvate dehydrogenase; β2 glycoprotein I; phosphatidylserine; apoH; Annexin A5; LKM-1; soluble liver antigen; carbonic anhydrase; gpIIb-IIIa or 1b-IX; type XVII collagen; tissue transglutaminase; gliadin; GD1a; GQ1b; BP-1; BP-2; epidermal transglutaminase; histidine-tRNA; signal recognition peptide; Mi-2; Jo1; Glutamic acid decarboxylase, HSP60; HSP70; HSP90; IGRP; insulin; carboxypeptidase H; insulinoma antigen-2; IA-2beta; ICA69; ZnT8; chromogranin A; IAPP; scl70; topoisomerase; histones; Basement Membrane Collagen Type IV; enolase; thyroid peroxidase; thyroglobulin; complement component 3; voltage-gated calcium channels; Q-type calcium channel, synaptogagmin, muscarinic acetylcholine receptor M1; SMA; LKM-1; LKM-2; LKM-3; soluble liver antigen; SLA; LP; major peripheral myelin protein P0; myeloperoxidase; GQ1b; U1-RNP; Kir4.1; nicotinic acetylcholine receptor; MuSK protein; hypocretin; orexin; keratin; AQP4; Yo; Hu; glutamate receptor; Desmoglein 3; p62; sp100; Ro; LA; glycoproteins IIb-IIIa or Ib-IX; ADAMTS13; cardiolipin; β2 glycoprotein I; HPA-1a; HPA-5b; IFN-gamma, IL-1, TNF-alpha; GMCSF, portions thereof, and combinations thereof.
24. The method of any of paragraphs 16-23, wherein the DC-binding agent and the optional autoimmune antigen are fused to the agent that stimulates IL-27/ectonucleotidase CD39 axis signaling.
25. The method of any of paragraphs 16-23, wherein the DC-targeting composition comprises a nanoparticle, the nanoparticle comprising the agent that stimulates IL-27/ ectonucleotidase CD39 axis signaling, the DC-binding agent and the optional autoimmune antigen.

26. The method of paragraph 25, wherein the agent and the optional autoimmune antigen distribute on a surface of the nanoparticle.

27. The method of paragraph 25 or 26, wherein the agent and the optional autoimmune antigen are encapsulated in the nanoparticle.

28. The method of any of paragraphs 25-27, wherein the nanoparticle further comprises on its surface a PEG layer.

29. The method of any of paragraphs 25-28, wherein the nanoparticle is a gold nanoparticle.

30. The method of any of paragraphs 25-29, wherein the autoimmune disease or disorder is multiple sclerosis.

31. The method of any of paragraphs 25-30, wherein the autoimmune disease or disorder is encephalomyelitis.

32. The method of any of paragraphs 25-31, wherein the autoimmune disease or disorder is type 1 diabetes.

33. A method of treating an autoimmune disease or disorder comprising administering a composition comprising a population of immunosuppressive dendritic cells of paragraph 15.

34. The method of paragraph 33, wherein the population of immunosuppressive dendritic cells are autologous dendritic cells.

35. The method of paragraph 33 or 34, wherein the composition further comprises an autoimmune antigen.

36. The method of paragraph 35, wherein the autoimmune antigen is selected from the group consisting of myelin basic protein (MBP); proteolipid protein (PLP); myelin oligodendrocyte glycoprotein (MOG), myelin-associated oligodendrocytic basic protein cardiac myosin; outer surface protein (OSP); myelin associated glycoprotein (MAG); neurofilaments; interferon omega; transglutaminase; aromatic acid carboxylase; 17-hydroxylase; 21-hydroxylase, cardiolipin; pyruvate dehydrogenase; β2 glycoprotein I; phosphatidylserine; apoH; Annexin A5; LKM-1; soluble liver antigen; carbonic anhydrase; gpIIb-IIIa or 1b-IX; type XVII collagen; tissue transglutaminase; gliadin; GD1a; GQ1b; BP-1; BP-2; epidermal transglutaminase; histidine-tRNA; signal recognition peptide; Mi-2; Jo1; Glutamic acid decarboxylase, HSP60; HSP70; HSP90; IGRP; insulin; carboxypeptidase H; insulinoma antigen-2; IA-2beta; ICA69; ZnT8; chromogranin A; IAPP; scl70; topoisomerase; histones; Basement Membrane Collagen Type IV; enolase; thyroid peroxidase; thyroglobulin; complement component 3; voltage-gated calcium channels; Q-type calcium channel, synaptogagmin, muscarinic acetylcholine receptor M1; SMA; LKM-1; LKM-2; LKM-3; soluble liver antigen; SLA; LP; major peripheral myelin protein P0; myeloperoxidase; GQ1b; U1-RNP; Kir4.1; nicotinic acetylcholine receptor; MuSK protein; hypocretin; orexin; keratin; AQP4; Yo; Hu; glutamate receptor; Desmoglein 3; p62; sp100; Ro; LA; glycoproteins IIb-IIIa or Ib-IX; ADAMTS13; cardiolipin; β2 glycoprotein I; HPA-1a; HPA-5b; IFN-gamma, IL-1, TNF-alpha; GMCSF, portions thereof, and combinations thereof.

Some Selected Definitions

For convenience, certain terms employed in the entire application (including the specification, examples, and appended claims) are collected here. Unless defined otherwise, all technical and scientific terms used herein have the same meaning as commonly understood by one of ordinary skill in the art to which this invention belongs.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used to described the present invention, in connection with numeric values means±5%.

As used herein and throughout the specification, the term "antagonist" is used in the broadest sense, and includes any molecule that partially or fully blocks, inhibits, or neutralizes a biological activity of a native polypeptide disclosed herein. In a similar manner, the term "agonist" is used in the broadest sense and includes any molecule that mimics a biological activity of a native polypeptide disclosed herein. Suitable agonist or antagonist molecules specifically include agonist or antagonist antibodies or antibody fragments, fragments or amino acid sequence variants of native polypeptides, peptides, antisense oligonucleotides, small organic molecules, recombinant proteins or peptides, etc. Methods for identifying agonists or antagonists of a polypeptide can comprise contacting a polypeptide with a candidate agonist or antagonist molecule and measuring a detectable change in one or more biological activities normally associated with the polypeptide.

In one aspect, the present invention relates to the herein described compositions, methods, and respective component(s) thereof, as essential to the invention, yet open to the inclusion of unspecified elements, essential or not ("comprising"). In some embodiments, other elements to be included in the description of the composition, method or respective component thereof are limited to those that do not materially affect the basic and novel characteristic(s) of the invention ("consisting essentially of"). This applies equally to steps within a described method as well as compositions and components therein. In other embodiments, the inventions, compositions, methods, and respective components thereof, described herein are intended to be exclusive of any element not deemed an essential element to the component, composition or method ("consisting of").

All patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these.

As used herein, a "subject" can mean a human or an animal. Examples of subjects include primates (e.g., humans, and monkeys). Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, and avian species, e.g., chicken, emu, ostrich. A patient or a subject includes any subset of the foregoing, e.g., all of the above, or includes one or more groups or species such as humans, primates or rodents. In certain embodiments of the aspects described herein, the subject is a mammal, e.g., a primate, e.g., a human. The terms, "patient" and "subject" are used interchangeably herein. A subject can be male or female. The term "patient" and "subject" does not denote a particular age. Thus, any mammalian subjects from adult to newborn subjects, as well as fetuses, are intended to be covered.

In one embodiment, the subject or patient is a mammal. The mammal can be a human, non-human primate, mouse, rat, dog, cat, horse, or cow, but are not limited to these examples. In one embodiment, the subject is a human being. In another embodiment, the subject can be a domesticated animal and/or pet.

As used herein and throughout the specification, the terms "administering," or "administration" refer to the placement of an agent or composition (e.g., a DC-targeting composition described herein that modulates the expression and/or activity of IL-27, IL-27RA, and/or CD39 in DCs, and/or level of eATP, and/or a composition comprising immunosuppressive dendritic cells described herein) into a subject by a method or route which results in at least partial localization of such agents at a desired site, such as a target site, such that a desired effect(s) is produced.

In some embodiments of this aspect and other aspects described herein, the DC-targeting compositions comprising an agent for modulating the expression and/or activity of IL-27, IL-27RA, and/or CD39 in DCs, and/or level of eATP, and/or a composition comprising immunosuppressive dendritic cells can be administered to a subject by any mode of administration that delivers the agent systemically or to a desired surface, organ, or target, and can include, but is not limited to injection, infusion, instillation, and inhalation administration. To the extent that such agents can be protected from inactivation in the gut, oral administration forms are also contemplated. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In some embodiments, the DC-targeting compositions comprising an agent for modulating the expression and/or activity of IL-27, IL-27RA, and/or CD39 in DCs, and/or level of eATP, and/or a composition comprising immunosuppressive dendritic cells for use in the methods described herein are administered by intravenous infusion or injection. In some embodiments, a composition comprising immunosuppressive dendritic cells described herein for use in the methods described herein can be administered by implantation, e.g., via a catheter.

The phrases "parenteral administration" and "administered parenterally" as used herein, refer to modes of administration other than enteral and topical administration, usually by injection. The phrases "systemic administration," "administered systemically", "peripheral administration" and "administered peripherally" as used herein refer to the administration of a DC-targeting composition comprising an agent for modulating the expression and/or activity of IL-27, IL-27RA, and/or CD39 in DCs, and/or level of eATP, and/or a composition comprising immunosuppressive dendritic cells, other than directly into a target site, tissue, or organ, such that it enters the subject's circulatory system and, thus, is subject to metabolism and other like processes.

As used herein, the term "peptidomimetic" refers to a molecule capable of folding into a defined three-dimensional structure similar to a natural peptide.

As used herein, the term "small molecules" refers to natural or synthetic molecules including, but not limited to, peptides, peptidomimetics, amino acids, amino acid analogs, polynucleotides, polynucleotide analogs, aptamers, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

EXAMPLES

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

Example 1. Comparison of Expression of IL-27 Receptor α-Chain (IL-27RA) in Conventional Dendritic Cells (cDCs) and Plasmacytoid DCs To determine the role of IL-27 signaling in DCs on the regulation of autoimmunity, the expression of IL-27RA was first analyzed in plasmacytoid DCs (pDCs; F4/80$^-$CD11b$^-$ CD11c$^{lo}$ B220$^+$ MHC class II$^{lo}$ Ly6c$^+$) and cDCs (F4/80$^-$ CD11b$^+$ CD11c$^+$ B220$^-$ MHC class II$^+$ Ly6c$^-$) isolated from naive mice by flow cytometry (FIG. 1). IL-27RA was expressed mainly in cDCs, with only low or absent expression on pDCs (FIG. 2A). Similar results were obtained for IL-27RA expression by quantitative PCR and immunoblot analysis of sorted pDCs and cDCs (FIGS. 2B-2C). Thus, there is higher IL-27RA expression in cDCs than in plasmacytoid DCs. The expression pattern of IL-27RA indicated that IL-27 controls the activity of cDCs.

Example 2. Effect of IL-27 on the Function of cDCs

After antigen uptake in the presence of DC-maturing stimuli, DCs upregulate their expression of major histocompatibility complex (MHC) class II and costimulatory molecules[21]. To determine the effects of IL-27 on DC activation, splenic cDCs from naive mice were pretreated with vehicle or IL-27 and their response to activation with lipopolysaccharide from *Escherichia coli* (ecLPS) were determined. Pretreatment of cDCs with IL-27 followed by activation with ecLPS led to significantly lower expression of MHC class II and the costimulatory molecules CD40, CD80 and CD86 than that of cDCs activated with ecLPS without IL-27 pretreatment (FIGS. 3A-3I).

Figure 3A:
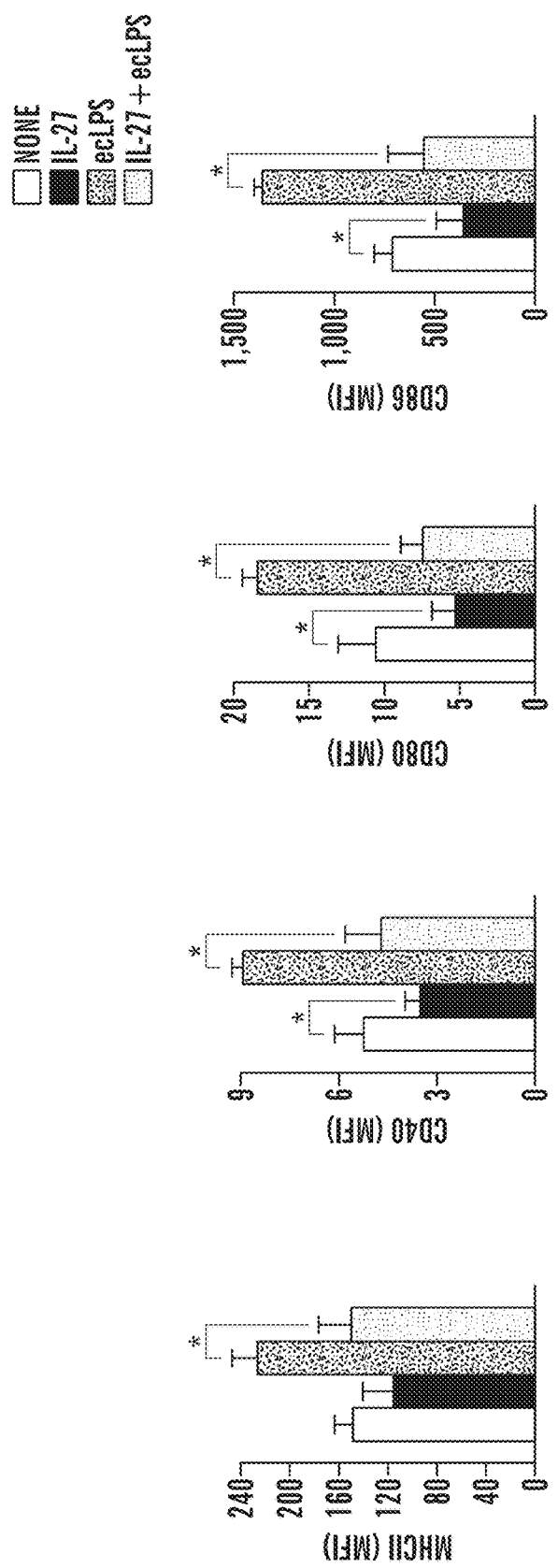
Figure 3B:
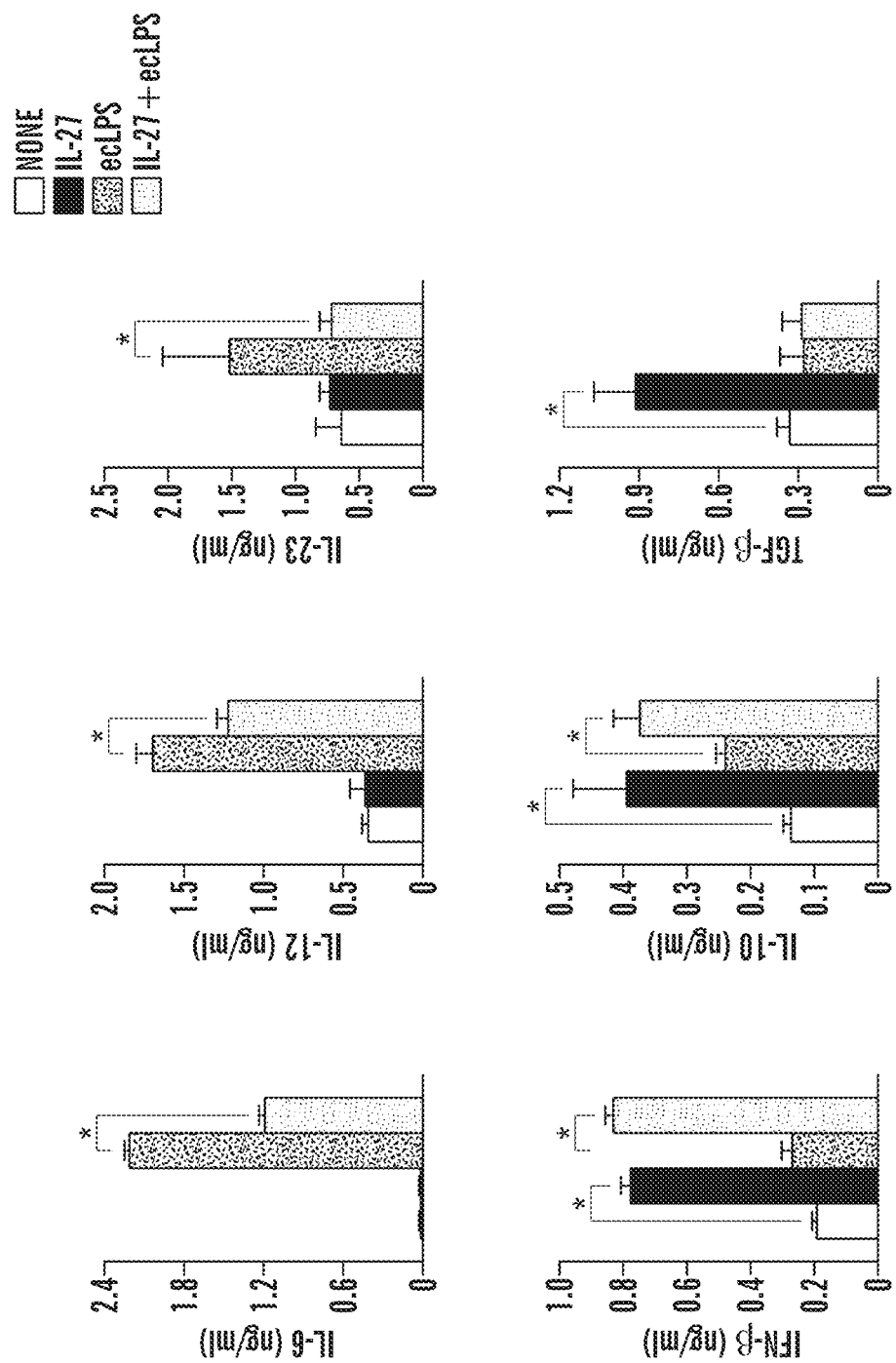

DCs control T cell differentiation via the secretion of polarizing cytokines[21]. Pretreatment of splenic cDCs with IL-27 followed by activation with ecLPS led to significantly lower production of IL-12 and of IL-6 and IL-23 (which promote the differentiation of TH1 and TH17 cells, respectively) than that of cDCs activated with ecLPS without IL-27 pretreatment (FIG. 3B). Pretreatment of cDCs with IL-27 followed by activation with ecLPS also upregulated Il27 expression (FIG. 3C), which indicated a positive feedback loop for IL-27 production. Indeed, in those conditions increased production of IFN-β was detected (FIG. 3B). Increased production of IFN-β was previously reported to act in an autocrine manner to trigger IL-27 production[9]. Increased production of IL-10 in those conditions was detected; and increased production of transforming growth factor-β1 (TGF-β1) were also detected only in response to treatment with IL-27 (FIG. 3B). Together these data showed that IL-27 decreased the production of cytokines that promote the differentiation of effector TH1 and TH17 cells, while it enhanced the production of anti-inflammatory cytokines by cDCs.

Figure 3F:
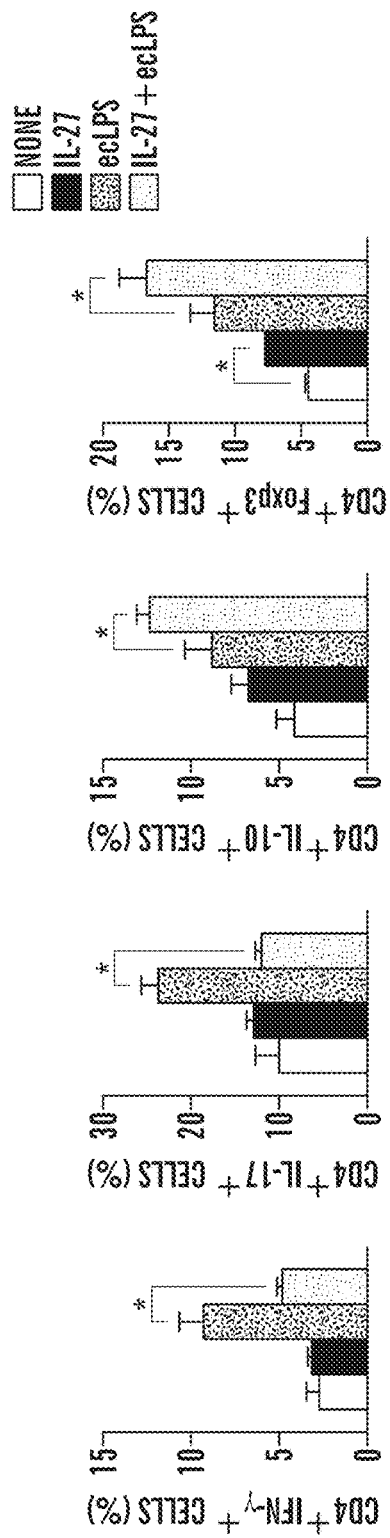

The effects of IL-27 on the expression of MHC class II, costimulatory molecules and cytokines suggests that IL-27 affects the ability of DCs to activate and polarize T cells into specific subsets. Thus, cDCs were pretreated with IL-27 and they were activated with ecLPS, then extensively washed and their ability to activate naive 2D2 CD4+ T cells was assessed in the presence of their cognate target antigen: an epitope of amino acids 35-55 of myelin oligodendrocyte glycoprotein (MOG(35-55)). Pretreatment of cDCs with IL-27 followed by activation with ecLPS led to a significantly lower proliferative response of naive 2D2 T cells to MOG(35-55) than that elicited by cDCs treated with ecLPS without IL-27 pretreatment (FIG. 3D). Moreover, the cDCs pretreated with IL-27 and activated with ecLPS had a decreased ability to induce the production of IFN-γ and IL-17 by T cells, as measured by enzyme-linked immunosorbent assay and intracellular cytokine staining (FIGS. 3E-3F). Conversely, pretreatment of cDCs with IL-27 before activation with ecLPS boosted their ability to promote the differentiation of IL-10+ and Foxp3+ CD4+ T cells (FIGS. 3E-3F). Similar effects for bone marrow-derived DCs pretreated with IL-27 and activated with ecLPS were also observed (data not shown).

Figure 3G:
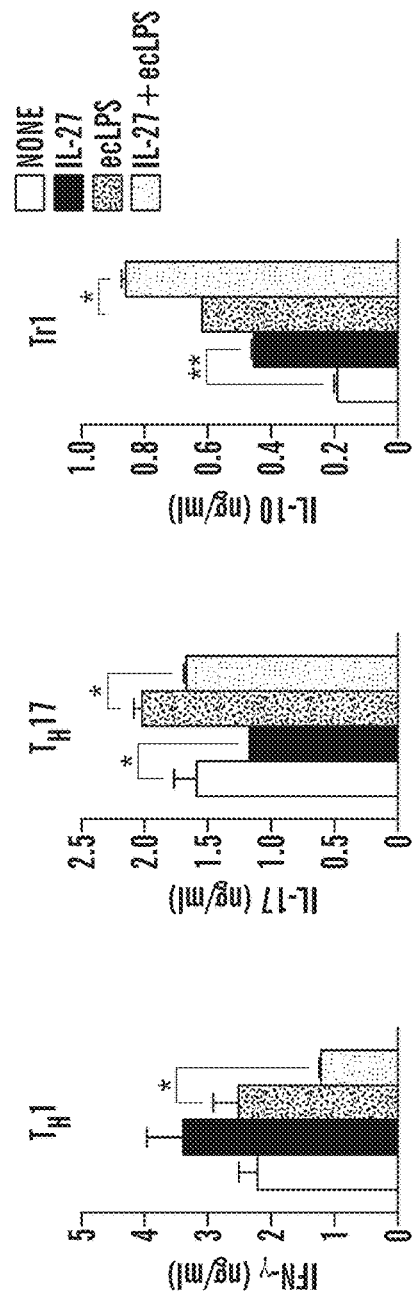
Figure 3H:
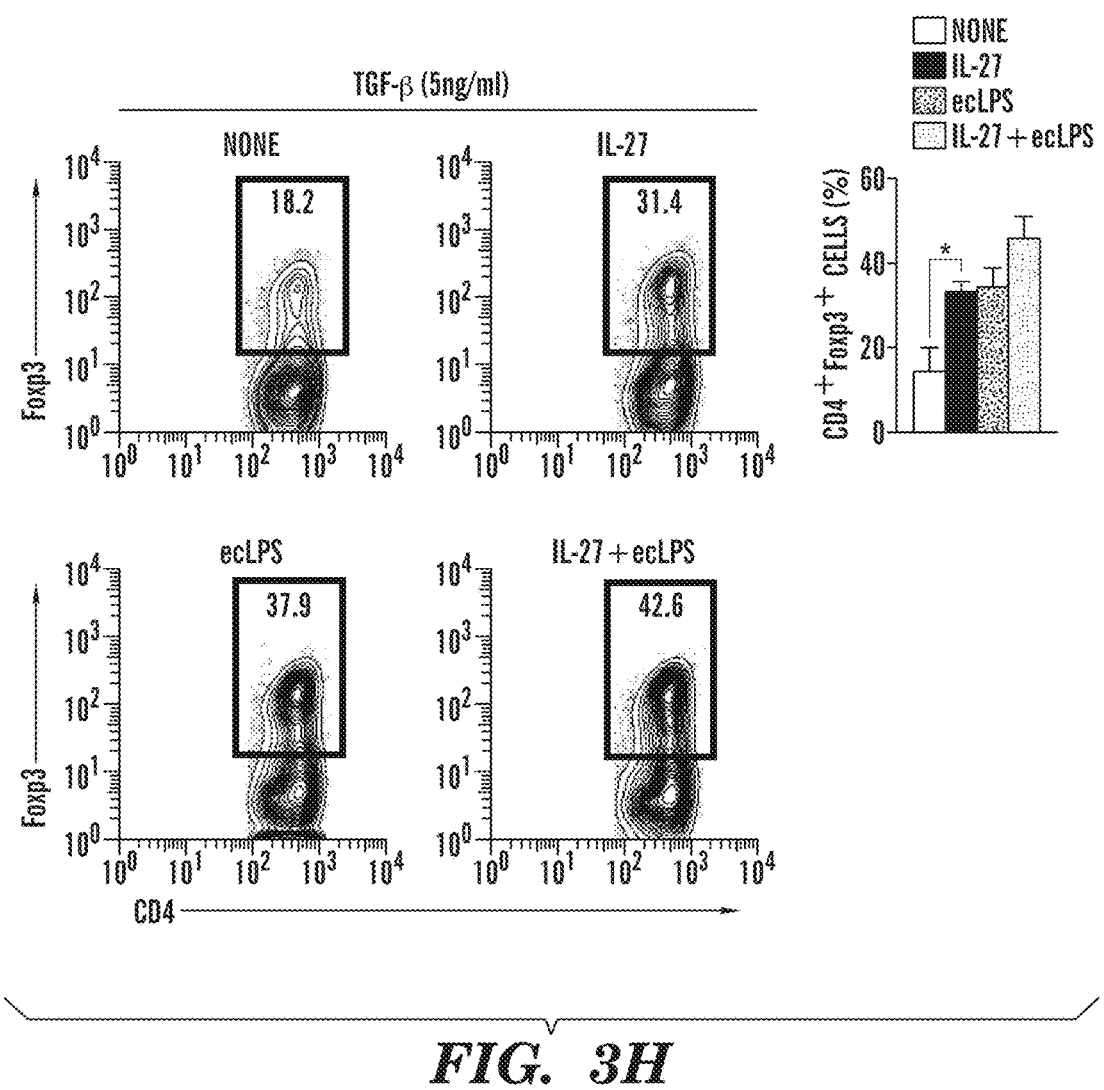
Figure 3I:
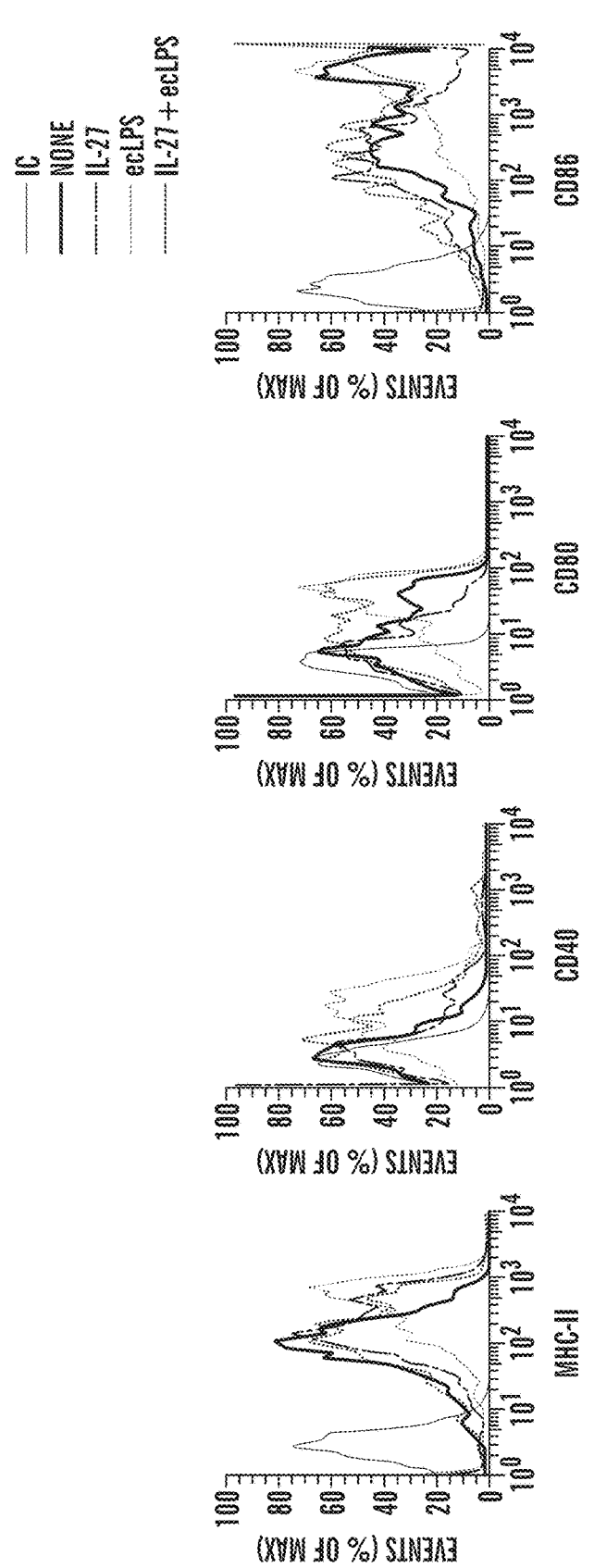

IL-27 is previously reported to act directly on T cells to suppress their differentiation into effector T cells[12, 15-17]. The inventors have found that cDCs pretreated IL-27 and activated with ecLPS showed a diminished ability to trigger the production of IFN-γ and IL-17 by T cells in the presence of exogenously added TH1- and TH17-polarizing cytokines than that of cDCs activated with ecLPS without IL-27 pretreatment (FIG. 3G). Conversely, pretreatment of cDCs with IL-27 increased IL-10 production and expression of the transcription factor Foxp3 in T cells when Tr1-polarizing cytokines or cytokines that polarize differentiation into Foxp3+ Treg cells were added to the coculture (FIGS. 3G-3H), contemplating that IL-27 signaling in DCs modulated T cell differentiation in vivo even in the context of inflammation or other physiological conditions that generate a polarizing cytokine milieu. Together these data showed that IL-27 signaling controlled the antigen-presenting function of cDCs.

Example 3. Effect of IL-27RA in DCs on Development of Experimental Autoimmune Encephalomyelitis (EAE)

Figure 4D:
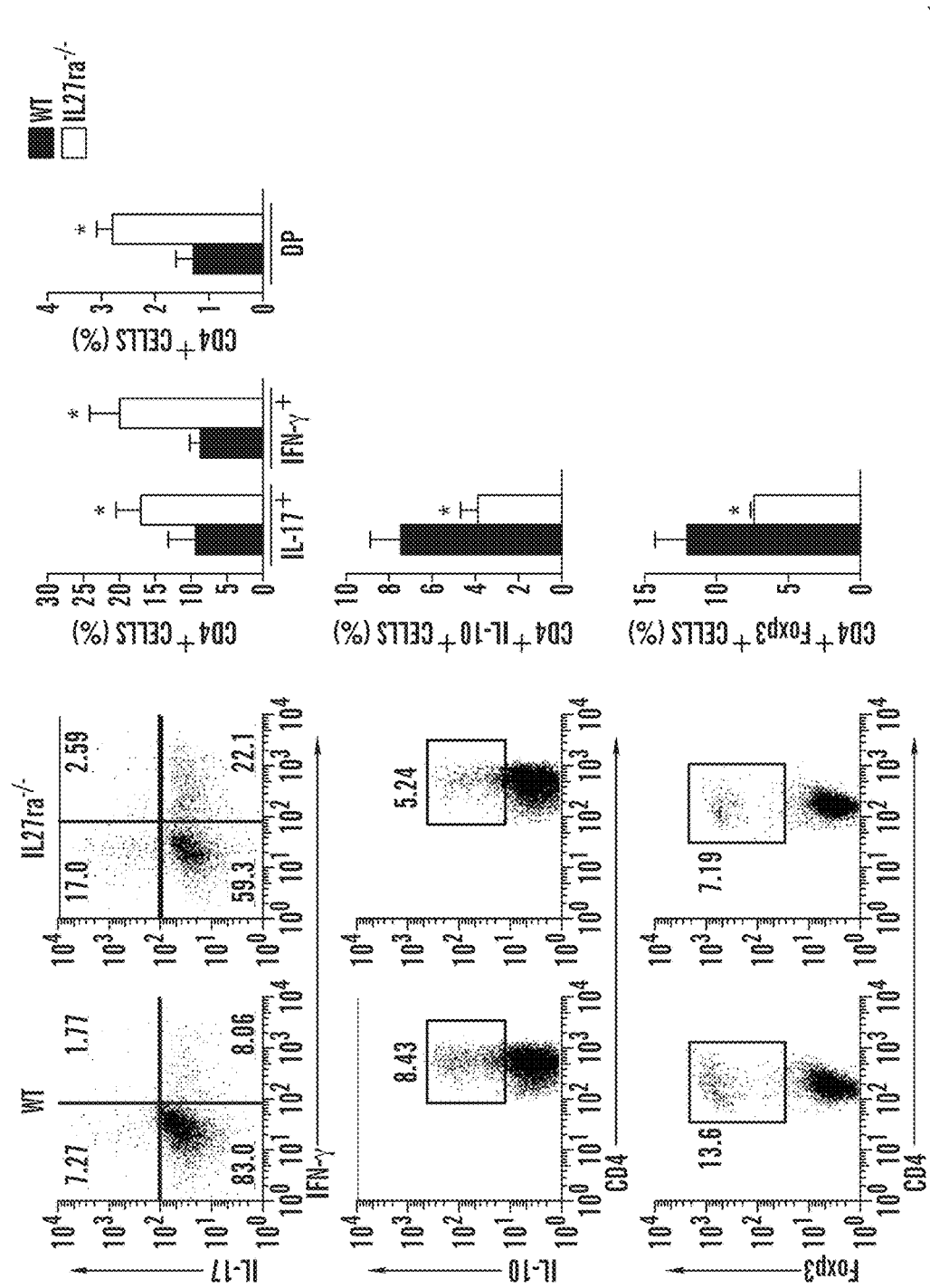

IL-27 has been previously reported to play a role in the control of CNS inflammation during EAE[12, 13, 15]. A significant worsening of EAE in IL-27RA-deficient (Il27ra-/-) mice, characterized by an increase in the frequency of CNS-infiltrating IFN-γ+ and IL-17+ CD4+ T cells and a lower frequency of IL-10+ CD4+ T cells were found (FIGS. 4A-4B). Il27ra-/- mice also showed an increased recall response to MOG(35-55) and an increased frequency of CD4+ CD44+ CD40L$^{hi}$ IFNγ+, IL-17+ and IFN-γ+ IL-17+ CD4+ T cells in the lymph nodes and spleen, concomitant with a decreased frequency of Foxp3+ and IL-10+ CD4+ T cells (FIGS. 4C-4D).

Figure 4E:
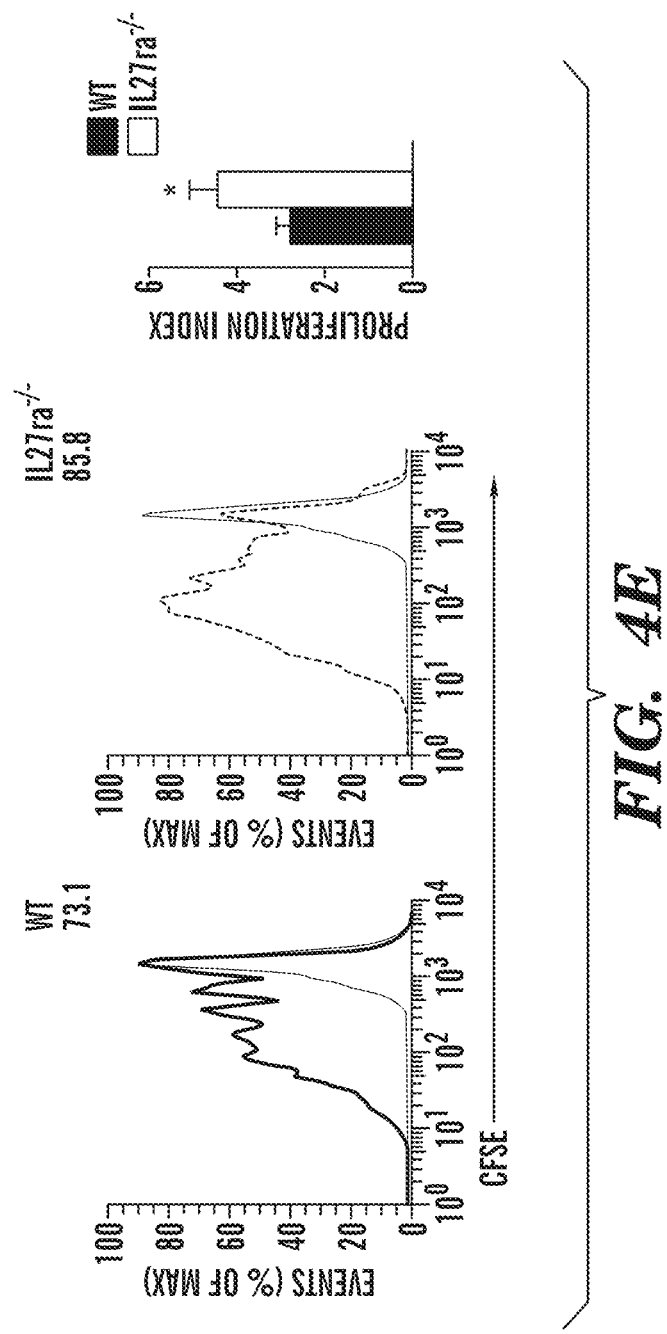

The previously-reported effects of IL-27 on encephalitogenic and Treg cells[14, 15, 17] would indicate that the worsening of EAE in the Il27ra$^{-/-}$ mice resulted from the lack of IL-27 signaling in T cells. It is not known whether IL-27 can act on additional cells beyond T cells to limit the development of EAE. The Il27ra$^{-/-}$ mice had non-cell-specific deletion of IL-27RA. To determine the role of IL-27 signaling in DCs during EAE, cDCs were isolated from wild-type and Il27ra-/- mice 21 d after disease induction. It was found that cDCs from Il27ra-/- mice showed an increased ability to activate naive 2D2 T cells in the presence of MOG(35-55) (FIG. 4E), which indicated that defective IL-27 signaling in DCs contributed to the worsening of EAE in Il27ra-/- mice.

Figure 5A:
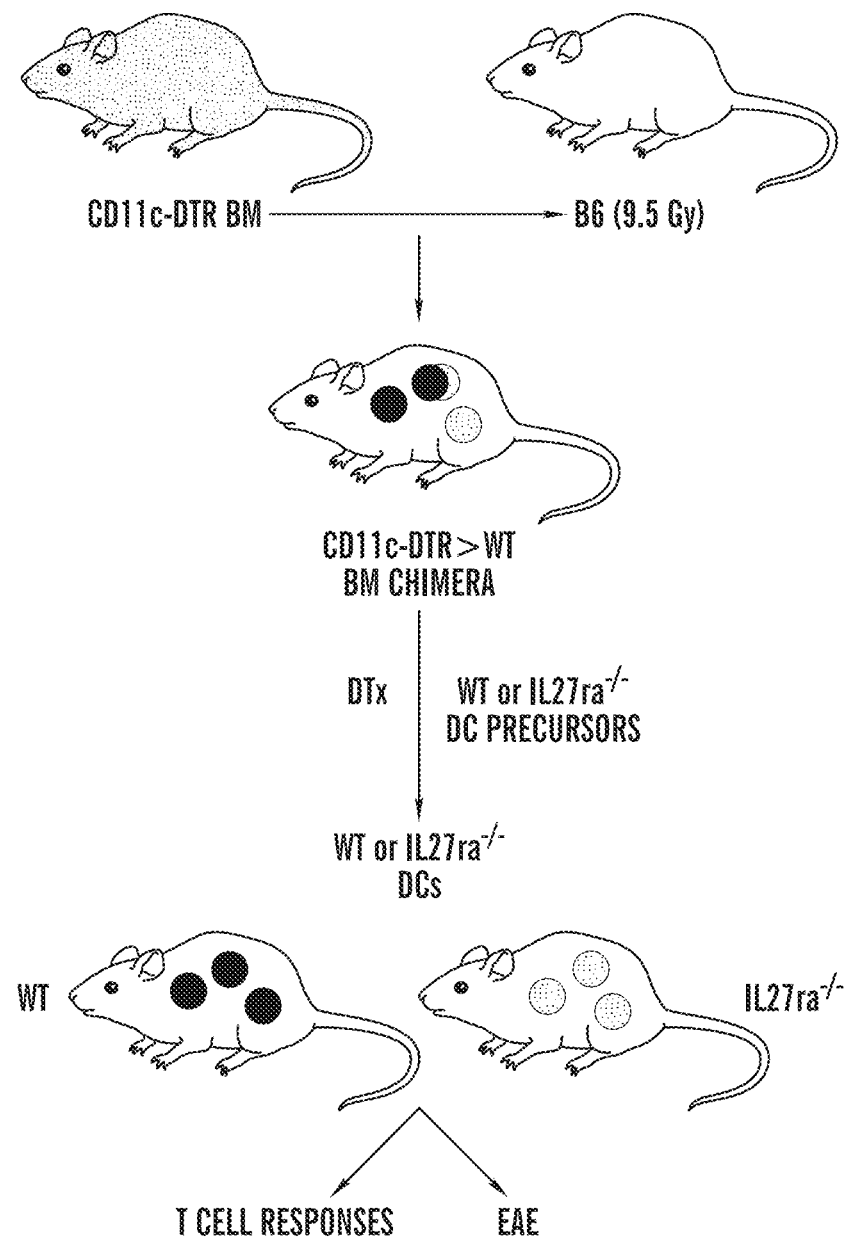
FIGS. 5A-5H show generation of mice lacking IL-27RA expression in DCs.
Figure 5B:
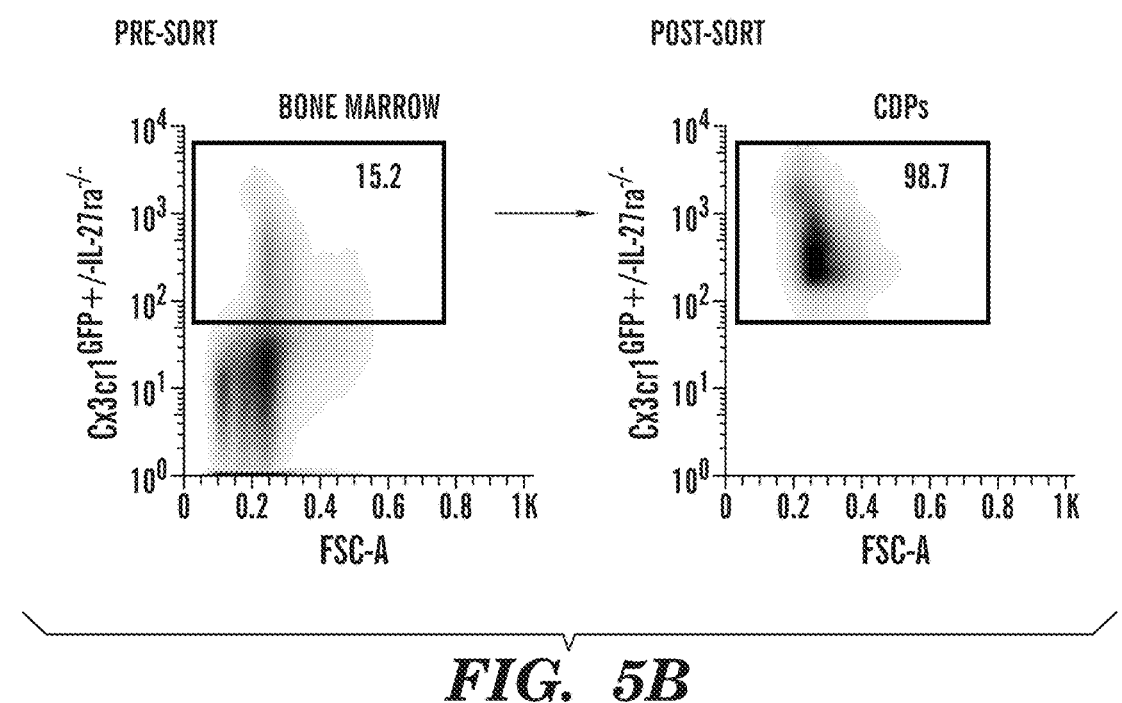
Figure 5C:
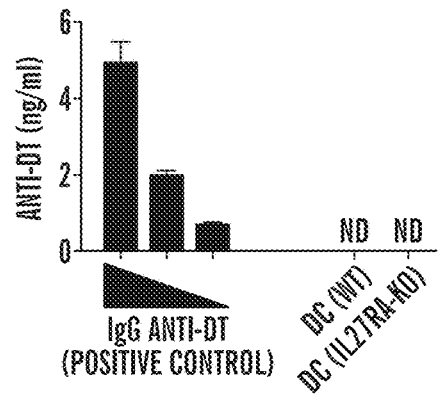

In vivo, DCs are generally influenced by their interactions with T cells and the cytokine milieu. Thus, the increased antigen-presenting function of cDCs isolated from Il27ra-/- mice might have reflected the exposure of the DCs to a more inflammatory cytokine milieu and not direct effects of IL-27 on DCs. To determine the role of IL-27 signaling in DCs during EAE, a chimera-based approach was used to generate mice lacking IL-27RA expression in DCs (FIG. 5A). For this, lethally irradiated wild-type mice were reconstituted with bone marrow cells from mice that express the diphtheria toxin receptor (DTR) under the control of the promoter of the gene encoding CD11c (Itgax; called 'CD11c-DTR' mice herein). After reconstitution, these mice can be depleted of CD11c+ DCs by the administration of diphtheria toxin (DTx)[22]. DTx cannot be chronically administered to CD11c-DTR mice because of adverse side effects; however, no adverse effects are associated with the chronic administration of DTx to chimeras generated by the reconstitution of wild-type mice with bone marrow from CD11c-DTR mice (CD11c-DTR→WT)[4]. Thus, 2 months after reconstitution of wild-type mice with CD11c-DTR bone marrow, those CD11c-DTR→WT chimeras of DTR+ DCs were depleted by chronic administration of DTx and their DC compartment was reconstituted with DC precursors from wild-type mice (to generate 'DC(WT)' mice) or from Il27ra-/- mice (to generate 'DC(IL-27RA-KO)' mice) (FIG. 5B). DTx was administered to DC(WT) and DC(IL-27RA-KO) mice once every other day until the completion of the experiment and detected no antibodies to DTx after 2 months of DTx administration (FIG. 5C).

Figure 5D:
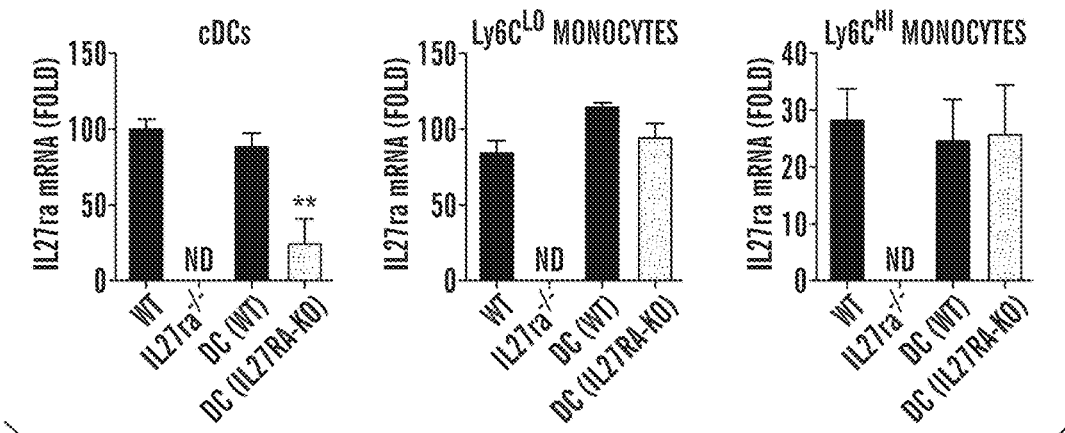
Figure 5E:
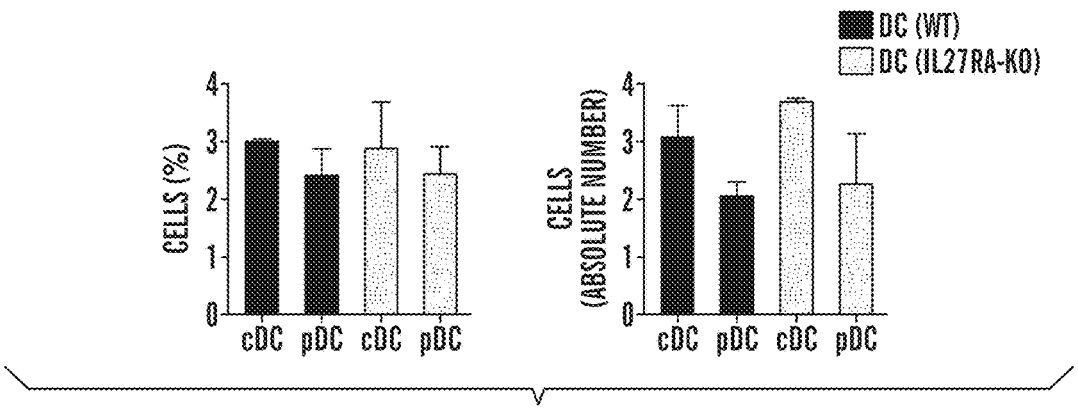
Figure 5F:
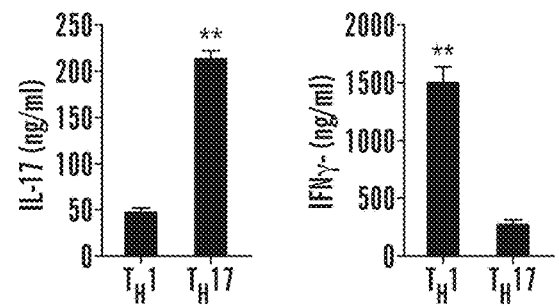
Figure 5G:
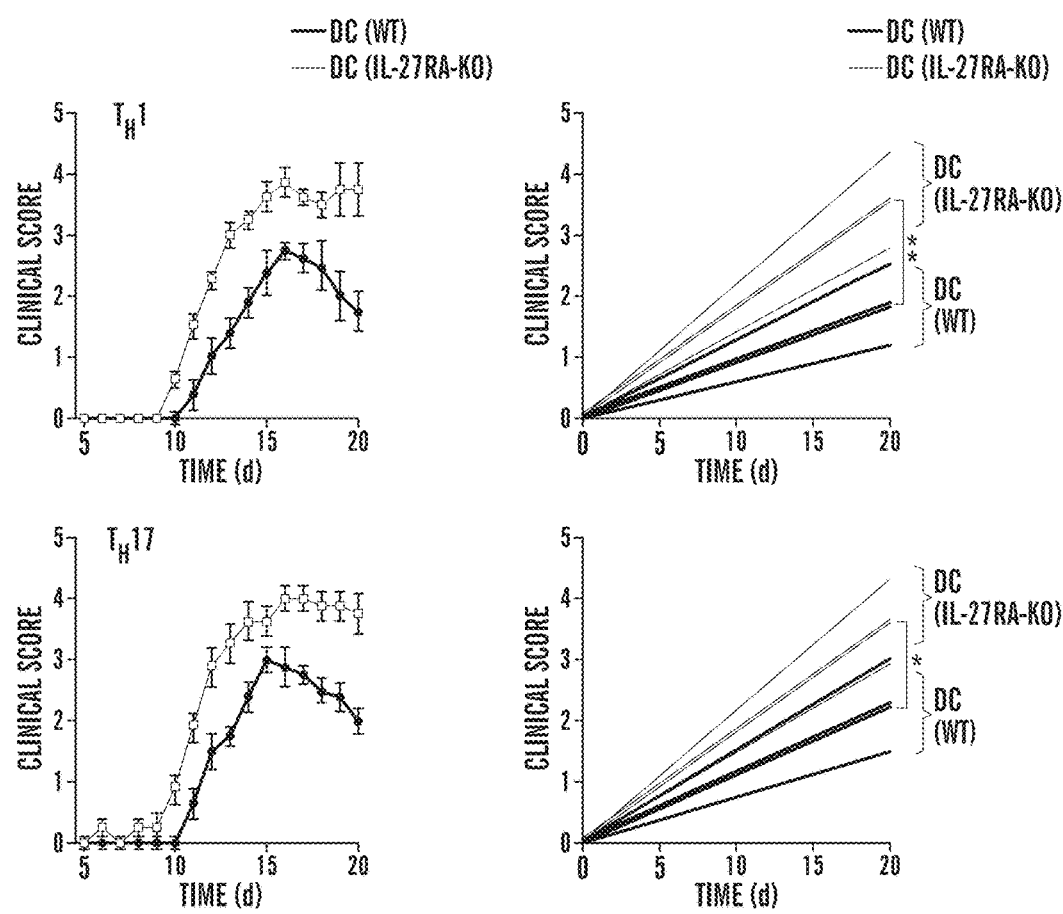
Figure 5H:
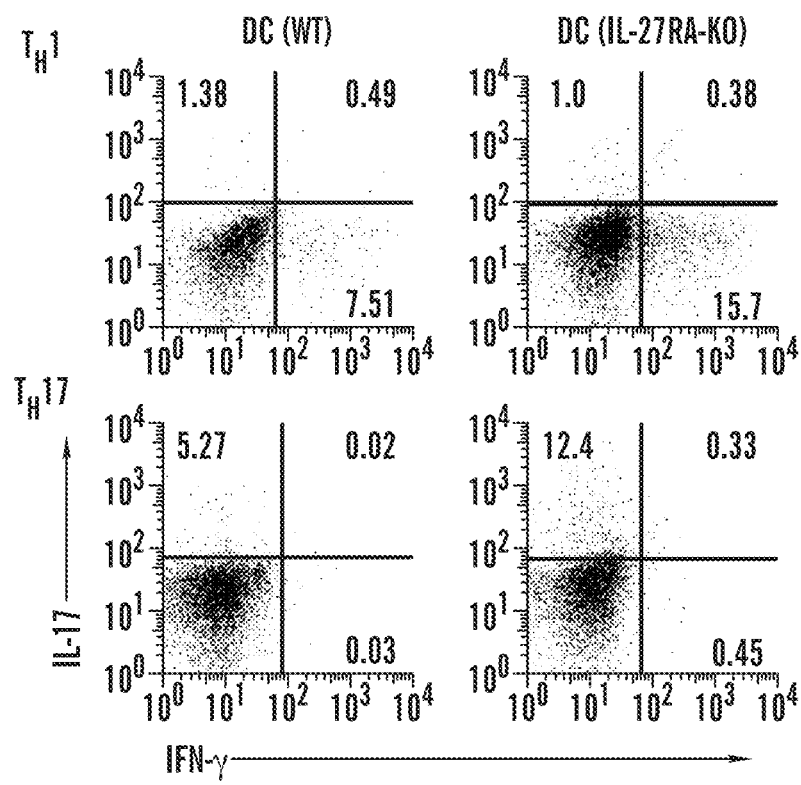
Figure 6A:
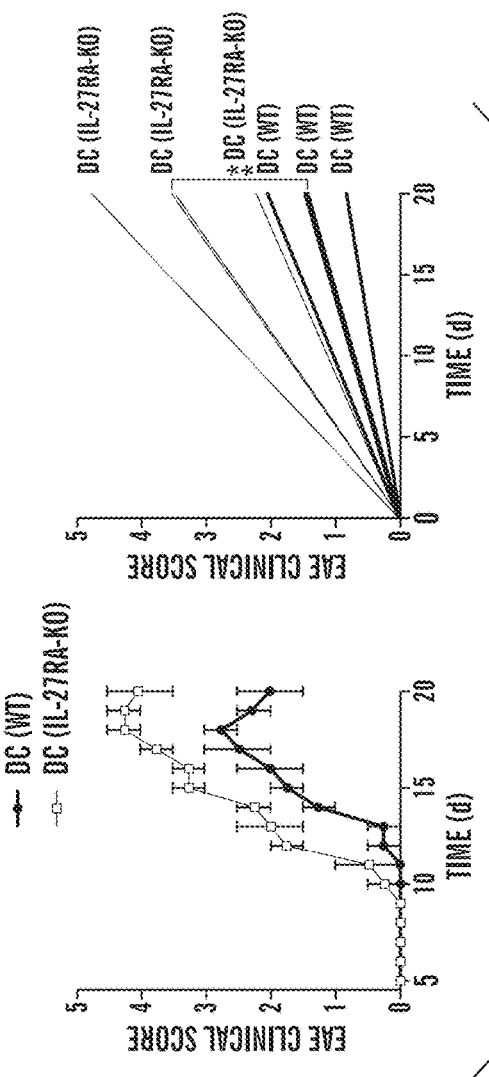
FIGS. 6A-6I show that IL-27RA signaling in cDCs controls T cell differentiation and EAE development.
Figure 6B:
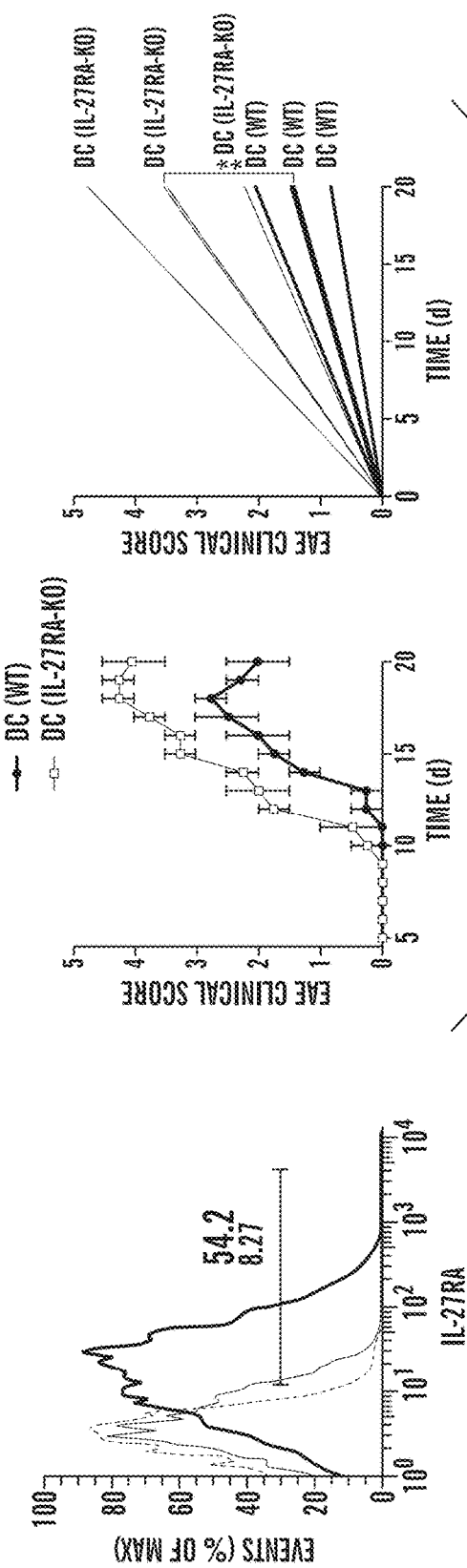
Figure 6D:
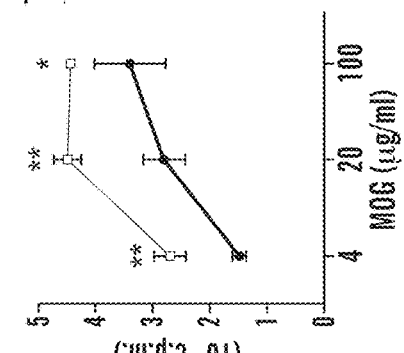
Figure 6C:
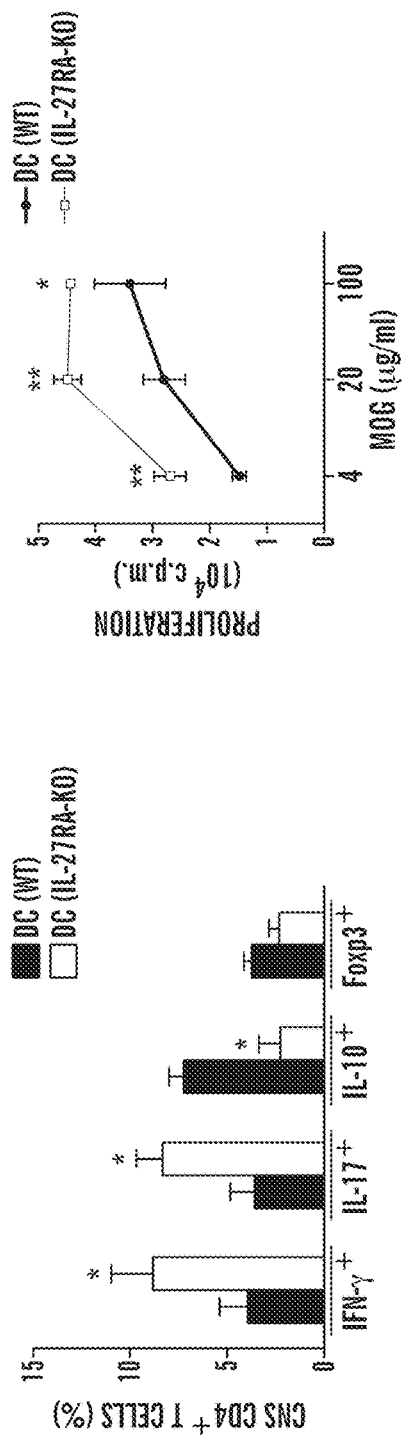
Figure 6E:
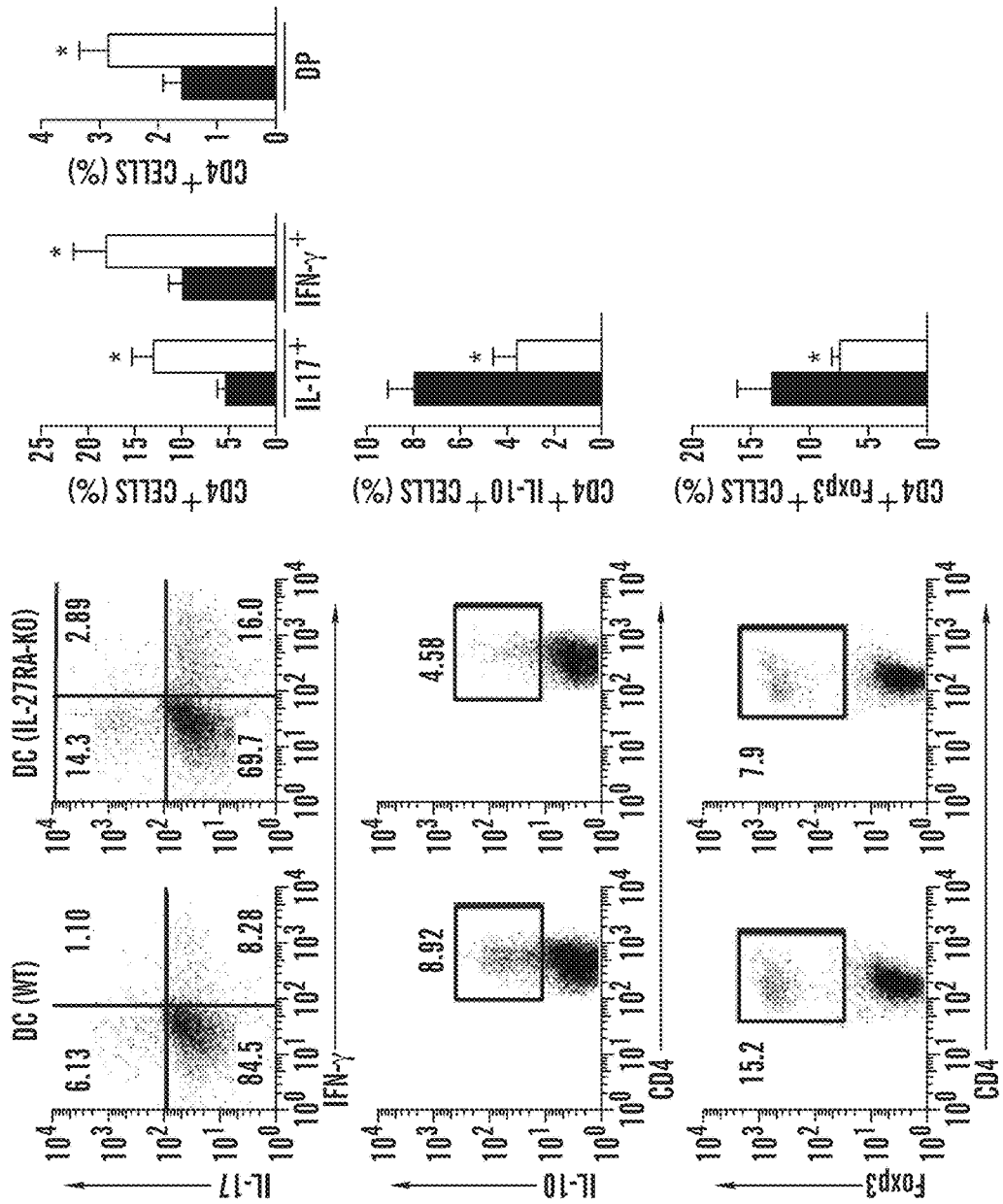

DC(IL-27RA-KO) mice had significantly lower IL-27RA expression in cDCs but not in other antigen-presenting cell (APC) populations than did DC (WT) mice (FIG. 6A and FIG. 5D). No difference was detected between DC(WT) and DC(IL-27RA-KO) mice in the frequency or absolute number of DCs (FIG. 5E). Treatment with MOG(35-55) resulted in faster development of EAE in DC(IL-27RA-KO) mice than in DC(WT) mice; DC(IL27RA-KO) mice also reached significantly higher disease scores than did their DC(WT) counterparts (FIG. 6B). The worsening of EAE in DC(IL-27RA-KO) mice was associated with a greater frequency of TH1 and TH17 cells in the CNS and significantly fewer IL-10+ T cells than that in DC(WT) mice (FIG. 6C). Moreover, analysis of the CD4+ CD44+ CD40L$^{hi}$ splenic T cell compartment revealed a higher recall proliferative response to MOG(35-55) and a higher frequency of IFN-γ+ and IL-17+ CD4+ cells in DC(IL-27RA-KO) mice than in DC(WT) mice, concomitant with a lower frequency of Foxp3+ Treg cells and IL-10+ CD4+ cells in DC(IL-27RA-KO) mice than in DC(WT) mice (FIGS. 6D-6E). Similar results were obtained when EAE was induced by transferring MOG(35-55)-reactive TH1 or TH17 cells (FIGS. 5F-5H).

Figure 6F:
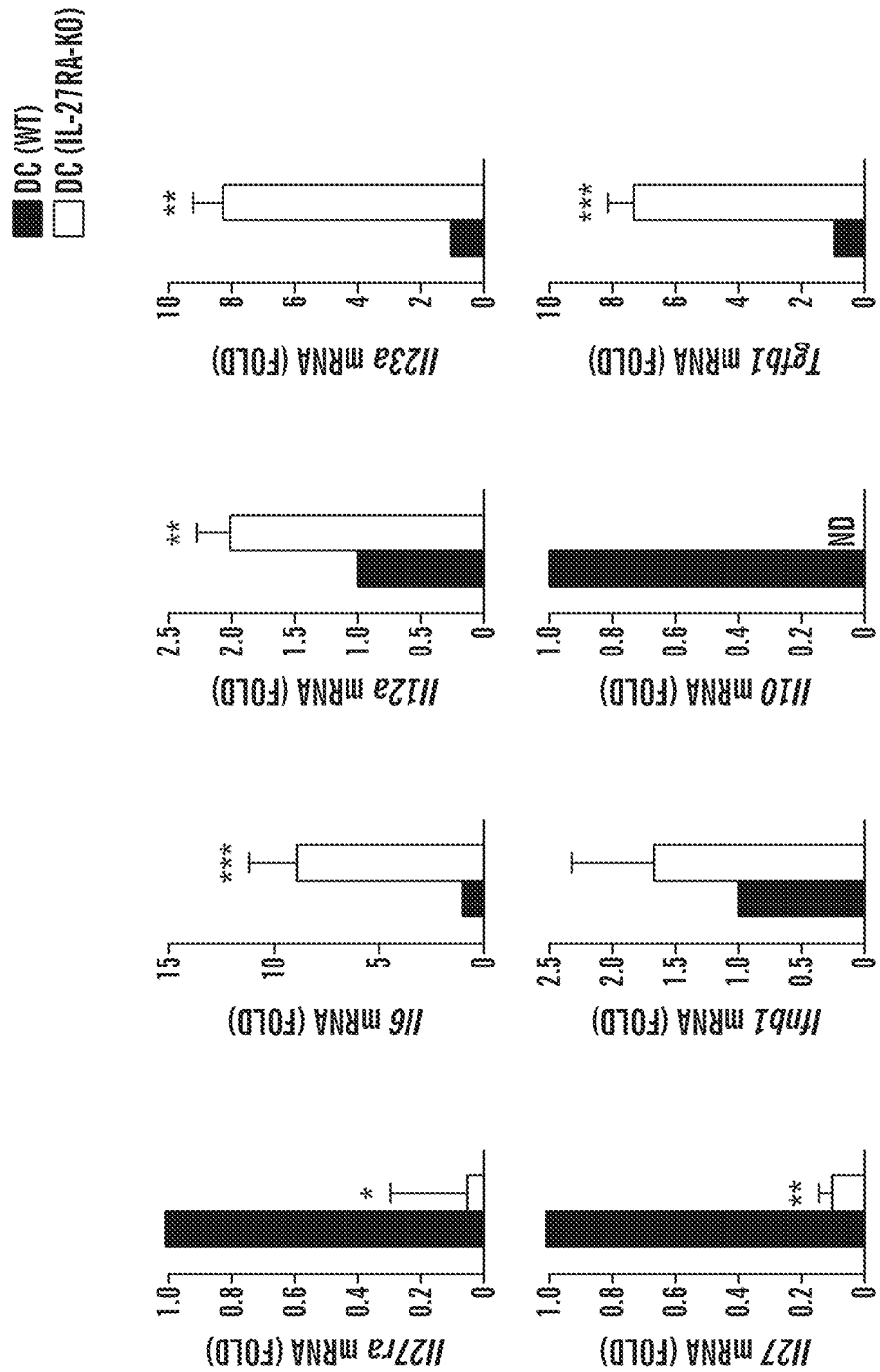
Figure 6G:
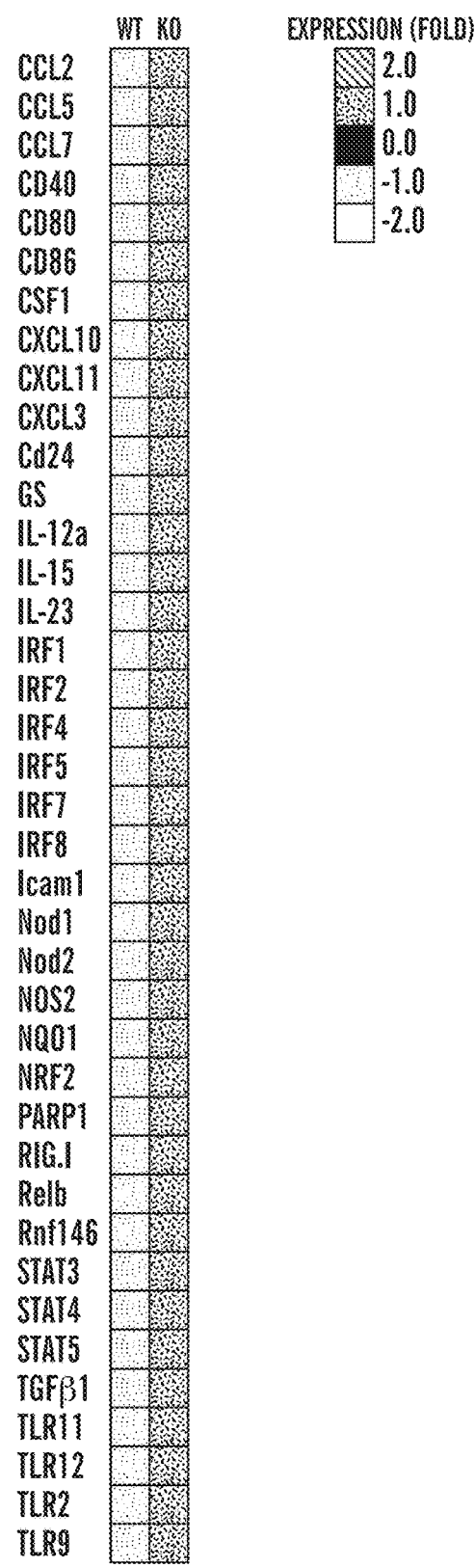
Figure 6H:
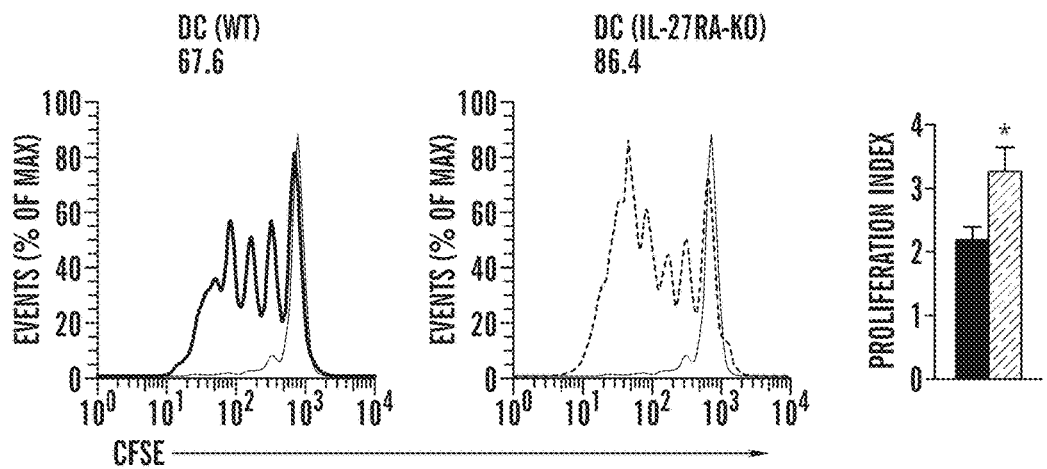
Figure 6I:
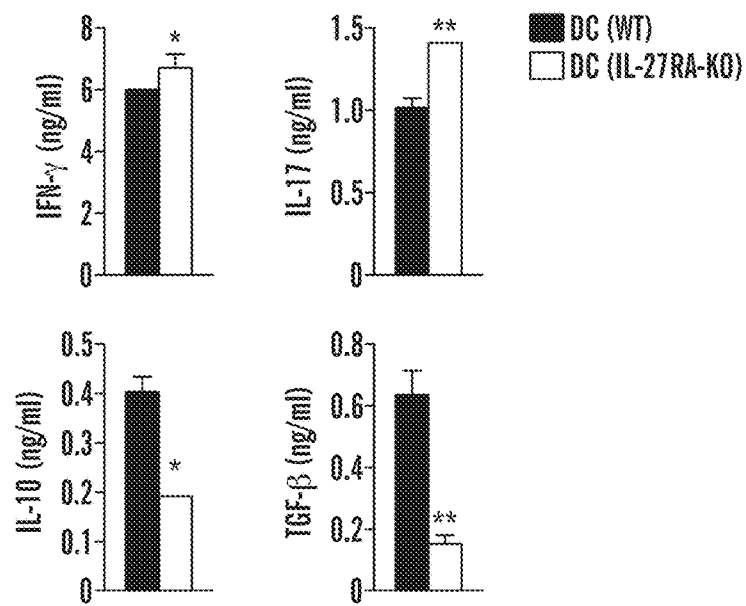

To study the effects of IL-27 signaling in DCs during EAE, cDCs were isolated from DC(WT) and DC(IL-27RA-KO) mice 21 d after EAE induction. cDCs from DC(IL-27RA-KO) mice had higher expression of the proinflammatory cytokines IL-6, IL-12 and IL-23, concomitant with lower expression of IL-10 and IL-27, than that of DC(WT) mice (FIG. 6F). These results were confirmed by additional quantitative profiling analyses, which detected a pronounced proinflammatory transcription profile in cDCs isolated from DC(IL-27RA-KO) mice during EAE (FIG. 6G). Moreover, cDCs from DC(IL-27RA-KO) mice showed an greater ability to activate the proliferation of 2D2 CD4+ T cell and promoted the production of increased amounts of IFN-γ and IL-17 and decreased quantities of IL-10 and TGF-β1 than did their DC(WT) counterparts (FIGS. 6H-6I). Together these data showed that IL-27 acted on cDCs in vivo to limit the development of encephalitogenic T cells and EAE.

Example 4. Transcriptional Effects of IL-27 on DCs

Figure 7A:
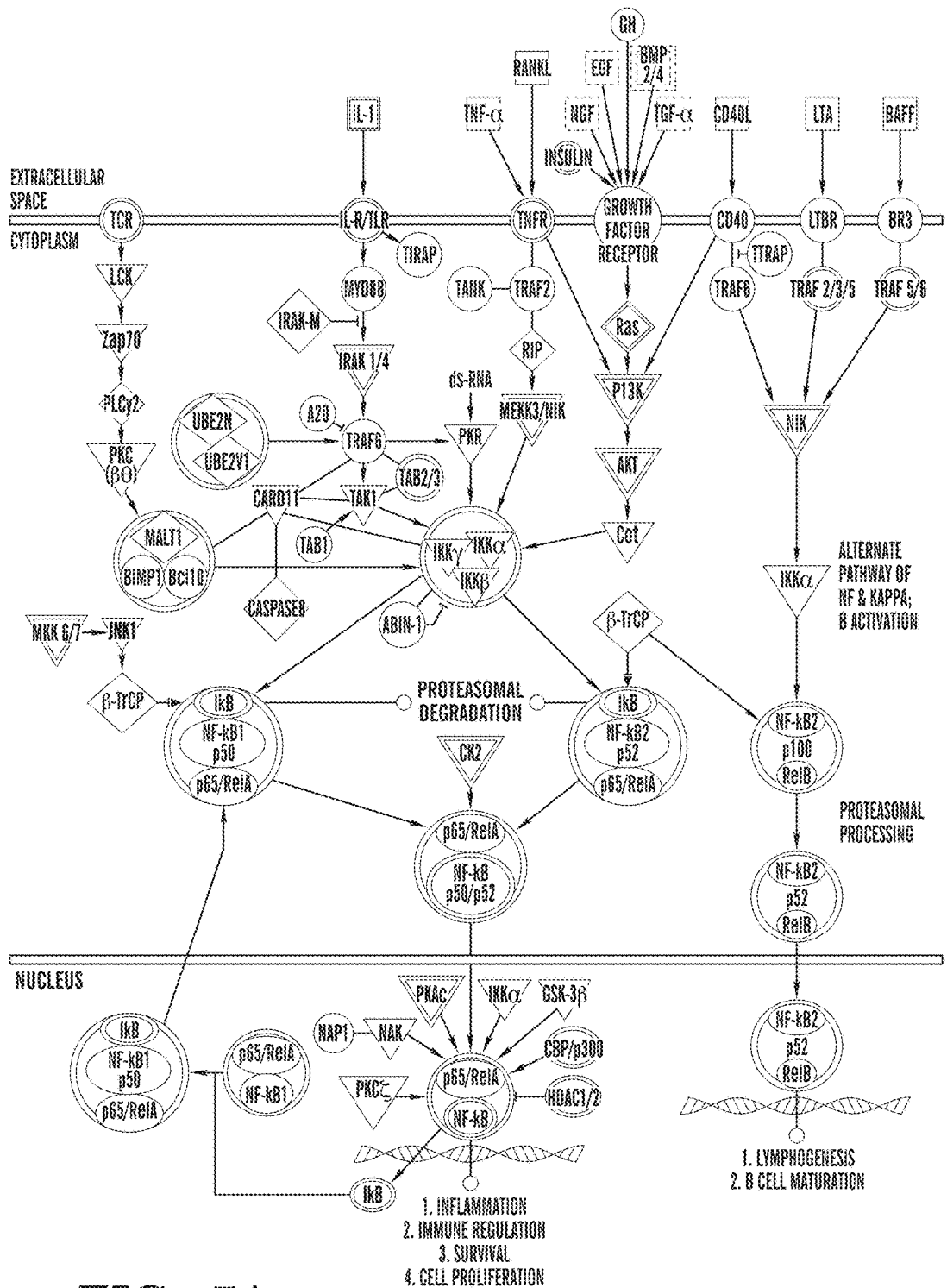
FIGS. 7A-7D show transcriptional effects of IL-27 on cDCs.
Figure 7B:
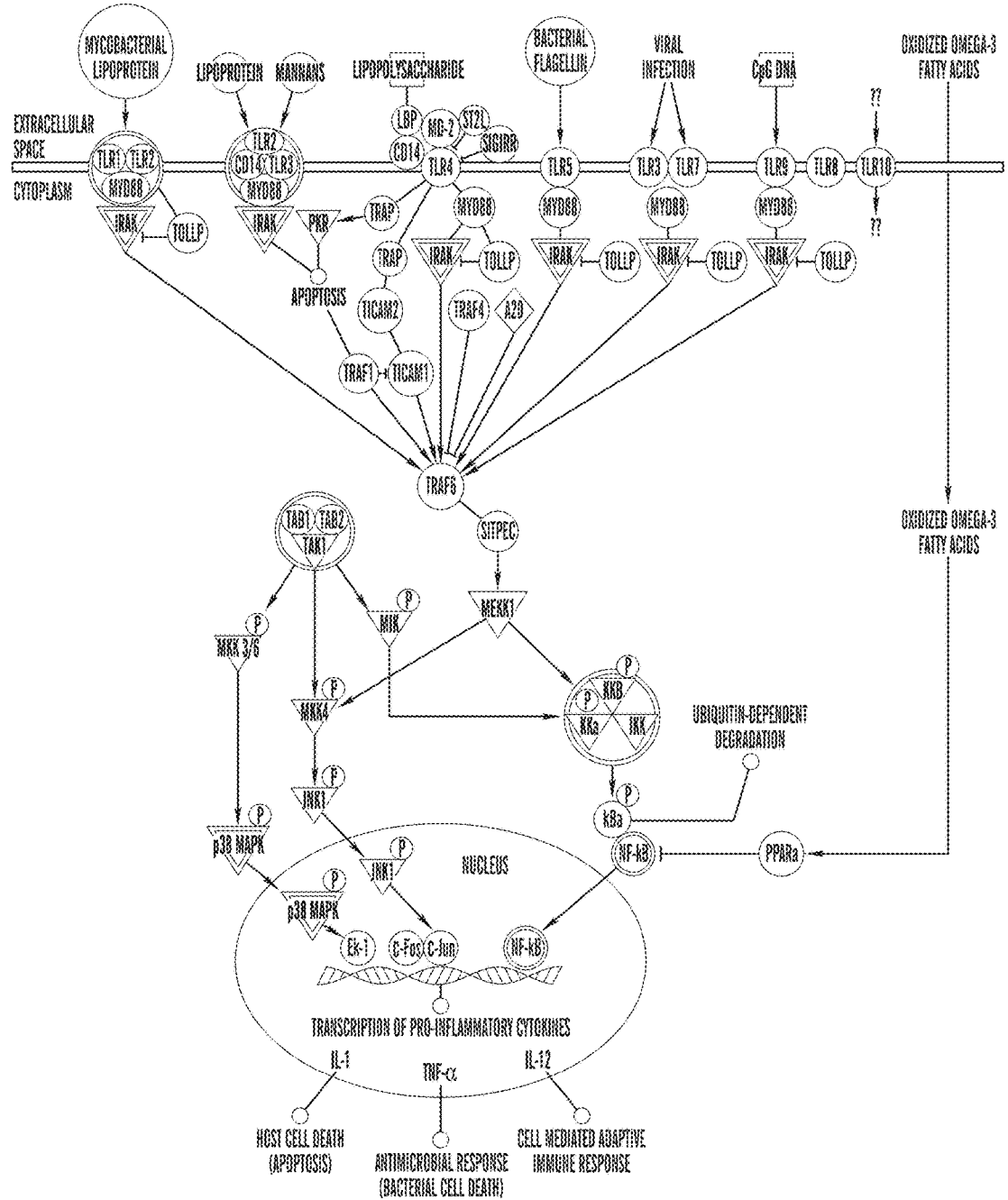
Figure 7C:
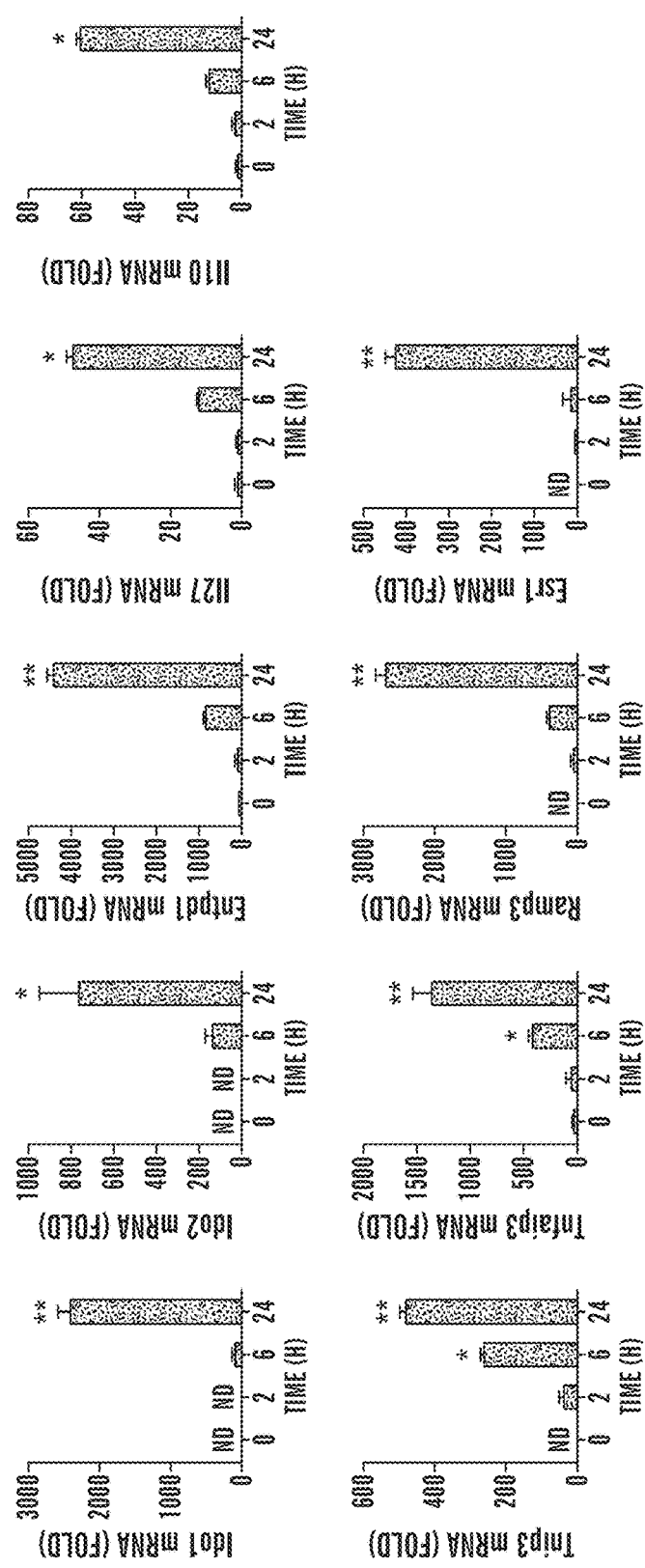

To determine the mechanisms that mediate the effects of IL-27 on DCs, the expression profiles of primary splenic cDCs isolated from naive wild-type mice and treated in vitro with IL-27 were analyzed by microarray. Examination of the expression data by Ingenuity pathway analysis identified significantly lower expression of genes encoding proinflammatory molecules associated with the NF-κB and Toll-like receptor signaling pathways in IL-27-treated cDCs than in untreated cDCs (P=2.16×10$^{-21}$ and P=4.55×10$^{-27}$, respectively; FIGS. 7A-7B). Conversely, treatment with IL-27 led to a significant increase over time in the expression of Tnip3 and Tnfaip3, which encode molecules known to inhibit NF-κB activation23 (FIG. 7C). It was also found that there was significant upregulation over time of Ido1, Ido2, Il27, Il10 and Entpd1, which encode anti-inflammatory molecules (FIG. 7C).

Figure 7D:
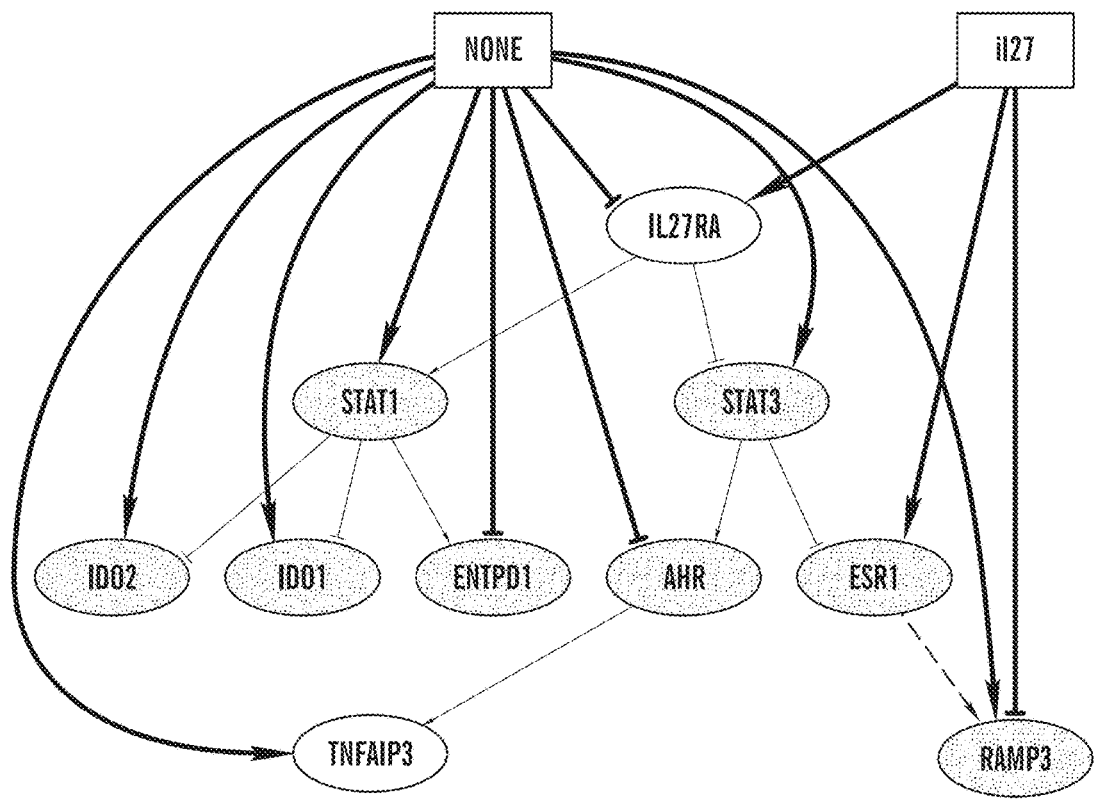

The NetGenerator algorithm was used to analyze the transcriptional response of DCs to IL-27. This algorithm integrates expression profiles in a model with prior 'knowledge' of the genes under investigation and their connections[24]. The resulting model indicated that IL-27 controlled the expression of the anti-inflammatory molecules described above in a manner dependent on the transcription factors STAT1 and STAT3 (FIG. 7D). Together these data showed that IL-27 limited the inflammatory response of cDCs and triggered the expression of tolerogenic molecules.

Example 5. Identification of a Molecule/Ligand that Mediates the Inhibitory Effects of IL-27 on DCs The transcriptional profiling studies identified several candidate molecules that probably mediate the effects of IL-27 signaling in cDCs on the activation of T cells. To identify the mechanisms that mediate the effects of IL-27 on the antigen-presenting function of cDCs, blocking antibodies to IL-27, IL-10, IFN-β or TGF-β, or the indoleamine 2,3-deoxygenase (IDO)-specific inhibitor 1-methyl-dtryptophan (1-D-MT) was used. Splenic cDCs were pre-treated with IL-27 and then treated with ecLPS, extensively washed and used to activate naive CD4+ T cells with antibody to CD3 (anti-CD3) in the presence of the blocking antibodies to cytokines or 1-D-MT. The suppressive effect of pretreating cDCs with IL-27 was not blocked by the antibodies or 1-D-MT (FIGS. 8A-8B), which indicated that neither IDO nor the cytokines IL-27, IL-10, IFN-β or TGF-β mediated the suppressive effects of cDCs pretreated with IL-27.

Expression of PD-L1 (CD274), the ligand for the T cell-inhibitory receptor PD-1, is previously reported to be upregulated following the treatment of mouse pDCs[20] or human monocyte-derived DCs[19] with IL-27. No substantial upregulation of PD-L1 expression was detected after treating cDC with IL-27 (FIG. 9A). Moreover, the suppressive effects of IL-27-treated cDCs on the activation of T cells was also observed when we used PD-L1- or IL-10-deficient cDCs (FIG. 9B). Together these data indicated that the suppressive effects of IL-27 on the antigen-presenting function of cDCs were independent of PD-L1 or IL-10.

CD39 has been previously linked to the suppressive activity of mouse and human Treg cells[25, 26], but not to dendritic cells. Entpd1 (which encodes CD39) was significantly upregulated in DCs in response to treatment with IL-27 in vitro (P=0.01; FIG. 7C). Hence, it was sought to determine the role of CD39 in the effects of IL-27 on cDCs. Entpd1 deficiency abolished the suppressive effects of pretreatment of DCs with IL-27 on the activation and polarization of T cells. Pretreatment of Entpd1-deficient cDCs with IL-27 did not significantly decrease the proliferative response and the production of IFN-γ and IL-17, and had no significant effect on IL-10 production and Foxp3 expression by 2D2 T cells (P=0.2365; FIG. 8C and FIGS. 9B-9C). Thus, these data indicated that CD39 mediated the effects of IL-27 signaling in cDCs on T cell activation.

To further characterize the role of CD39 on the effects of IL-27 in DCs, the regulation of CD39 expression by IL-27 was evaluated. Freshly isolated cDCs from DC(IL-27RA-KO) mice showed significantly lower expression of both Entpd1 mRNA and CD39 protein, reflected as a significant decrease in CD39+ DCs, than did their DC(WT) counterparts (FIG. 8D). Thus, IL-27 controlled Entpd1 expression in cDCs in vitro and in vivo.

Figure 8F:
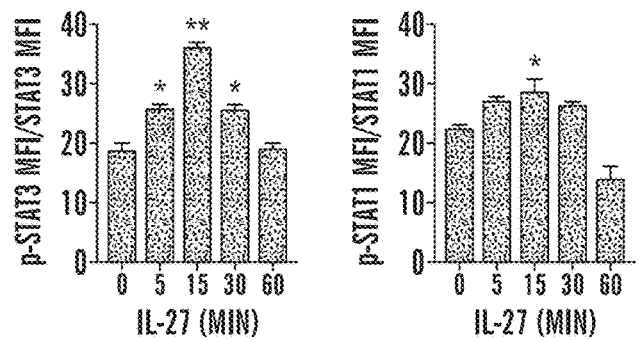
Figure 8G:
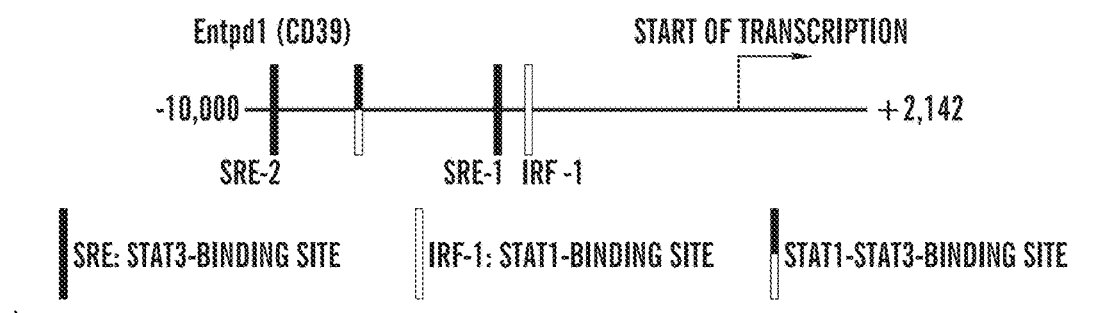

STAT1 and STAT3 mediate the response to IL-27 in T cells[17]. Significant phosphorylation of STAT3 in cDCs 5 min after treatment with IL-27 and a modest but significant increase in the phosphorylation of STAT1 were detected (FIGS. 8E-8F). Bioinformatics analysis identified a putative STAT1-binding element (IRF-1), two STAT3-binding elements (SRE-1 and SRE-2) and a common STAT1-STAT3-binding element upstream of the transcription start site in the Entpd1 promoter (FIG. 8G). Chromatin-immunoprecipitation (ChIP) assays detected binding of STAT3 to SRE-1, SRE-2 and the STAT1-STAT3-binding element in the Entpd1 promoter in response to IL-27 (FIG. 8H). Binding of STAT1 to the Entpd1 promoter, however, was unresponsive to IL-27 and was triggered by activation with ecLPS instead (FIG. 8I).

To determine the functional consequences of the interaction of STAT1 and STAT3 with the Entpd1 promoter, reporter assays were performed. Cotransfection of HEK293 human embryonic kidney cells with a reporter construct containing the gene encoding firefly luciferase under the control of the Entpd1 promoter together with a construct encoding constitutively activated STAT1 or STAT3 led to significantly more in luciferase activity than did transfection of control cells with empty vector, but this effect was significantly stronger in response to constitutively activated STAT3 (FIG. 8J). These data indicated that IL-27 controlled CD39 expression in cDCs via STAT3.

Example 6. CD39 Controls Activation of the NLRP3 Inflammasome

CD39 is an ectonucleotidase that catalyzes the degradation of extracellular ATP and ADP[28]. Extracellular ATP triggers activation of the NLRP3 inflammasome[29], a process shown to control the differentiation of encephalitogenic TH1 and TH17 cells during EAE[30]. As presented herein, CD39 expression is required for the effects of IL-27 signaling in cDCs on the activation and differentiation of T cells (FIG. 8C and FIGS. 9A-9E). The effects of IL-27 on the extracellular concentration of ATP and activation of the NLRP3 inflammasome were thus evaluated. Pretreatment with IL-27 and treatment with ecLPS led to a significant decrease the extracellular concentration of ATP detected after activation of wild-type cDCs with ecLPS (FIG. 10A). However, pretreatment with IL-27 had no effect on the extracellular concentration of ATP measured in the supernatants of IL-27RA- or CD39-deficient cDCs treated with ecLPS (FIG. 10A). Moreover, deficiency in IL-27RA or CD39 in cDCs led to a significantly higher extracellular concentration of ATP detected after activation with LPS than that of their wild-type counterparts (FIG. 10A).

Figure 10D:
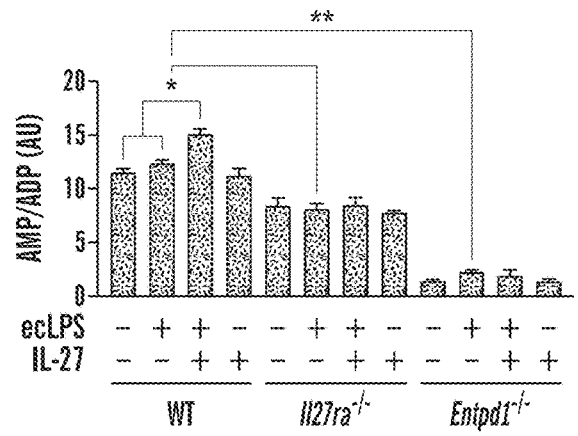

To further explore the mechanisms linked to the reduced amount of extracellular ATP detected in tissue culture supernatants of wild-type cDCs treated with IL-27, exogenous ATP (500 μM) was added to cDCs treated with LPS, vehicle or IL-27 and the residual extracellular ATP in the supernatants after 2 h of incubation was quantified. Significantly lower concentrations of extracellular ATP were found to remain in supernatants of wild-type cDCs treated with ecLPS and IL-27 than in those of wild-type cDCs treated with ecLPS (FIG. 10B). However, IL-27 did not affect the amount of residual extracellular ATP in IL-27RA- or CD39-deficient cells (FIG. 10B), which indicated that the lower abundance of ATP in supernatants of wildtype cDCs treated with IL-27 resulted from its increased catabolism by CD39. Further, treatment with IL-27 significantly increased nucleoside triphosphate diphosphohydrolase activity in wild-type cDCs but not in IL-27RA- or CD39-deficient cDCs (FIGS. 10C-10D). Moreover, less nucleoside triphosphate diphosphohydrolase activity (manifested as greater residual amounts of ATP) was detected in IL-27RA-deficient DCs than in wild-type cDCs (FIGS. 10C-10D), which indicated that the autocrine effects of IL-27 controlled the ability of cDCs to degrade extracellular ATP.

Figure 10E:
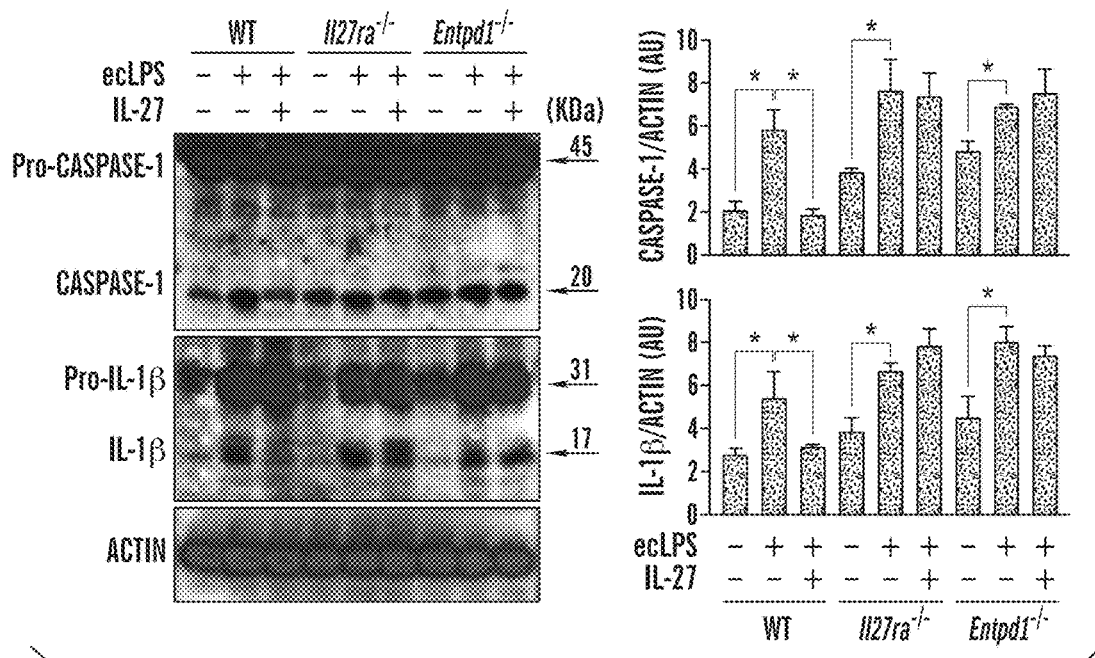
Figure 10F:
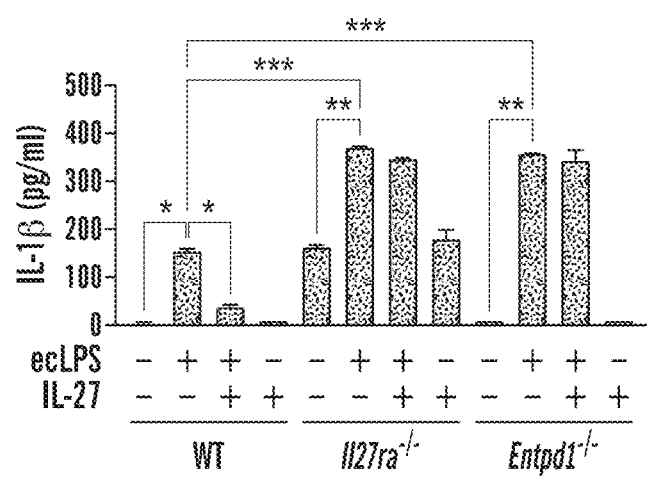

ATP activates the NLRP3 inflammasome in certain APCs such as macrophages[29]. Activation of the NLRP3 inflammasome results in the generation of active caspase 1, which leads to the maturation and release of IL-18 and IL-1β[31]. It was found that pretreatment with IL-27 significantly suppressed activation of the NLRP3 inflammasome in wild-type cDCs activated with ecLPS, as shown by a lower abundance of activated caspase-1 and mature IL-1β (FIG. 10E) and the secretion of significantly lower amounts of IL-1β into the culture medium (FIG. 10F). In accordance with the findings presented herein on the extracellular concentrations of ATP, no inhibitory effects of IL-27 on the activation of the NLRP3 inflammasome and the release of IL-1β in ecLPS-treated IL-27RA- or CD39-deficient cDCs were detected (FIGS. 10E-10F). Indeed, deficiency in IL-27RA or CD39 resulted in significantly more release of IL-1β than that of wild-type cDCs after treatment with ecLPS (FIG. 10F). Together these data suggested that without wishing to be bound by theory, the upregulation of CD39 expression triggered by IL-27 limited extracellular ATP concentrations and, consequently, activation of the NLRP3 inflammasome in cDCs.

Example 7. Effect of CD39 in DCs on EAE Development

Figure 9D:
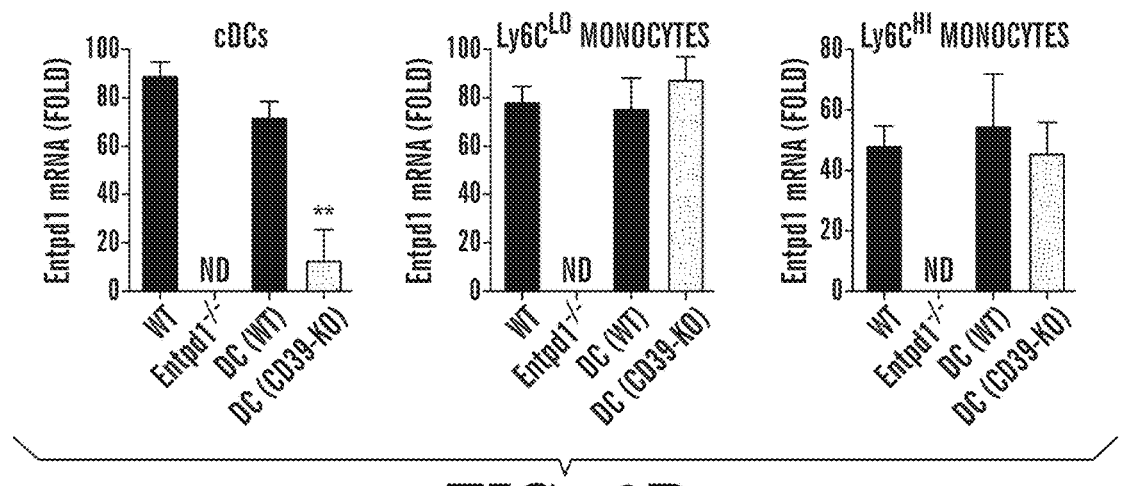
Figure 9E:
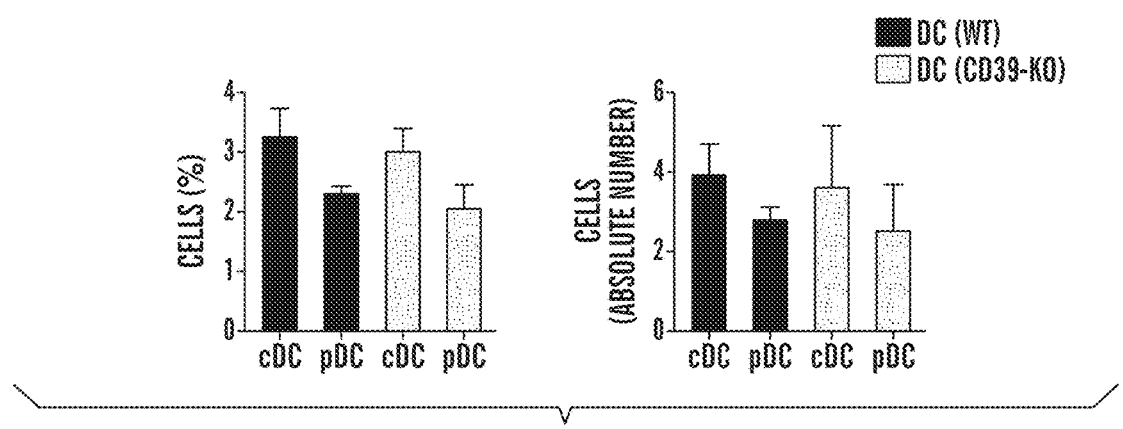
Figure 11A:
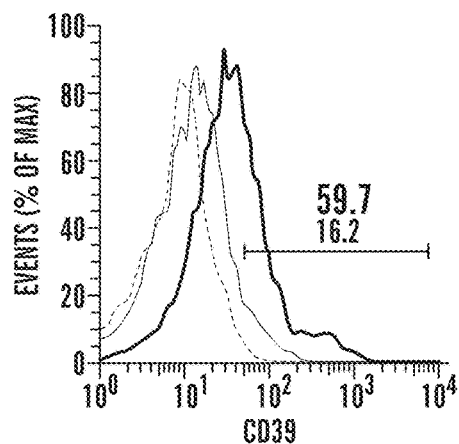
FIGS. 11A-11H show that CD39 in DCs controls T cell differentiation and EAE development.
Figure 11B:
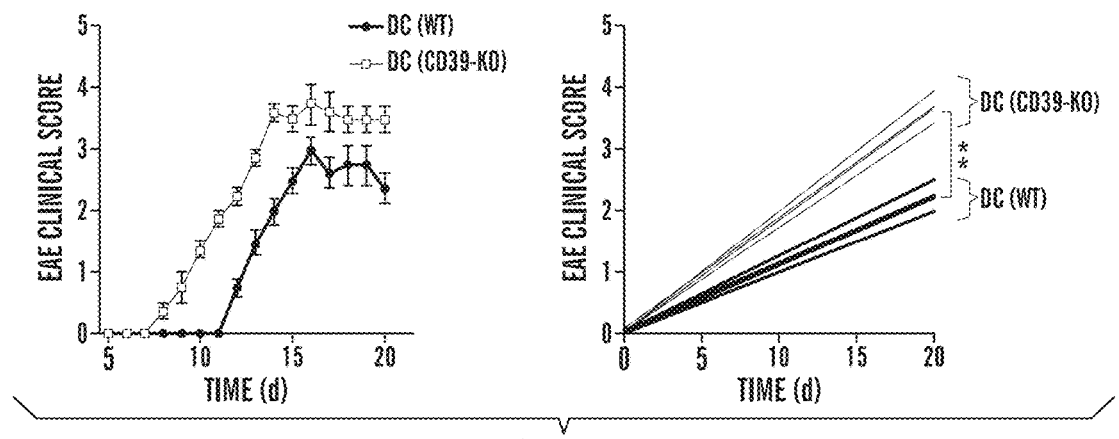
Figure 11C:
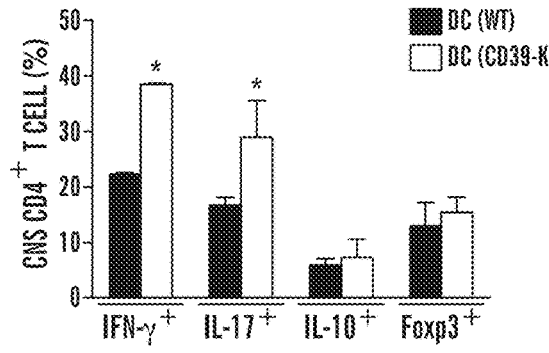
Figure 11D:
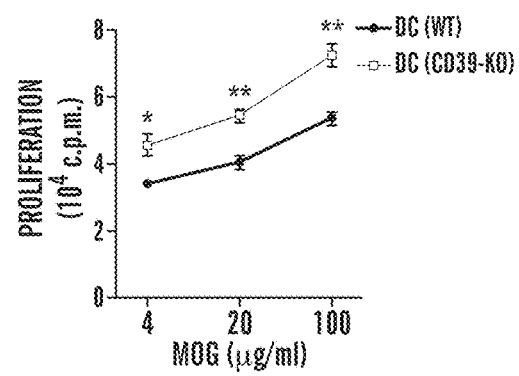
Figure 11E:
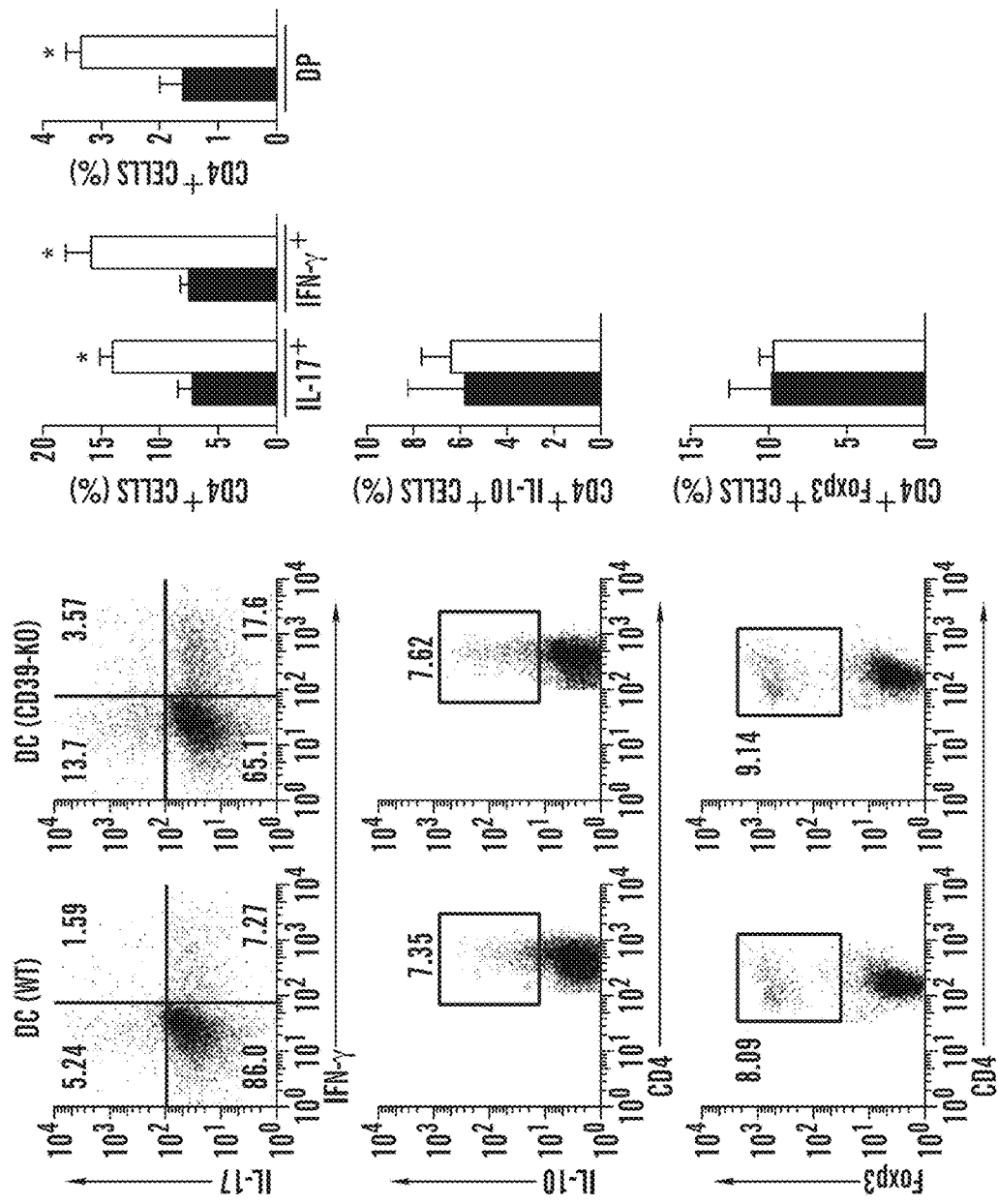

To determine the role of CD39 in DCs during EAE, CD11c-DTR→WT chimeras were reconstituted with CD39-deficient DC precursors to generate mice lacking Entpd1 expression in DCs (DC(CD39-KO) mice). DC(WT) mice were used as controls. Significantly lower expression of CD39 protein was found in cDCs from DC(CD39-KO) mice than in cDCs from DC(WT) mice (FIG. 11A), but this result was not obtained for other APC populations (FIG. 9D). No difference was detected between DC(WT) and DC(CD39-KO) mice in the frequency or absolute number of DCs (FIG. 9E). The induction of EAE led to an earlier onset of EAE in DC(CD39-KO) mice than in DC(WT) mice, and the EAE also reached significantly higher scores in the former (FIG. 11B). The worsening of EAE in DC(CD39-KO) mice was correlated with an increased frequency of TH1 and TH17 cells in the CNS (FIG. 11C). In agreement with the worsening of EAE associated with CD39 deficiency in DCs as shown herein, DC(CD39-KO) splenic T cells had significantly enhanced proliferative recall response to MOG(35-55), and DC(CD39-KO) mice had a significantly greater frequency of CD4$^+$ CD44$^+$ CD40L$^{hi}$ splenic IFN-γ+ and IL-17+ CD4+ T cells (FIGS. 11D-11E). No difference was observed between DC(WT) and DC(CD39-KO) mice in the frequency of Foxp3+ Treg cells or IL-10+ CD4+ T cells (FIGS. 11D-11E).

Figure 11F:
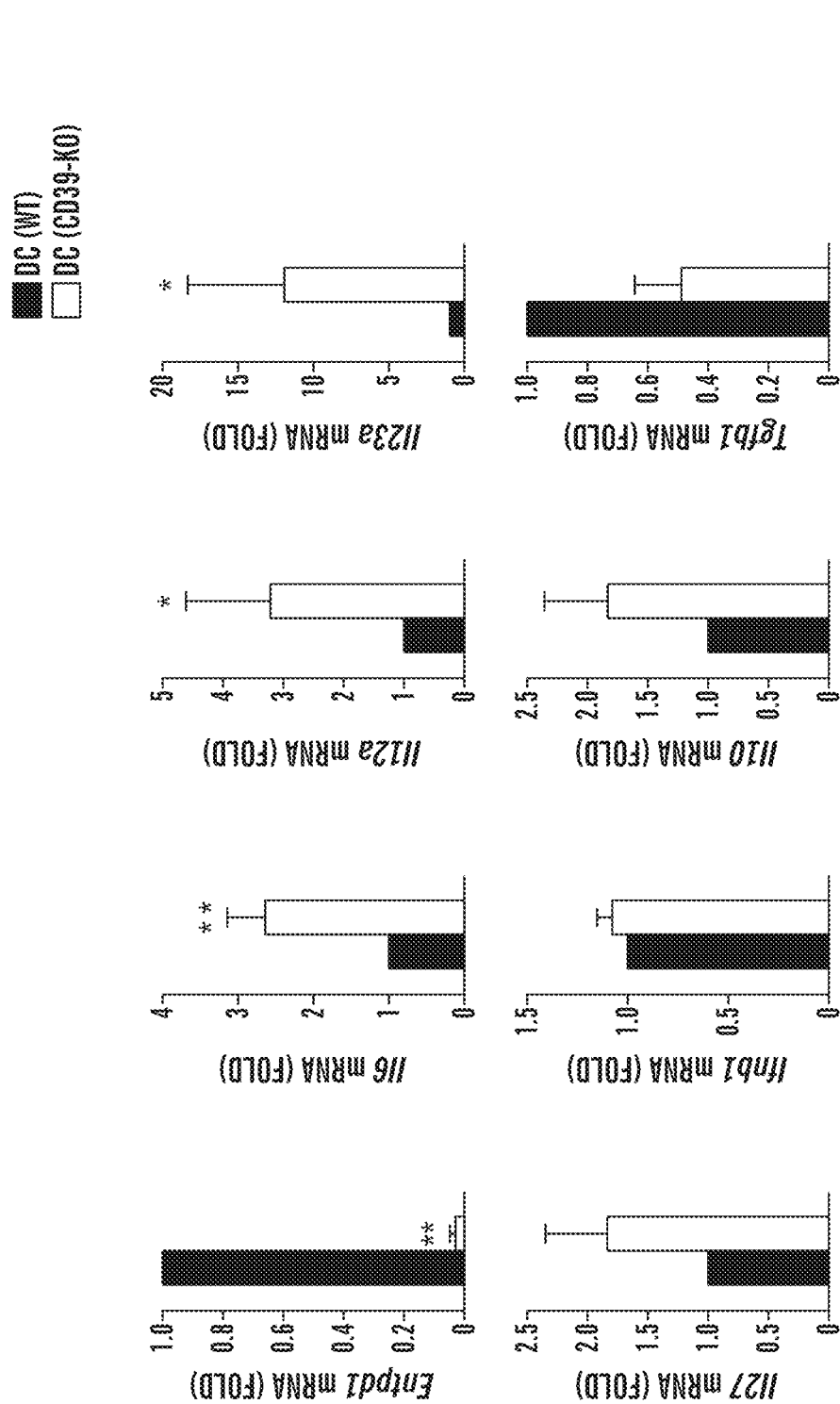
Figure 11G:
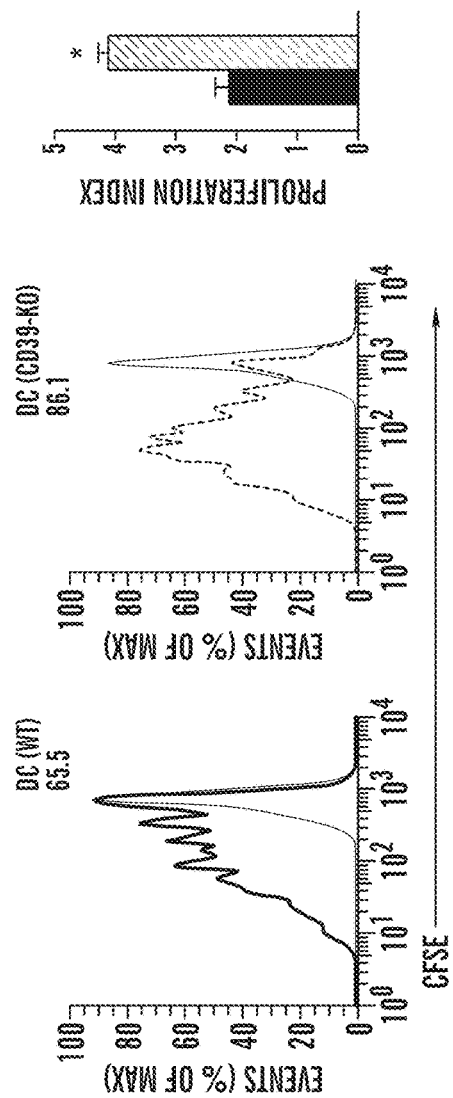
Figure 11H:
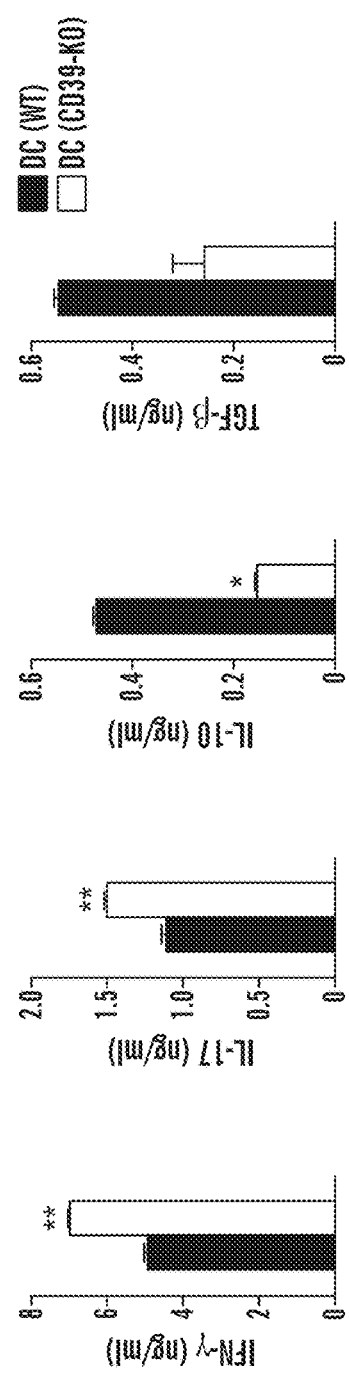

Analysis of cDCs isolated 21 d after the induction of EAE showed significantly lower CD39 expression, concomitant with higher expression of mRNA encoding the proinflammatory cytokines IL-6, IL-12 and IL-23, in DC(CD39-KO) mice than in DC(WT) cells (FIG. 11F). No significant difference was found between DC(WT) and DC(CD39-KO) mice in the expression of mRNA encoding IL-10, TGF-β, IFN-β or IL-27 (FIG. 11F). In vitro, cDCs from DC(CD39-KO) mice showed an increased ability to trigger the proliferation of naive 2D2 CD4+ T cells in the presence of MOG(35-55) and induce the production of IL-17 and IFN-γ, at the expense of decreased secretion of IL-10 and TGF-β (FIGS. 11G-11H). Thus, expression of CD39 in DCs limited the encephalitogenic TH1 and TH17 T cell response and the development of EAE.

Example 8. Vaccination with IL-27-Conditioned DCs Suppresses Autoimmune Diseases The tolerogenic effects of IL-27 signaling in T cells and DCs provide therapeutic potential in disorders mediated by the immune system. However, IL-27 is previously reported to act on T cells, but not dendritic cells, to boost cytotoxic CD8+ T cell responses[11], which suggests that direct administration of IL-27 could potentially have detrimental side effects in immunologically mediated disorders. Vaccination with DCs can induce immunity to tumors and pathogens[32], but vaccination with naturally-occurring tolerogenic DCs has been shown to induce antigen-specific tolerance[33]. Thus, as shown herein the tolerogenic effects of IL-27 signaling in DCs, and to avoid the potential pathogenic effects of IL-27 administration, it was next sought to determine the therapeutic effects of vaccination with IL-27-conditioned DCs on CNS autoimmunity.

Figure 12A:
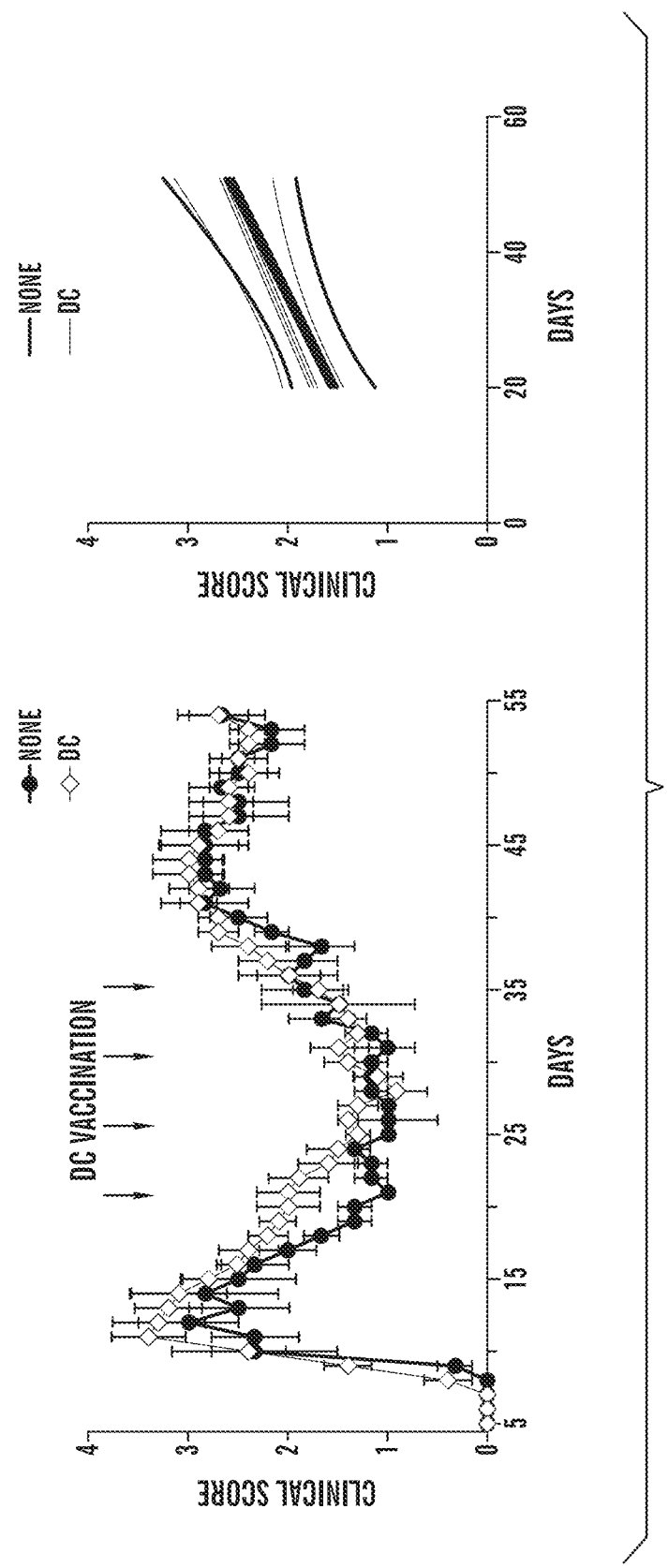
FIGS. 12A-12F show that vaccination with IL-27 conditioned DCs suppresses EAE. EAE was induced by immunization of naive SJL mice with PLP (131-159), and DCs were administered i.v. 4 times, once every 4 days, starting at day 20.
Figure 12B:
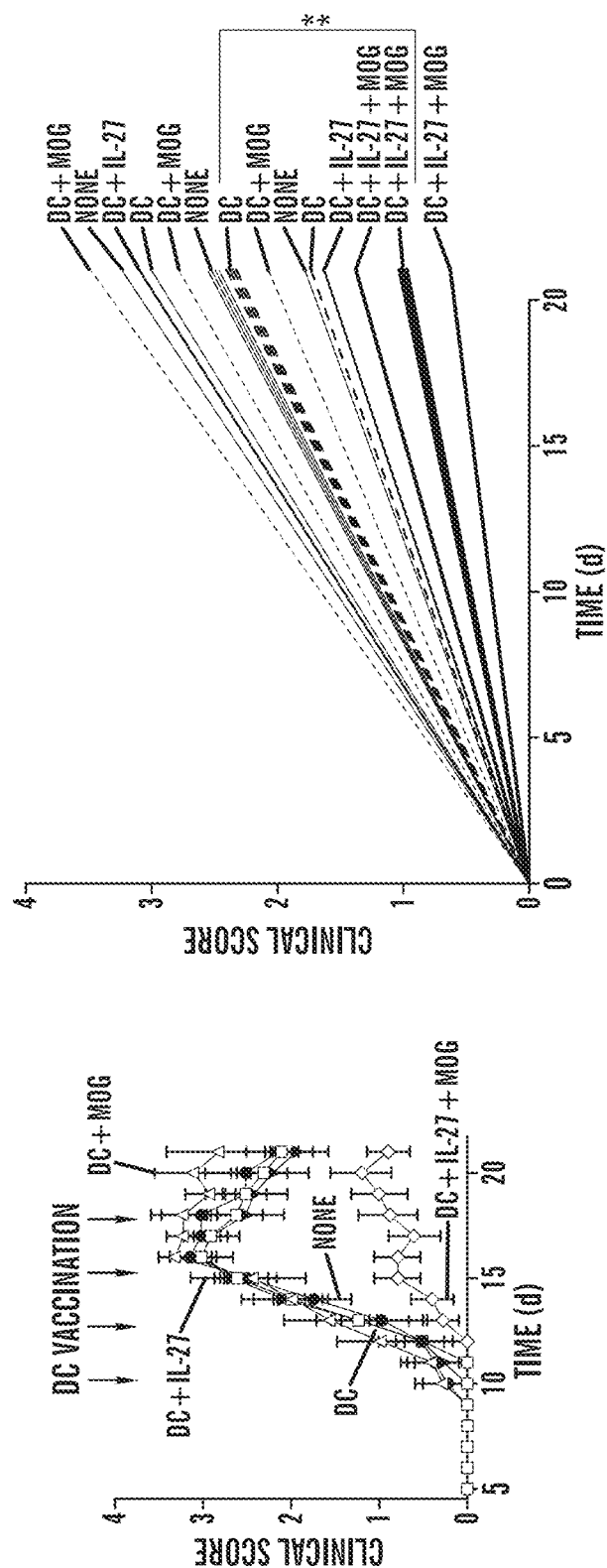
Figure 12C:
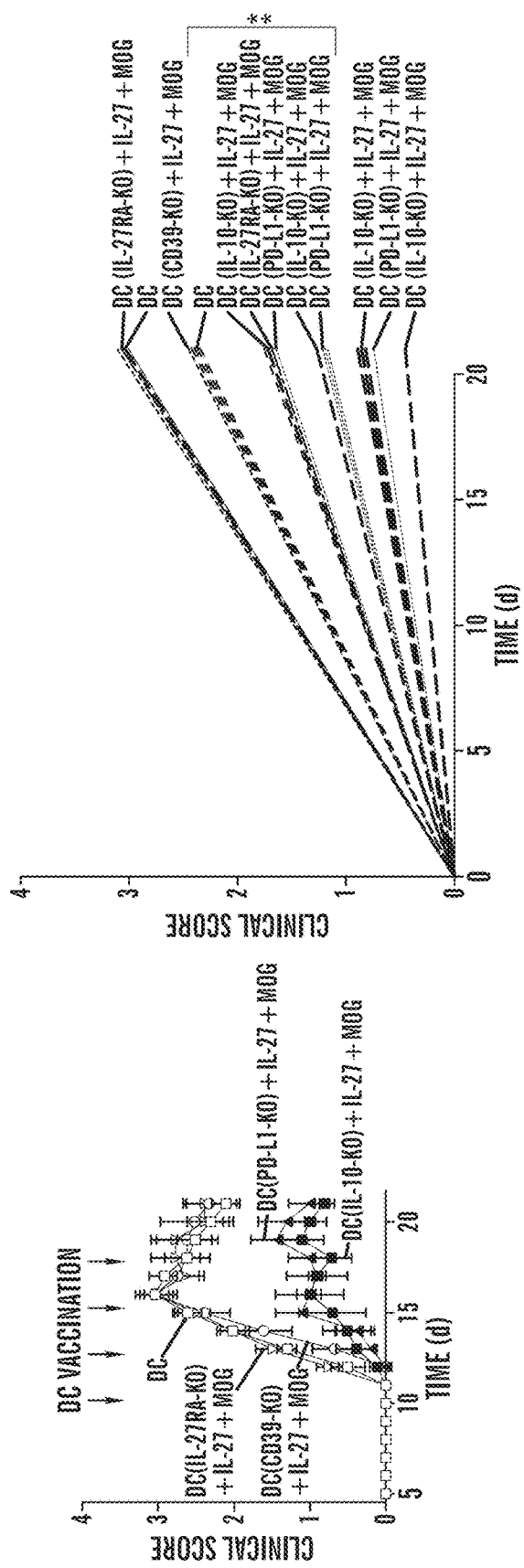
Figures 12D, 12E:
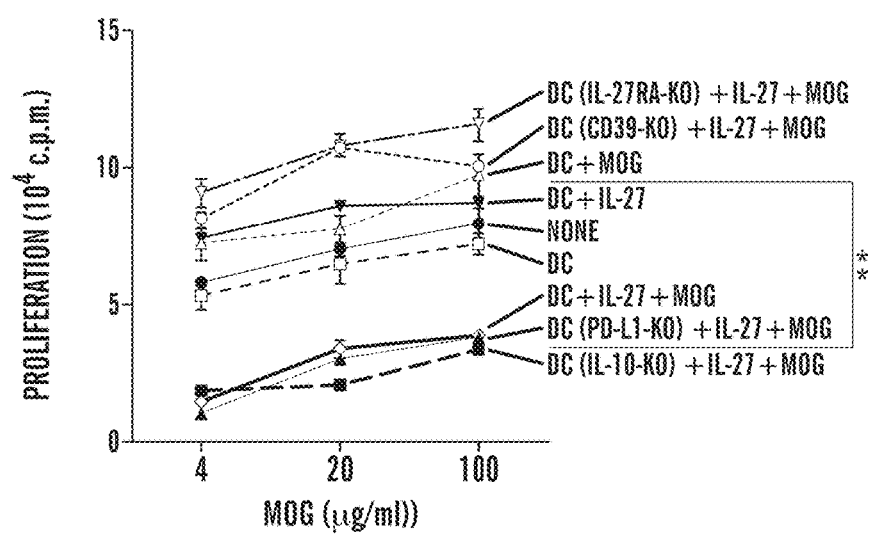
Figure 12F:
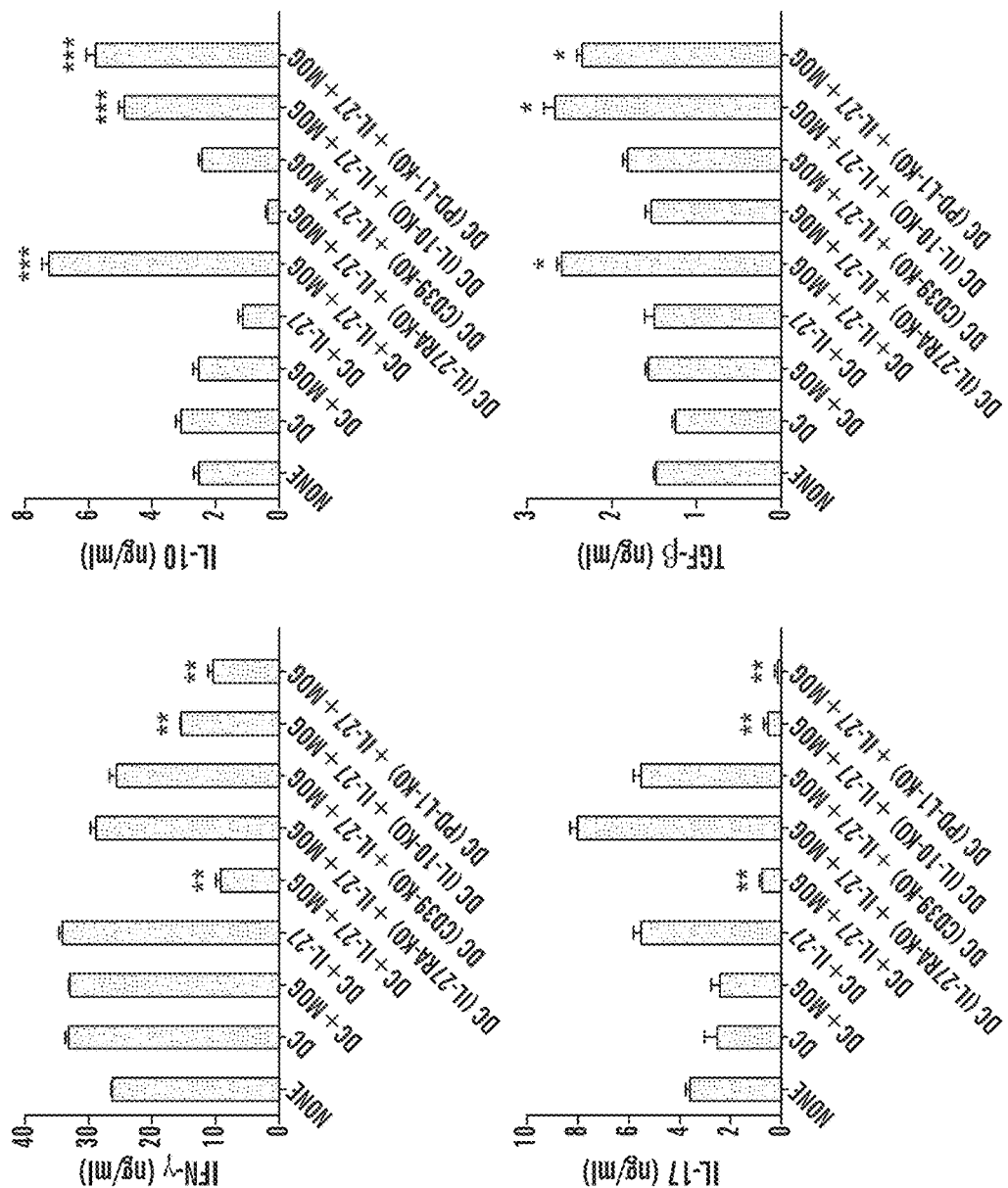
Figure 13A:
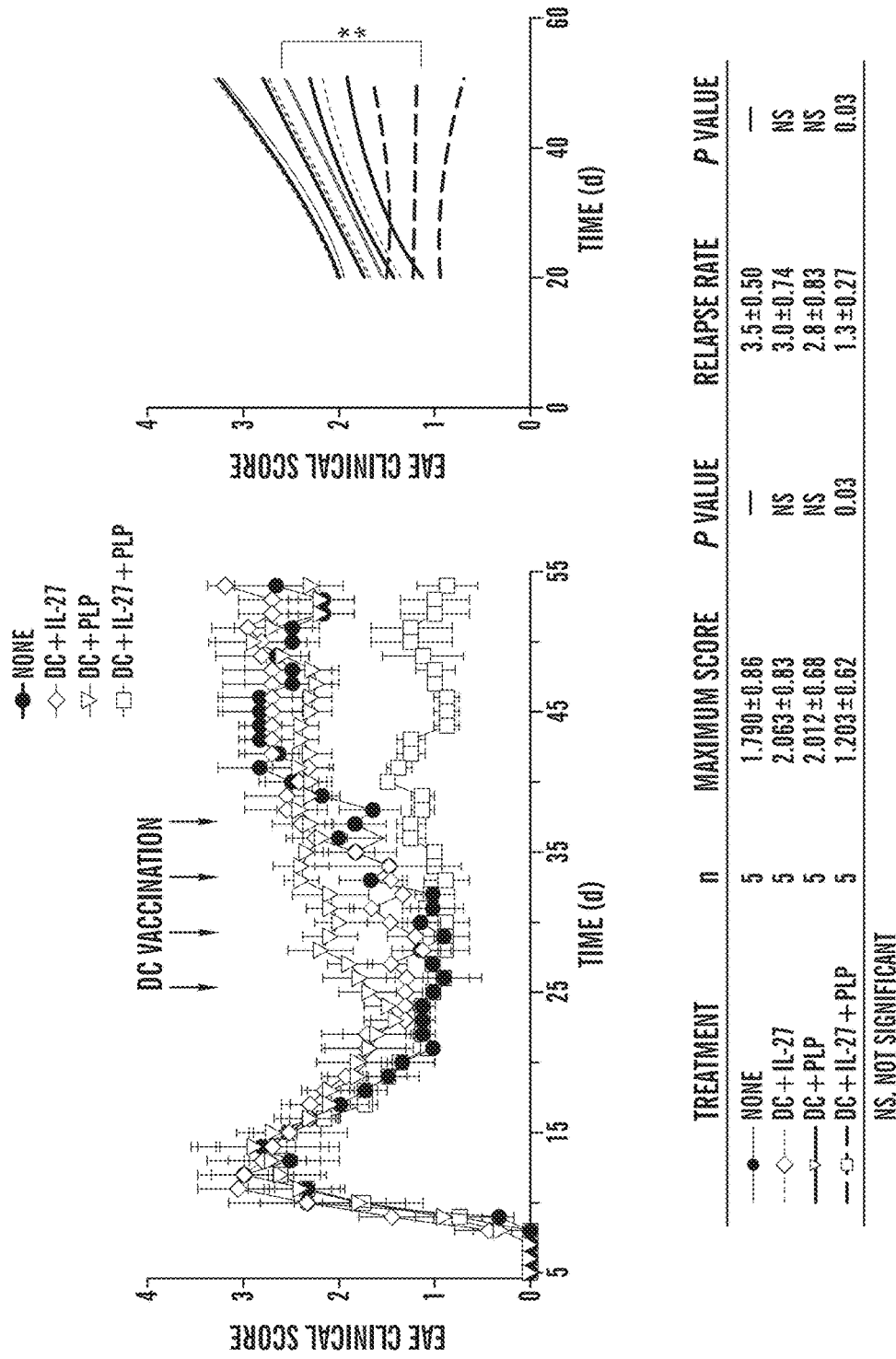
FIGS. 13A-13F show that vaccination with IL-27-conditioned DCs suppresses EAE.
Figure 13B:
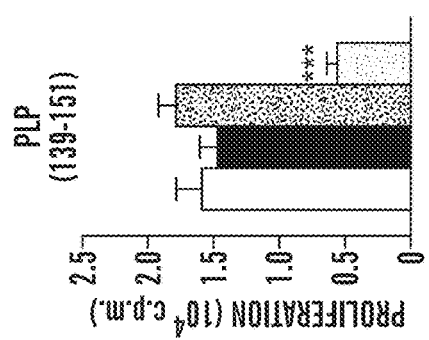
Figure 13C:
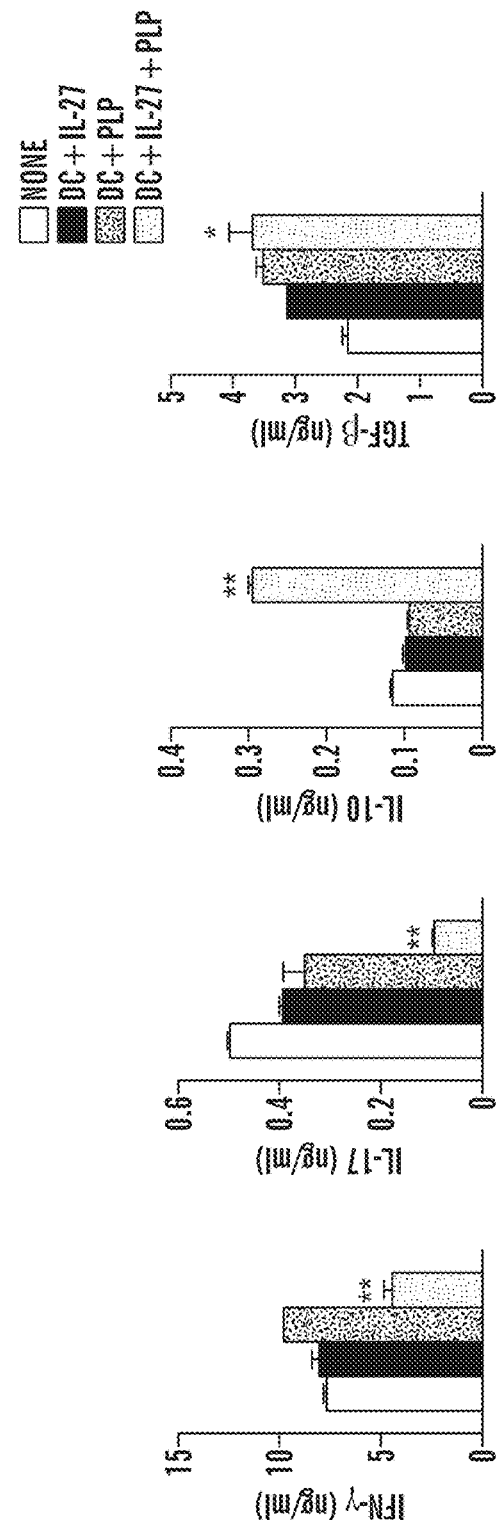

The effects of vaccination with IL-27-conditioned bone marrow-derived DCs on the model of relapsing-remitting EAE induced in SJL mice was assessed by immunization with a peptide of amino acids 139-151 of proteolipid protein (PLP(139-151)). On day 20 after EAE induction, during the remission phase of the disease, the mice were randomly allocated into four groups and treated as follows: group 1, saline only; group 2, DCs loaded with PLP(139-151); group 3, DCs treated with IL-27; group 4, DCs treated with IL-27 and loaded with PLP(139-151). An additional control group received DCs not loaded with peptide or pretreated with cytokine. The treatment was repeated three additional times, once every 4 d. DCs not loaded with peptide or pretreated with cytokine had no significant effect on disease development (P=0.1487; FIG. 12A). However, the administration of IL-27-conditioned DCs loaded with PLP(139-151) led to a significant reduction in EAE and a significant reduction in the proliferative recall response (measured as the production of IFN-γ and IL-17) to PLP(139-151), concomitant with increased production of IL-10 and TGF-β, relative to results obtained for untreated mice (FIGS. 13A-13C).

Figure 13D:
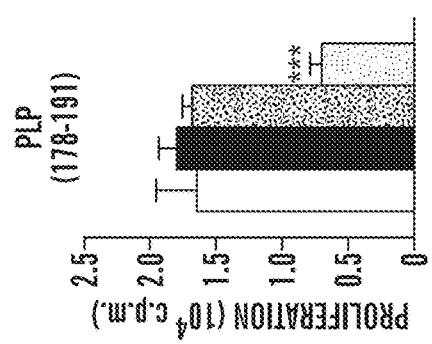
Figure 13E:
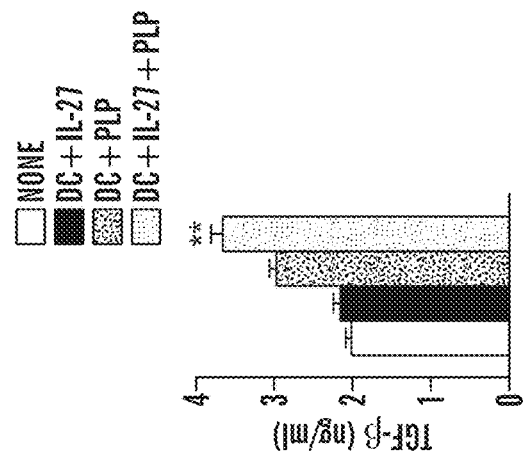
Figure 13E:
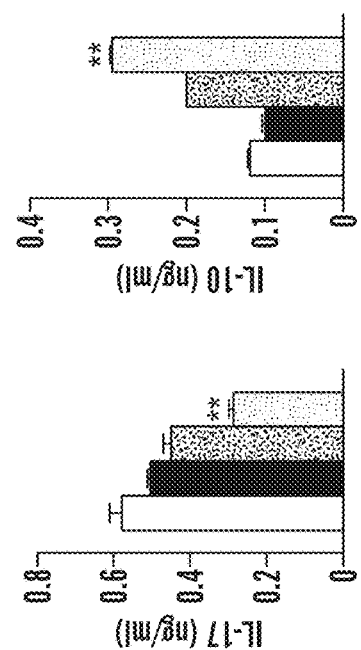
Figure 13E:
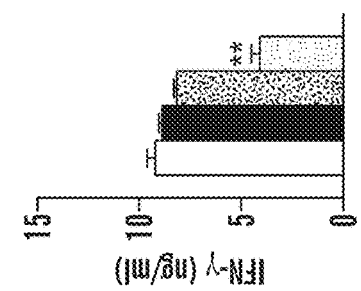

In this model, the chronic phase of EAE is characterized by spreading of the T cell response to the PLP epitope of amino acids 178-191 (PLP(178-191))[7]. Thus, the recall response to PLP(178-191) in DC-vaccinated mice was analyzed. The administration of IL-27-treated DCs loaded with PLP(139-151) led to significant suppression of the proliferative response and production of IFN-γ and IL-17 triggered by PLP(178-191), concomitant with increased production of IL-10 and TGF-β, relative to the results obtained for untreated mice (FIGS. 13D-13E). Thus, vaccination with IL-27-treated cDCs can also reduce epitope spreading in this model of EAE.

Figure 13F:
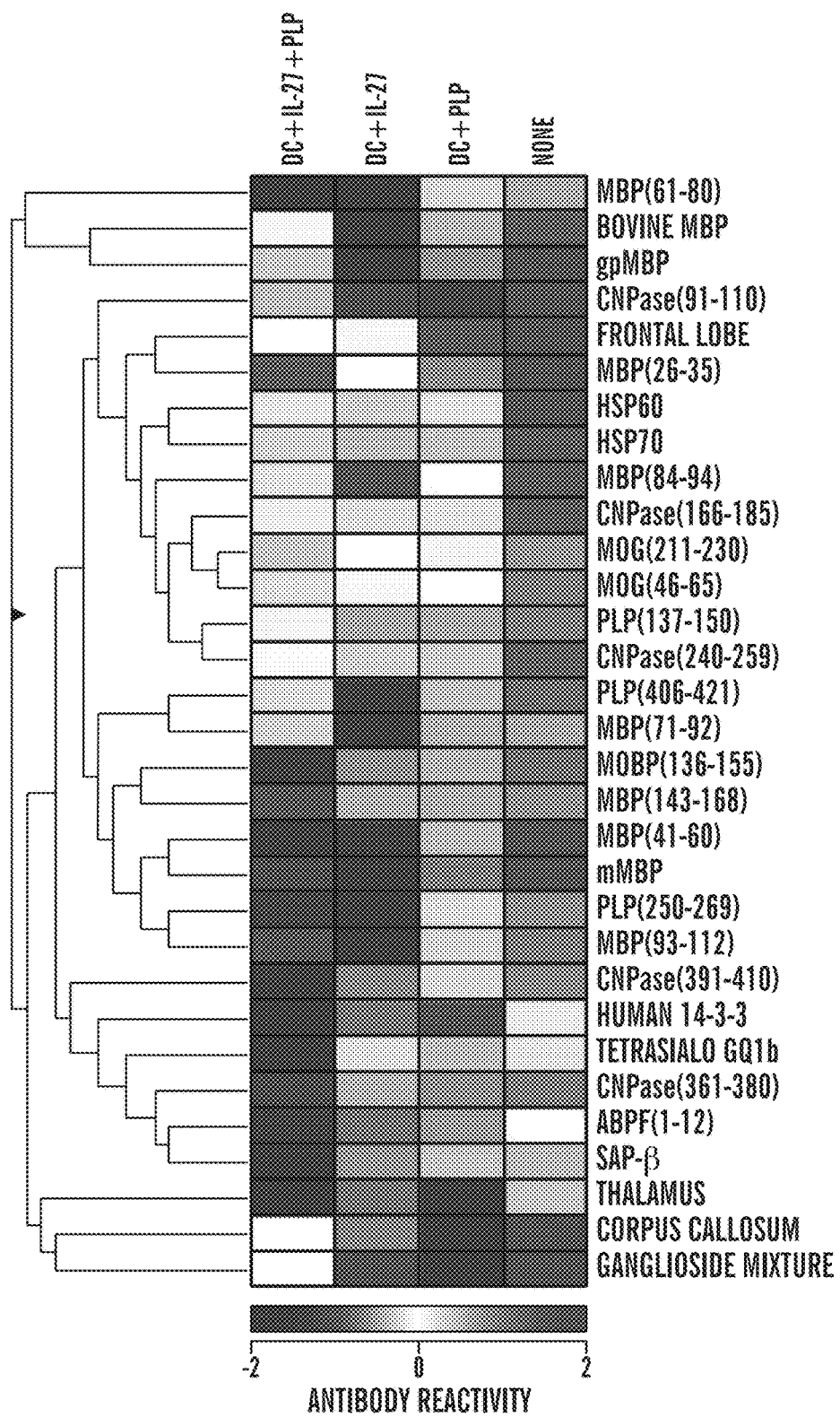

To further investigate the effects of IL-27-conditioned DCs on the immune response, myelin antigen arrays were used, which can detect epitope spreading in EAE and MS[34,35]. The microarrays consisted of a collection of CNS-related autoantigens, including tissue lysates, recombinant proteins, and peptide libraries spanning the entire sequence of myelin proteins and lipids found in the central and peripheral nervous system[34]. The therapeutic effect of vaccination with DCs on EAE in SJL mice was accompanied by a lower serum concentration of immunoglobulin G antibodies to 31 myelin antigens than that in untreated mice (FIG. 13F).

It was then sought to assess the mechanisms involved in the suppression of EAE with IL-27-conditioned DCs; for this the C57BL/6 mouse model of EAE induced with MOG(35-55) was used. The administration of IL-27-conditioned DCs was initiated 10 d after the induction of EAE. Vaccination with IL-27-conditioned wild-type DCs loaded with MOG(35-55) led to significantly diminished EAE relative to that of untreated mice (FIGS. 12B-12F). Similar suppression of EAE was observed after the administration of MOG(35-55)-loaded, IL-27-conditioned DCs deficient in IL-10 or PD-L1 (FIGS. 12B-12F), which indicated that these molecules did not appear to have a role in regulating the encephalitogenic response by IL-27 signaling in DCs. Conversely, MOG(35-55)-loaded, IL-27-conditioned DCs deficient in IL-7RA or CD39 did not have a significant effect on EAE (P=0.7979, P=05708 and P=0.5630, respectively; FIGS. 12B-12F). Together these data showed that vaccination with IL-27-treated DCs controlled the encephalitogenic response and established relapsing-remitting EAE in a therapeutic paradigm in an CD39-dependent manner.

Discussion for Examples 1-8

IL-27 is previously reported to limit tissue inflammation and autoimmunity in various scenarios[11]. Deficiency in the receptor for IL-27 has been previously reported to be linked to the development of exacerbated inflammation in animal experimental models, and polymorphisms in IL-27 have been previously reported to be associated with human inflammatory disorders[11]. However, in those previous reports, the immunoregulatory actions of IL-27 are usually attributed to its direct effects on T cells, whereby it arrests the development of TH17 cells and promotes the differentiation of Tr1 cells through mechanisms that involve the transcription factor AhR[26,36]. Thus, those previous reports did not teach or suggest the immunosuppressive effects of IL-27 on DCs. The present findings identified an important role for IL-27 signaling in DCs in the control of the T cell response and CNS autoimmunity.

Presented herein shows that without wishing to be bound by theory, CD39 was required for modulating the antigen presenting function of cDCs by IL-27 in vitro and in vivo. However, IL-27 also upregulated the expression of additional immunoregulatory molecules, such as IL-27 itself, IFN-β, TGF-β and IDO. Although those molecules did not have a substantial role under the experimental conditions shown herein, they might contribute to the suppressive effects of IL-27 on DCs in alternative manners.

IL-10, known to activate STAT3 signaling, has also been shown to induce a tolerogenic phenotype in DCs[37]. Conversely, STAT3 deficiency restricted to DCs results in the spontaneous development of inflammation[38]. Moreover, microglia and tissue macrophages express CD39, and their function is also regulated by cytokines that activate STAT3 signaling[39,40]. Thus, it is contemplated that the induction of CD39 expression can constitute a common immunoregulatory mechanism triggered by STAT3-activating cytokines in cells of the innate immune system.

Without wishing to be bound by theory, CD39 mediates the suppressive activity of mouse and human Treg cells, probably through the generation of adenosine[25,26]. The mechanisms by which CD39 in APCs regulates adaptive immunity are less clear. Extracellular ATP triggers such activation[28]. Augmented contact hypersensitivity was previously observed in Entpd1-deficient mice[41]. Conversely, Nlrp3 deficiency is previously reported to result in decreased contact hypersensitivity[42]. Follow-up studies have determined that activation of the NLRP3 inflammasome in APCs controls TH1, TH2 and TH17 responses[43,44]. Activation of NLRP3 inflammasome is previously reported to be required for the differentiation of encephalitogenic TH1 and TH17 cells and the development of EAE[30], probably as a result of its effects on the secretion of IL-1β and IL-18.

The present findings presented herein showed that the induction of CD39 expression in DCs by IL-27 led to a significant reduction in the extracellular concentration of ATP, concomitant with a significant reduction in activation of the NLRP3 inflammasome and reduced differentiation of TH1 and TH17 cells. These findings are compatible with a model in which, through the upregulation of CD39 expression, IL-27 limits ATP-dependent activation of the NLRP3 inflammasome in DCs and their ability to promote the differentiation of pathogenic TH1 and TH17 cells. Without wishing to be bound by theory, however, in addition to its effects on CD39 expression, IL-27-triggered signaling can directly interfere with the expression of components of the NLRP3 inflammasome and their activation in DCs.

The immunoregulatory properties of IL-27 can be used for the treatment of human autoimmune diseases. However, IL-27 can boost cytotoxic CD8+ T-cell responses[11], which suggests that the administration of IL-27 could potentially worsen disorders mediated by the immune system. Hence, to evaluate the therapeutic potential of IL-27 and avoid its potential deleterious side effects, the effects of vaccination with IL-27-conditioned DCs were assessed. Presented herein shows that vaccination with IL-27-conditioned DCs suppressed the encephalitogenic TH1 and TH17 response and halted established chronic EAE. Thus, vaccination with IL-27-conditioned tolerogenic DCs can provide a new avenue for the treatment of autoimmune diseases. Alternatively, nanoparticles have been previously developed for delivery of antigens in vivo to induce antigen-specific tolerance[46]. Accordingly, in some embodiments, nanoparticles engineered to activate IL-27 signaling and deliver myelin antigens, e.g., specifically to DCs, can induce tolerogenic DCs in vivo and arrest pathogenic T cell responses. That approach can exploit the immunoregulatory properties of IL-27 and overcome the limitations associated with the implementation of cell-based therapies in a clinical setting. Presented herein shows that IL-27 signaling in DCs limited the differentiation of pathogenic TH1 and TH17 cells and the development of CNS autoimmunity through a mechanism that was at least partially dependent on CD39. This immunoregulatory pathway can provide new therapeutic avenues for MS and other autoimmune disorders.

Exemplary Methods and Materials Used in Examples 1-8

Animals.

IL-27RA- and CD39-deficient mice have been previously described in Refs 25 and 36. SJL, 2D2, C57BL/6, CD11c-Cre:DTR and IL-10 deficient mice were from the Jackson Laboratories. For conditional ablation of DCs (CD11c-DTR→WT), bone marrow chimeras were inoculated intraperitoneally every second day for 2 weeks with 16 ng DTx per gram body weight. For the generation of bone marrow chimeras, recipient mice were lethally irradiated with a dose of 9.5 Gy and 1 d later were given intravenous injection of $5 \times 10^6$ bone marrow cells isolated from donor femora and tibiae. Recipients of bone marrow were then allowed to rest for 8 weeks before use. Four to five randomly assigned mice were used per experimental group per experiment. Mice were kept in a conventional, pathogen-free facility. All experiments were carried out in accordance with guidelines of the Institutional Animal Care and Use Committee.

Isolation of Splenic DCs and CNS Infiltrates.

Spleens were incubated for 20 min with 2 mg/ml collagenase D and then were mashed through a 70-μm cell strainer. DCs were sorted as previously described (in Ref. 36) into $F4/80^-$ $CD11b^-CD11c^{lo}$ $B220^+$ $MHCII^{lo}$ $Ly6C^+$ pDCs and $F4/80^-$ $CD11b^+$ $CD11c^+$ $B220^-$ $MHCII^+$ $Ly6C^-$ cDCs (eBioscience). cCs were cultured for 48 h with IL-27 (20 ng/ml) or ecLPS (100 ng/ml; E. coli strain 0111:B4; Sigma). Parallel cultures maintained without stimuli were used as controls. IL-27 was prepared according to the manufacturer's protocol (eBioscience).

CNS infiltrates were isolated as previously described in Ref. 47. Mice were perfused with ice-cold PBS. The brain and spinal cord were removed and incubated in PBS containing collagenase type III (2 mg/ml; Worthington) and DNase (20 units/ml; Sigma-Aldrich). Tissues were then homogenized and loaded on a 30%-37%-70% Percoll gradient for enrichment of CNS infiltrates.

Flow Cytometry Staining and Acquisition.

The following antibodies were used for flow cytometry: peridinin chlorophyll protein-conjugated anti-LY6C (HK1.4) and allophycocyanin-conjugated anti-CD11b (M1/70; both from BioLegend); phycoerythrin-conjugated antibody to MHC class II (M5/114.15.2), fluorescein isothiocyanate-conjugated anti-F4/80 (BM8) and Alexa Fluora 647-anti-CD39 (24DMS1; all from eBioscience); allophycocyanin-indotricarbocyanine-conjugated anti-CD11c (HL3) and phycoerythrin conjugated anti-B220 (RA3-6B2; all from BD Pharmingen); and fluorescein isothiocyanate-conjugated anti-IL-27RA (263503; R&D Systems).

For analysis of intracellular Foxp3, cell preparations were stained for cell surface markers with allophycocyanin-indotricarbocyanine-conjugated anti-CD4 (RM4-5; BioLegend), then were fixed and made permeable with fixation-permeabilization buffers (eBioscience) and were stained with peridinin chlorophyll protein-cyanine 5.5-conjugated anti-Foxp3 (FJK-16s; eBioscience).

For intracellular cytokine staining, cells were stimulated for 6 h with phorbol 12-myrCistate 13-acetate (50 ng/ml) and ionomycin (500 ng/ml) in the presence of GolgiPlug (BD Pharmingen). Then, cells were stained for surface molecules (antibodies identified above), fixed and made permeable with a Cytofix/Cytoperm Plus kit (BD Bioscience) and stained with the following antibodies: phycoerythrin-indotricarbocyanine-conjugated anti-IFN-γ (XMG1.2; BioLegend), phycoerythrin-conjugated anti-IL-17 (eBio17B7; eBioscience) and allophycocyanin-conjugated anti-IL-10 (JES5-16E3; BD Pharmingen). Data were collected with a LSR II or FACSAria (BD Biosciences), then were analyzed with FlowJo software (Treestar).

Proliferation Assays.

For in vitro experiments, cDCs pretreated with IL-27 (20 ng/ml) and activated for 48 h with ecLPS (100 ng/ml; E coli strain 0111:B4; Sigma) were used (at a ratio of 1:10) to stimulate naive T cells from wild-type or 2D2 mice. Polarizing conditions have been previously described in Ref. 48: IL-12 (30 ng/ml) was used to generate TH1 cells, or IL-6 (30 ng/ml); TGF-β1 (3 ng/ml) was used to generate TH17 cells; and TGF-β1 (5 ng/ml) and IL-27 (30 ng/ml) were used to generate Treg cells and Tr1 cells, respectively. Mouse IL-6, IL-12, IL-23 and TGF-β1 were all from R&D Systems For in vivo experiments, splenic cells were obtained from wild type, IL27RA- or CD39-deficient mice at day 21 after immunization with MOG(35-55) and were restimulated in vitro for 3 d in the presence of MOG(35-55). SJL mice were immunized with PLP(139-151), and at the end of the experiment, splenic cells were collected and restimulated in vitro for 3 d in the presence of PLP(139-151) or PLP(178-191). The cells were pulsed with [$^3$H]thymidine (1 μCi/well) for the final 24 h of the incubation period. The frequency of T cells producing IL-17 (eBio17B7; eBioscience), IFN-γ (XMG1.2; BioLegend) or IL-10 (JES5-16E3; BD Pharmingen) and Foxp3$^+$ T cells (FJK-16s; eBioscience) was assessed by flow cytometry. For CFSE-based proliferation assay, 2D2 CD4+ T cells were labeled with 1 μM CFSE (carboxyfluorescein diacetate succinimidyl ester; Molecular Probes) Data were acquired on an LSR II (BD Biosciences) and were analyzed with FlowJo software (TreeStar).

Measurement of Cytokines.

Secreted cytokines were measured after 48 h by enzyme-linked immunosorbent assay as previously described in Ref. 49.

Quantitative PCR Analysis.

RNA was extracted with RNAeasy columns (Qiagen, USA), then cDNA was prepared according to the manufacturer's instructions (Applied Biosystems) and was used as template for real-time PCR All primers and probes were provided by Applied Biosystems and were used on the ViiA 7 Real-Time PCR System (Applied Biosystems). Expression was normalized to the expression of the housekeeping gene Gapdh Primers-probe mixtures were as follows (from Applied Biosystems; identifiers in parentheses): Il6 (Mm00446190_m1), Il10 (Mm0043614_m1), Il12a (Mm00434165_m1), Il23a (Mm00518984_m1), Il27 (Mm00461162_m1), Il27ra (Mm00497259_m1), Entpd1 (Mm00515447_m1), Tgfb1 (Mm01178820_m1), Ifnb1 (Mm00439552_s1), Ido1 (Mm0001218007_m1), Ido2 (Mm01218007_m1), Tnip3 (Mm01181626_m1), Tnfaip3 (Mm00437121_m1), Ramp3 (Mm00840142_m1), Esr1 (Mm00433151_m1) and Gapdh (Mm99999915_g1).

Gene-Expression Analysis.

Transcriptomes were analyzed by Affymetrix microarray MoGene_1_0_st of samples obtained 0, 2 and 6 h after stimulation with LPS or IL-27 and LPS. Data were normalized with the robust multiarray average algorithm. Network activity was determined with the NetGenerator algorithm and software of the R project for statistical computing (version 2.1-3)[24] using as input the change of gene expression (fold) over time points. The network graph was produced with DOT plain text graph description language through the open software collection Graphviz.

For nCounter analysis of gene expression, a 'multiplexed' target profiling of 146 inflammation- and immune system-related transcripts was customized and used in accordance with the manufacturer's protocol (Nanostring). This combination of genes and their differences in expression in vivo in DCs allowed investigation of immune system-related pathways during EAE with the EXPANDER tool ('expression analyzer and displayer').

Immunoblot Analysis.

For immunoblot analysis, cells were lysed with radioimmunoprecipitation buffer supplemented with protease inhibitor 'cocktail' (Sigma). Total lysates of DCs (40 μg) were resolved by electrophoresis through 4-12% Bis-Tris Nupage gels (Invitrogen, USA) and were transferred onto PVDF membranes (Millipore). The following primary antibodies were used: anti-IL-27RA (MAB21091; R&D Systems); antibody to phosphorylated STAT3 (9134), antibody to phosphorylated STAT1 (9167), anti-STAT3 (9132), anti-STAT1 (9172) and anti-GAPDH (2111; all from Cell Signaling Technology); anti-caspase-1 (ab17820), anti-IL-1β (ab9722) and anti-β-actin (ab20272; all from Abcam). Immunoblot analysis was done as previously described in Ref. 47 and blots were developed with SuperSignal West Femto Maximum Sensitivity Substrate as suggested by the manufacturer (Pierce).

Chromatin Immunoprecipitation.

DNA-protein complexes in cells were crosslinked with 1% paraformaldehyde and lysed with 0.35 ml lysis buffer (1% SDS, 10 mM EDTA and 50 mM Tris-HCl, pH 8.1) containing 1× protease inhibitor 'cocktail' (Roche Molecular Biochemicals). Chromatin was sheared by sonication and supernatants collected after centrifugation were diluted in buffer (1% Triton X-100, 2 mM EDTA, 150 mM NaCl and 20 mM Tris-HCl, pH 8.1). 5 μg antibody was prebound for a minimum of 4 h to protein A and protein G Dynal magnetic beads (Invitrogen) and samples were washed three times with ice-cold PBS containing 5% BSA, and then were added to the diluted chromatin, followed by immunoprecipitation overnight. The magnetic bead-chromatin complexes were then washed three times in radioimmunoprecipitation buffer (50 mM HEPES, pH 7.6, 1 mM EDTA, 0.7% Na deoxycholate, 1% NP-40 and 0.5 M LiCl), followed by two washes with Tris-EDTA buffer. Immunoprecipitated chromatin was then extracted with a solution of 1% SDS and 0.1 M NaHCO$_3$ and was heated at 65° C. for at least 6 h for reversal of the paraformaldehyde cross-linking. DNA fragments were purified with a QIAquick DNA purification Kit (Qiagen) and were analyzed by SYBR Green real-time PCR (Takara Bio). The following antibodies were used for chromatin immunoprecipitation: anti-STAT3 (9132; Cell Signaling Technology) and anti-STAT1 (9172; Cell Signaling Technology). The following primer pairs were used:

```
                                           (SEQ ID NO: 2)
Stat3 (SRE-1), forward,
5'-GCTGGGCTTTAGAGACTTGTGG GC-3'
and (SEQ ID NO: 3)
reverse,
5'-ACCCATGCAAATGGTTTGGGCA-3';

(SEQ ID NO: 4)
Stat3 (SRE-2), forward,
5'-TGAGGGCCAGCCCACACTTCA-3',
and (SEQ ID NO: 5)
rev:
5'-GCTCACTGGGTACCTCTTGCCA-3';

(SEQ ID NO: 6)
Stat1 (IRF), forward,
5'-GGAACAAAAATATAGAGAGAACTTGGGA-3',
and (SEQ ID NO: 7)
reverse,
5'-GTAGTTTGACCTAAGTGGACATAGG-3';

(SEQ ID NO: 8)
Stat1-Stat3, forward,
5'-AGGCTCTTGTATCCTTGCCACCTCT-3',
and (SEQ ID NO: 9)
reverse,
5'-TGATGGTGGAGTGCTGTGTGCTG-3'.
```

Transfection and Luciferase Assays.

HEK293 cells were grown in DMEM supplemented with 10% FBS and were transfected with FuGENE HD transfection reagent and 2 μg of each plasmids according the manufacturer's instructions (Roche). Firefly and renilla luciferase activity was analyzed 48 h after transfection with a Dual Luciferase Assay kit (Promega).

Free ATP Measurement.

cDCs were cultured for 48 h with IL-27 or LPS as described above (Isolation of splenic DCs and CNS infiltrates). Cells were then washed twice with phenol red-free RPMI-1640 medium (Gibco) and were deprived of serum for 24 h. Cell-free medium was then analyzed for endogenous ATP with ENTILEN rLuciferase/Luciferin reagent (Promega). Bioluminescent activity was measured with an Infinite 200 Proluminometer (Tecan).

Ectonucleotidase Enzymatic Activity Analysis.

Thin-layer chromatography was done as previously described in Ref. 25 with slight modifications. 1×10$^5$ DCs were treated for 48 h with IL-27 or LPS, then were incubated with 2 mCi/ml [$^{14}$C]ADP (GE Healthcare Life Sciences) in 10 mM Ca$^{2+}$ and 5 mM Mg$^{2+}$. Hydrolysis products of [$^{14}$C]ADP were assessed by TLC in 5-μl aliquots collected at 1.5, 3 and 6 min and were applied onto silica gel matrix plates (Sigma-Aldrich). [$^{14}$C]ADP and its radiolabeled derivatives were separated with the appropriate solvent mixture as described previously in Refs. 25 and 50. Adenosine uptake and deamination was blocked with 10 μM dipyridamole. [$^{14}$C]ADP, [$^{14}$C]AMP and [$^{14}$C]ADO incubated in PBS served as standards.

EAE Induction and Vaccination with DCs.

EAE was induced by subcutaneous immunization of mice with 150 μg MOG(35-55) or 30 μg PLP(139-151)

(ANASPEC) as previously described in Ref. 49. Adoptive transfer EAE was induced as previously described in Ref. 48 with some modifications. 2D2 mice were immunized with 150 μg MOG(35-55) in complete Freund's adjuvant, and draining lymph nodes and spleens were collected 7 d after immunization and then were cultured for 48 h with MOG (35-55) (20 μg/ml) and carrier free recombinant IL-12 (20 ng/ml; R&D Systems) or IL-23 (20 ng/ml; R&D Systems). Subsequently, 5×10[6] cells were transferred intravenously into DC(WT) or DC(IL-27RA-KO) mice. Clinical signs of EAE were assessed by investigators 'blinded' to treatment conditions, according to the following score: 0, no disease; 1, loss of tail tone; 1.5, poor righting ability; 2, hind-limb weakness; 3, hind-limb paralysis; 4, quadreparesis; and 5, moribund.

For the generation of bone marrow-derived DCs, bone marrow cells isolated from the femurs of naive mice were cultured for 7 d in the presence of the cytokine GM-CSF (20 ng/mL; Peprotech). On day 7, cells were purified with CD11c+ magnetic beads (Miltenyi), then were cultured for 18 h with IL-27 (20 ng/ml) and, for the final 3 h before administration, were loaded with 20 μg MOG(35-55) or PLP(139-151) DCs (2×10[6] cells per mouse) were then extensively washed and administered intravenously four times, once every 4 d All experiments were carried out in accordance with guidelines prescribed by the Institutional Animal Care and Use Committee.

Antigen Microarray.

Antigens were spotted onto Epoxy slides (TeleChem) as described[34]. Nonspecific binding on microarrays was blocked with 1% bovine serum albumin, followed by incubation with test serum (1:100 dilution in blocking buffer). Arrays were then washed and incubated with indocarbocyanine-conjugated goat antibody to mouse immunoglobulin G (detection antibody; 115-166-072; Jackson ImmunoResearch Labs). Antigen reactivity was defined by the mean intensity of binding to the replicates of that antigen on the microarray. Raw data were normalized and analyzed with GeneSpring software (Silicon Genetics).

Statistical Analysis.

Prism software was used for statistical analysis. Statistical analysis was done according to the recommendations of Nature for reporting life sciences research. For comparison of two groups, linear regression with 95% confidence interval, and unpaired, two-tailed Student's t-test were used. One-way ANOVA for paired data was used to determine the significance of the time-response curves. P values of <0.05 were considered statistically significant. For adjustment of the significance value for multiple comparisons, a Bonferroni correction was applied with a corrected significance value of 0.017.

Example 9. Tolerogenic Biotherapuetics Targeting the IL-27/Ectonucleotidase Axis Several Treg subsets enforce immune tolerance, of particular importance are FoxP3+ Tregs and IL-10+ type 1 regulatory T cells (Tr1 cells)[2]. Deficits in pancreatic FoxP3+ Tregs have been described in T1D patients, and Teffs from T1D patients might be resistant to regulation by FoxP3+ Tregs[3]. With regards to IL-10+ Tr1 cells, IL-10 secretion by islet-specific T cells is reduced in newly diagnosed T1D patients[4]. Conversely, Tr1 cells enforce tolerance in preclinical models of islet transplantation[5], and the arrest of diabetes by Teplizumab (anti-CD3) is linked to IL-10 production by T cells[6].

Figures 14A, 14B, 14C:
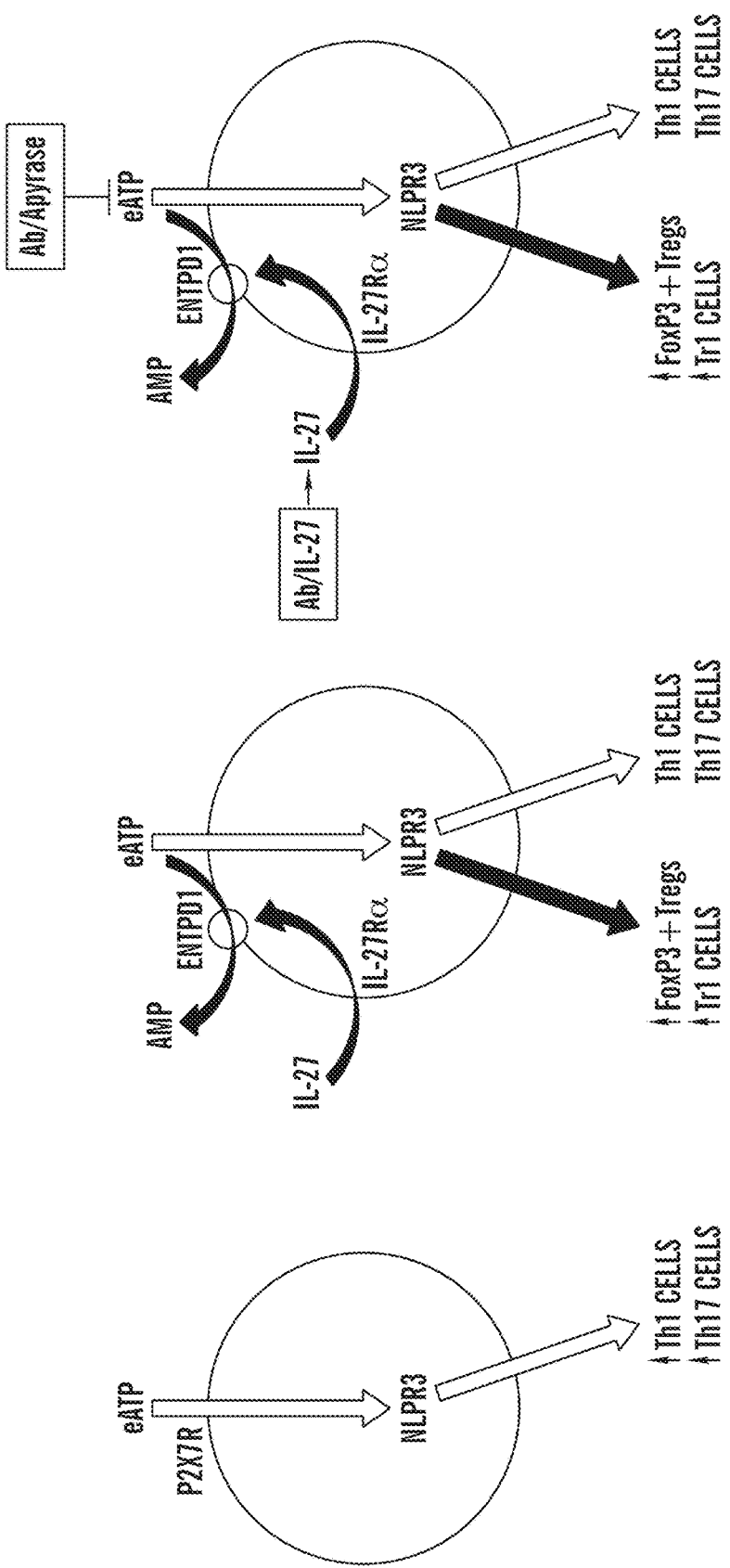
FIGS. 14A-14C show that IL-27 acts on DCs to control Treg and Teff differentiation via ENTPD1 (CD39) upregulation.

The re-establishment of immune tolerance can be beneficial for the treatment of type 1 diabetes (T1D). Dendritic cells (DCs) control the balance between effector and regulatory T cells (Teffs and Tregs, respectively). As described in Examples 1-8, IL-27 acts on DCs to expand Tregs, and thus can limit Teffs and suppress disease in models of T1D and multiple sclerosis (MS) (FIGS. 14A-14B). Moreover, as presented earlier, the anti-inflammatory effects of IL-27 on DCs were mediated by the up-regulation of the ectonucleotidase CD39 (ENTPD1) and the consequent decrease in the levels of pro-inflammatory extracellular ATP (eATP). Accordingly, fusion proteins that incorporate DC-targeting antibodies and IL-27 or the ATP-degrading protein apyrase can be developed as therapy for T1D (FIG. 14C). In some embodiments, these anti-inflammatory biotherapeutics can be repurposed to treat a broad array of immune-mediated diseases.

IL-27 induces Tr1 cell differentiation mediated by the aryl hydrocarbon receptor[7, 8]. Thus, IL-27 and Tr1 cells play an important role in suppressing pre-existing inflammation, particularly because Teffs are resistant to the suppressive activity of FoxP3+ Tregs in inflamed tissues[9].

The IL-27 receptor (IL-27Ra) is expressed by T cells, and also by innate immune cells such as DCs[10, 11]. IL-27 polymorphisms have been linked to T1D[12]. However, it is not known that IL-27 can act on DCs or induce an immunosuppressive effect on DCs. Indeed, the inventors discovered that IL-27 acts on DCs to expand Tregs, limit Teffs, and arrest the development of experimental T1D and multiple sclerosis. These tolerogenic effects of IL-27 on DCs were mediated by the up-regulation of the ectonucleotidase CD39 and the consequent decrease in pro-inflammatory eATP (FIGS. 14A-14B). The IL-27 also induced the expression of other tolerogenic molecules in DCs, such as IDO 1.

While IL-27 can be administered to treat autoimmune disorders, non-targeted systemic cytokine administration can be associated with side effects that limit its clinical use. Accordingly, in one aspect, a biotherapeutic comprising a DC-targeting antibody fused to IL-27 or apyrase, an ATP-degrading protein, can be used to target the IL-27/ectonucleotidase axis and re-establish tolerance in T1D and other immune-mediated disorders (FIG. 14C).

CD39-deficiency worsens diabetes in mice, and CD39 limits renal injury and promotes β-cell regeneration[13-16]. Thus, in some embodiments, targeting the IL-27/ectonucleotidase axis can activate additional tissue-protective mechanisms that may boost the efficacy of a therapeutic in T1D and support its repurposing to treat other inflammatory disorders (e.g. lupus nephritis).

Exemplary Biotherapeutic Drug Candidate:

In some embodiments, a biotherapeutic can comprise a DC-targeting antibody fused to IL-27 or an ATP-degrading protein (e.g., apyrase such as potato (S. tuberosum) apyrase). In some embodiments, the DC-targeting antibody can be a single chain antibody targeting Clec9A, which is expressed by human DCs[17]. Alternatively, the DC-targeting antibody can be a single chain antibody targeting DEC205, although its expression is less specific, particularly in humans.

While previous report shows that the p-cell specific delivery of NF-kB inhibitors suppresses experimental T1D[18], targeted delivery of anti-inflammatory IL-27 to β-cells or the kidney is not known. In some embodiments, it can be desirable to conjugate apyrase or IL-27 to antibodies targeting β-cells or kidney, which can be used as a therapeutic approach for T1D and nephritis. Similarly, the local delivery of apyrase to β-cells or the kidney might boost β-cell regeneration and limit renal injury. In some embodiments, the biotherapeutic described herein can be used in combination with other immunotherapies in T1D (e.g. IL-7Ra blocking antibodies[19]) to treat diabetic nephropathy or promote β-cell survival, and can alternatively be repurposed for other clinical autoimmune indications (e.g. lupus nephritis).

The biotherapeutics can be analyzed on murine T1D systems and cells in vitro, and also on human cells from controls and T1D patients. Further, IL-27Ra and CD39 expression can be analyzed in T1D patients, to evaluate the relevance of the IL-27/CD39 pathway in T1D and the utility of these molecules as biomarkers for patient stratification and monitoring.

To study the effects of biotherapeutics described herein in pre-clinical models of T1D, biotherapeutics, e.g., targeting IL-27/ectonucleotidase pathway, are used to evaluate their effects on murine T1D models. The targeting-specificity of the biotherapeutics is analyzed using cells in vitro, and also upon in vivo administration. The activity of the antibody-fused IL-27 or apyrase on DCs in vitro is also measured to determine whether IL-27 or apyrase fusion to the antibody can affect their biological activity. These in vivo and in vitro functional assays can analyze the effects of the biotherapeutics on DC survival and maturation, and T cell activation and polarization into Teffs and Tregs in vivo and in vitro. IL-27- and CD39-deficient mice, as well as recombinant IL-27 or apyrase, can be used as controls. In addition, the effects of the biotherapeutics on murine models of T1D can be assessed in preventive and therapeutic paradigms.

Dysregulated T-cell responses and IL-27 and CD39 (ENTPD1) polymorphisms have been previously reported in T1D. To investigate the effects of biotherapeutics described herein on T1D and control samples, IL-27Ra, CD39 and the functional effects of targeting the IL-27/ectonucleotidase axis with biotherapeutics are determined in control and T1D samples. IL-27Ra and CD39 expression are first analyzed in untreated or biotherapeutic-treated DCs and T cells from controls and T1D samples. This can determine whether these molecules can be used to stratify patients and monitor their response to therapy.

To evaluate the efficacy of a biotherapeutic described herein on treatment of T1D, newly diagnosed T1D patients within 6 weeks of diagnosis and positive for anti-GAD65, anti-ICA512, or ICA. ENTPD1 polymorphisms are used in patient selection and treated with either a placebo or a biotherapeutic described herein. Change from baseline in mean C-peptide area under the curve, insulin use and/or HbA1 levels can be measured at an indicated time point after administration. To study the effects of the biotherapeutic on IL-27/ectonucleotidase axis, CD39 expression is analyzed in blood DCs, which is up-regulated by IL-27. As there is a transcriptional signature of the response of DCs to IL-27, mRNA expression is also determined. These parameters are then correlated with the biodistribution and cell-targeting of the biotherapeutic in patients. Further, the ability of blood DCs to activate T cells in vitro is analyzed. In addition, T cells and DCs in PBMCs are analyzed, e.g., by CyTOF, for the expression of surface and intracellular markers (e.g. FoxP3, IL-10, IL-17, etc.); insulin-specific T-cells are analyzed, e.g., with tetramers and by ELISPOT.

REFERENCES FOR EXAMPLES 1-8 AND SPECIFICATION

1. Nylander, A. & Hafler, D. A. Multiple sclerosis. J. Clin. Invest. 122, 1180-1188 (2012).
2. Pierson, E., Simmons, S. B., Castelli, L. & Goverman, J. M. Mechanisms regulating regional localization of inflammation during CNS autoimmunity. Immunol. Rev. 248, 205-215 (2012).
3. Bailey, S. L., Schreiner, B., Mcmahon, E. J. & Miller, S. D. CNS myeloid DCs presenting endogenous myelin peptides 'preferentially' polarize CD4+ TH-17 cells in relapsing EAE. Nat. Immunol. 8, 172-180 (2007).
4. Yogev, N. et al. Dendritic cells ameliorate autoimmunity in the CNS by controlling the homeostasis of PD-1 receptor+ regulatory T cells. Immunity 37, 264-275 (2012).
5. Comabella, M., Montalban, X., Münz, C. & Lünemann, J. D. Targeting dendritic cells to treat multiple sclerosis. Nat. Rev. Nephrol. 6, 499-507 (2010).
6. Greter, M. et al. Dendritic cells permit immune invasion of the CNS in an animal model of multiple sclerosis. Nat. Med. 11, 328-334 (2005).
7. McMahon, E. J., Bailey, S. L., Castenada, C. V., Waldner, H. & Miller, S. D. Epitope spreading initiates in the CNS in two mouse models of multiple sclerosis. Nat. Med. 11, 335-339 (2005).
8. Kastelein, R. A., Hunter, C. A. & Cua, D. J. Discovery and biology of IL-23 and IL-27: related but functionally distinct regulators of inflammation. Annu. Rev. Immunol. 25, 221-242 (2007).
9. Molle, C., Goldman, M. & Goriely, S. Critical role of the IFN-stimulated gene factor 3 complex in TLR-mediated IL-27p28 gene expression revealing a two-step activation process. J. Immunol. 184, 1784-1792 (2010).
10. Mitsdoerffer, M. & Kuchroo, V. New pieces in the puzzle: how does interferon-β really work in multiple sclerosis? Ann. Neurol. 65, 487-488 (2009).
11. Hunter, C. A. & Kastelein, R. Interleukin-27: balancing protective and pathological immunity. Immunity 37, 960-969 (2012).
12. Fitzgerald, D. C. et al. Suppressive effect of IL-27 on encephalitogenic Th17 cells and the effector phase of experimental autoimmune encephalomyelitis. J. Immunol. 179, 3268-3275 (2007).
13. Batten, M. et al. Interleukin 27 limits autoimmune encephalomyelitis by suppressing the development of interleukin 17-producing T cells. Nat. Immunol. 7, 929-936 (2006).
14. Awasthi, A. et al. A dominant function for interleukin 27 in generating interleukin 10-producing anti-inflammatory T cells. Nat. Immunol. 8, 1380-1389 (2007).
15. Fitzgerald, D. C. et al. Suppression of autoimmune inflammation of the central nervous system by interleukin 10 secreted by interleukin 27-stimulated T cells. Nat. Immunol. 8, 1372-1379 (2007).
16. Stumhofer, J. S. et al. Interleukin 27 negatively regulates the development of interleukin 17-producing T helper cells during chronic inflammation of the central nervous system. Nat. Immunol. 7, 937-945 (2006).
17. Stumhofer, J. S. et al. Interleukins 27 and 6 induce STAT3-mediated T cell production of interleukin 10. Nat. Immunol. 8, 1363-1371 (2007).
18. Wang, S., Miyazaki, Y., Shinozaki, Y. & Yoshida, H. Augmentation of antigen-presenting and Th1-promoting functions of dendritic cells by WSX-1(IL-27R) deficiency. J. Immunol. 179, 6421-6428 (2007).
19. Karakhanova, S., Bedke, T., Enk, A. H. & Mahnke, K. IL-27 renders DC immunosuppressive by induction of B7-H1. J. Leukoc. Biol. 89, 837-845 (2011).
20. Matta, B. M., Raimondi, G., Rosborough, B. R., Sumpter, T. L. & Thomson, A. W. IL-27 production and STAT3-dependent upregulation of B7-H1 mediate immune regulatory functions of liver plasmacytoid dendritic cells. J. Immunol. 188, 5227-5237 (2012).
21. Guermonprez, P., Valladeau, J., Zitvogel, L., Thery, C. & Amigorena, S. Antigen presentation and T cell stimulation by dendritic cells. Annu. Rev. Immunol. 20, 621-667 (2002).
22. Jung, S. et al. In vivo depletion of CD11c+ dendritic cells abrogates priming of CD8+ T cells by exogenous cell-associated antigens. Immunity 17, 211-220 (2002).
23. Ma, A. & Malynn, B. A. A20: linking a complex regulator of ubiquitylation to immunity and human disease. Nat. Rev. Immunol. 12, 774-785 (2012).
24. Weber, M. et al. Inference of dynamical gene-regulatory networks based on time-resolved multi-stimuli multi-experiment data applying NetGenerator V2.0. BMC Syst. Biol. 7, 1 (2013).
25. Deaglio, S. et al. Adenosine generation catalyzed by CD39 and CD73 expressed on regulatory T cells mediates immune suppression. J. Exp. Med. 204, 1257-1265 (2007).
26. Gandhi, R. et al. Activation of the aryl hydrocarbon receptor induces human type 1 regulatory T cell-like and Foxp3+ regulatory T cells. Nat. Immunol. 11, 846-853 (2010).
27. Chalmin, F. et al. Stat3 and Gfi-1 transcription factors control Th17 cell immunosuppressive activity via the regulation of ectonucleotidase expression. Immunity 36, 362-373 (2012).
28. Eltzschig, H. K., Sitkovsky, M. V. & Robson, S. C. Purinergic signaling during inflammation. N. Engl. J. Med. 367, 2322-2333 (2012).
29. Mariathasan, S. et al. Cryopyrin activates the inflammasome in response to toxins and ATP. Nature 440, 228-232 (2006).
30. Gris, D. et al. NLRP3 plays a critical role in the development of experimental autoimmune encephalomyelitis by mediating Th1 and Th17 responses. J. Immunol. 185, 974-981 (2010).
31. Martinon, F., Mayor, A. & Tschopp, J. The inflammasomes: guardians of the body. Annu. Rev. Immunol. 27, 229-265 (2009).
32. Tacken, P. J., de Vries, I. J., Torensma, R. & Figdor, C. G. Dendritic-cell immunotherapy: from ex vivo loading to in vivo targeting. Nat. Rev. Immunol. 7, 790-802 (2007).
33. Dhodapkar, M. V., Steinman, R. M., Krasovsky, J., Munz, C. & Bhardwaj, N. Antigen-specific inhibition of effector T cell function in humans after injection of immature dendritic cells. J. Exp. Med. 193, 233-238 (2001).
34. Quintana, F. J. et al. Antigen microarrays identify unique serum autoantibody signatures in clinical and pathologic subtypes of multiple sclerosis. Proc. Natl. Acad. Sci. USA 105, 18889-18894 (2008).
35. Robinson, W. H. et al. Protein microarrays guide tolerizing DNA vaccine treatment of autoimmune encephalomyelitis. Nat. Biotechnol. 21, 1033-1039 (2003).
36. Apetoh, L. et al. The aryl hydrocarbon receptor interacts with c-Maf to promote the differentiation of type 1 regulatory T cells induced by IL-27. Nat. Immunol. 11, 854-861 (2010).
37. Moore, K. W., de Waal Malefyt, R., Coffman, R. L. & O'Garra, A. Interleukin-10 and the interleukin-10 receptor. Annu. Rev. Immunol. 19, 683-765 (2001).
38. Melillo, J. A. et al. Dendritic cell (DC)-specific targeting reveals Stat3 as a negative regulator of DC function. J. Immunol. 184, 2638-2645 (2010).
39. Baker, B. J., Park, K. W., Qin, H., Ma, X. & Benveniste, E. N. IL-27 inhibits OSM-mediated TNF-α and iNOS gene expression in microglia. Glia 58, 1082-1093 (2010).
40. Färber, K. et al. The ectonucleotidase cd39/ENTPDase1 modulates purinergic-mediated microglial migration. Glia 56, 331-341 (2008).
41. Mizumoto, N. et al. CD39 is the dominant Langerhans cell-associated ecto-NTPDase: modulatory roles in inflammation and immune responsiveness. Nat. Med. 8, 358-365 (2002).
42. Sutterwala, F. S. et al. Critical role for NALP3/CIAS1/Cryopyrin in innate and adaptive immunity through its regulation of caspase-1. Immunity 24, 317-327 (2006).
43. Eisenbarth, S. C., Colegio, O. R., O'Connor, W., Sutterwala, F. S. & Flavell, R. A. Crucial role for the Nalp3 inflammasome in the immunostimulatory properties of aluminium adjuvants. Nature 453, 1122-1126 (2008).
44. Meng, G., Zhang, F., Fuss, I., Kitani, A. & Strober, W. A mutation in the Nlrp3 gene causing inflammasome hyperactivation potentiates Th17 cell-dominant immune responses. Immunity 30, 860-874 (2009).
45. Jähnisch, H. et al. Dendritic cell-based immunotherapy for prostate cancer. Clin. Dev. Immunol. 2010, 517493 (2010).
46. Yeste, A., Nadeau, M., Burns, E. J., Weiner, H. L. & Quintana, F. J. Nanoparticle-mediated codelivery of myelin antigen and a tolerogenic small molecule suppresses experimental autoimmune encephalomyelitis. Proc. Natl. Acad. Sci. USA 109, 11270-11275 (2012).
47. Starossom, S. C. et al. Galectin-1 deactivates classically activated microglia and protects from inflammation-induced neurodegeneration. Immunity 37, 249-263 (2012).
48. Quintana, F. J. et al. Aiolos promotes TH17 differentiation by directly silencing l2 expression. Nat. Immunol. 13, 770-777 (2012).
49. Quintana, F. J. et al. Control of Treg and TH17 cell differentiation by the aryl hydrocarbon receptor. Nature 453, 65-71 (2008).
50. Sun, X. et al. CD39/ENTPD1 expression by CD4+ Foxp3+ regulatory T cells promotes hepatic metastatic tumor growth in mice. Gastroenterology 139, 1030-1040 (2010).

REFERENCES FOR EXAMPLE 9

1. Mascanfroni, I. D., Yeste, A., Vieira, S. M., Burns, E. J., Patel, B., Sloma, I., Wu, Y., Mayo, L., Ben-Hamo, R., Efroni, S., Kuchroo, V. K., Robson, S. C. & Quintana, F. J. IL-27 acts on DCs to suppress the T cell response and autoimmunity by inducing expression of the immuno-regulatory molecule CD39. Nat Immunol 14, 1054-1063 (2013).
2. Sakaguchi, S. Naturally arising CD4+ regulatory t cells for immunologic self-tolerance and negative control of immune responses. Annual review of immunology 22, 531-562 (2004).
3. Herold, K. C., Vignali, D. A., Cooke, A. & Bluestone, J. A. Type 1 diabetes: translating mechanistic observations into effective clinical outcomes. Nat Rev Immunol 13, 243-256 (2013).
4. Petrich de Marquesini, L. G., Fu, J., Connor, K. J., Bishop, A. J., McLintock, N. E., Pope, C., Wong, F. S. & Dayan, C. M. IFN-gamma and IL-10 islet-antigen-specific T cell responses in autoantibody-negative first-degree relatives of patients with type 1 diabetes. Diabetologia 53, 1451-1460 (2010).

5. Gagliani, N., Jofra, T., Stabilini, A., Valle, A., Atkinson, M., Roncarolo, M. G. & Battaglia, M. Antigen-specific dependence of Tr1-cell therapy in preclinical models of islet transplant. Diabetes 59, 433-439 (2009).
6. Waldron-Lynch, F., Henegariu, O., Deng, S., Preston-Hurlburt, P., Tooley, J., Flavell, R. & Herold, K. C. Teplizumab induces human gut-tropic regulatory cells in humanized mice and patients. Sci Transl Med 4, 118ra112 (2012).
7. Apetoh, L., Quintana, F. J., Pot, C., Joller, N., Xiao, S., Kumar, D., Burns, E. J., Sherr, D. H., Weiner, H. L. & Kuchroo, V. K. The aryl hydrocarbon receptor interacts with c-Maf to promote the differentiation of type 1 regulatory T cells induced by IL-27. Nature Immunology 11, 854-861 (2010).
8. Gandhi, R., Kumar, D., Burns, E. J., Nadeau, M., Dake, B., Laroni, A., Kozoriz, D., Weiner, H. L. & Quintana, F. J. Activation of the aryl hydrocarbon receptor induces human type 1 regulatory T cell-like and Foxp3(+) regulatory T cells. Nature Immunology 11, 846-853 (2010).
9. Korn, T., Reddy, J., Gao, W., Bettelli, E., Awasthi, A., Petersen, T. R., Backstrom, B. T., Sobel, R. A., Wucherpfennig, K. W., Strom, T. B., Oukka, M. & Kuchroo, V. K. Myelin-specific regulatory T cells accumulate in the CNS but fail to control autoimmune inflammation. Nature Medicine 13, 423-431 (2007).
10. Hunter, C. A. & Kastelein, R. Interleukin-27: balancing protective and pathological immunity. Immunity 37, 960-969 (2012).
11. Wojno, E. D. & Hunter, C. A. New directions in the basic and translational biology of interleukin-27. Trends in immunology 33, 91-97 (2012).
12. Barrett, J. C., Clayton, D. G., Concannon, P., Akolkar, B., Cooper, J. D., Erlich, H. A., Julier, C., Morahan, G., Nerup, J., Nierras, C., Plagnol, V., Pociot, F., Schuilenburg, H., Smyth, D. J., Stevens, H., Todd, J. A., Walker, N. M. & Rich, S. S. Genome-wide association study and meta-analysis find that over 40 loci affect risk of type 1 diabetes. Nature genetics 41, 703-707 (2009).
13. Chia, J. S., McRae, J. L., Cowan, P. J. & Dwyer, K. M. The CD39-adenosinergic axis in the pathogenesis of immune and nonimmune diabetes. Journal of biomedicine & biotechnology 2012, 320495 (2012).
14. Friedman, D. J., Rennke, H. G., Csizmadia, E., Enjyoji, K. & Robson, S. C. The vascular ectonucleotidase ENTPD1 is a novel renoprotective factor in diabetic nephropathy. Diabetes 56, 2371-2379 (2007).
15. Friedman, D. J., Talbert, M. E., Bowden, D. W., Freedman, B. I., Mukanya, Y., Enjyoji, K. & Robson, S. C. Functional ENTPD1 polymorphisms in African Americans with diabetes and end-stage renal disease. Diabetes 58, 999-1006 (2009).
16. Garcia-Hernandez, M. H., Portales-Cervantes, L., Cortez-Espinosa, N., Vargas-Morales, J. M., Fritche Salazar, J. F., Rivera-Lopez, E., Rodriguez-Rivera, J. G., Quezada-Calvillo, R. & Portales-Perez, D. P. Expression and function of P2X(7) receptor and CD39/Entpd1 in patients with type 2 diabetes and their association with biochemical parameters. Cellular immunology 269, 135-143 (2011).
17. Caminschi, I., Maraskovsky, E. & Heath, W. R. Targeting Dendritic Cells in vivo for Cancer Therapy. Frontiers in immunology 3, 13 (2012).
18. Ueberberg, S., Deutschbein, T., Klein, H. H., Dietrich, J. W., Akinturk, S., Prochnow, N., Schirrmacher, R. & Schneider, S. Protection from diabetes development by single-chain antibody-mediated delivery of a NF-kappaB inhibitor specifically to beta-cells in vivo. American journal of physiology. Endocrinology and metabolism 301, E83-90 (2011).
19. Lee, L. F., Logronio, K., Tu, G. H., Zhai, W., Ni, I., Mei, L., Dilley, J., Yu, J., Rajpal, A., Brown, C., Appah, C., Chin, S. M., Han, B., Affolter, T. & Lin, J. C. Anti-IL-7 receptor-alpha reverses established type 1 diabetes in nonobese diabetic mice by modulating effector T-cell function. Proceedings of the National Academy of Sciences of the United States of America 109, 12674-12679 (2012).

What is claimed is:

1. A method of generating an immunosuppressive dendritic cell comprising: contacting a dendritic cell with an effective amount of an IL-27 polypeptide agonist and an effective amount of an extracellular ATP degrading enzyme.

2. The method of claim 1, wherein the extracellular ATP degrading enzyme comprises apyrase or CD39.

3. The method of claim 1, wherein the extracellular ATP degrading enzyme is on a nanoparticle.

4. The method of claim 1, wherein the IL-27 polypeptide agonist is on a nanoparticle.

* * * * *

UNITED STATES PATENT AND TRADEMARK OFFICE
CERTIFICATE OF CORRECTION

PATENT NO. : 10,426,794 B2
APPLICATION NO. : 14/783679
DATED : October 1, 2019
INVENTOR(S) : Quintana et al.

Page 1 of 1

It is certified that error appears in the above-identified patent and that said Letters Patent is hereby corrected as shown below:

In the Specification

At Column 1, Line 14:
Insert the following heading and paragraph:
-- GOVERNMENT SUPPORT
This invention was made with government support under AI093903 awarded by the National Institutes of Health. The government has certain rights in the invention. --

Signed and Sealed this
Second Day of May, 2023

Katherine Kelly Vidal
*Director of the United States Patent and Trademark Office*